United States Patent
Kobayashi et al.

(10) Patent No.: US 7,125,877 B2
(45) Date of Patent: Oct. 24, 2006

(54) BENZIMIDAZOLE DERIVATIVES

(75) Inventors: Kensuke Kobayashi, Tsukuba (JP); Hirobumi Takahashi, Tsukuba (JP); Hiroshi Kawamoto, Tsukuba (JP); Tetsuya Kato, Tsukuba (JP); Satoru Itoh, Tsukuba (JP); Takashi Yoshizumi, Tsukuba (JP); Osamu Okamoto, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 341 days.

(21) Appl. No.: 10/437,176

(22) Filed: May 14, 2003

(65) Prior Publication Data

US 2003/0236267 A1  Dec. 25, 2003

(30) Foreign Application Priority Data

May 14, 2002 (JP) .............................. 2002-138143
Aug. 30, 2002 (JP) .............................. 2002-254039

(51) Int. Cl.
*A61K 31/496* (2006.01)
*C07D 403/04* (2006.01)
*C07D 405/14* (2006.01)

(52) U.S. Cl. ........................... 514/254.06; 514/217.09; 514/218; 514/249; 514/322; 514/394; 540/470; 540/480; 540/575; 540/603; 544/349; 544/370; 546/199; 548/306.1

(58) Field of Classification Search ................ 544/370; 514/254.06

See application file for complete search history.

(56) References Cited

FOREIGN PATENT DOCUMENTS

| EP | 0 254 322 A1 | 1/1988 |
|---|---|---|
| EP | 0 370 381 A2 | 5/1990 |
| EP | 0 963 987 A2 | 12/1999 |
| EP | 0 970 957 A1 | 1/2000 |
| WO | 99/36421 | 7/1999 |
| WO | 99/59997 | 11/1999 |
| WO | 00/14067 | 3/2000 |
| WO | 00/27815 | 5/2000 |

OTHER PUBLICATIONS

Shinkai et al. J.Med. Chem. vol. 43, p. 4667-4677 (2000).*
Yamada et al. British Journla of Pharmacology, vol. 135, p. 323-332 (2002).*
Meunier et al., Nature, 377, 532-534 (1995).
Levine et al., Society for Neuroscience, 22, 455 (1996).
Stratford et al., NeuroReport, 8, 423-426 (1997).
Sandin et al., European Journal of Neuroscience, 9, 194-197 (1997).
Murphy et al., Neuroscience, 75(1), 1-4 (1996).
Mogil et al., Neuroscience, 75(2), 333-337 (1996).
Kapusta et al., Life Sciences, 60(1), PL 15-21 (1997).
Gamusel et al., Life Sciences, 60(8), PL 141-145 (1997).
Jenck et al., Proceedings of National Academy of Sciences, 94, 14854-14858 (1997).
Ueda et al., Neuroscience Letters, 237, 136-138 (1997).
Manabe et al., Nature, 394 577-581 (1998).
Malin et al., Psychopharmacology, 151, 344-350 (2000).
Ueda et al., The Journal of Neuroscience, 20 7640-7647 (2000),.
Köster et al., Proceedings of National Academy of Sciences, 96, 10444-10449 (1999).

* cited by examiner

*Primary Examiner*—Emily Bernhardt
(74) *Attorney, Agent, or Firm*—Wenderoth, Lind & Ponack, L.L.P.

(57) ABSTRACT

This invention provides compounds which are represented by a general formula [I]

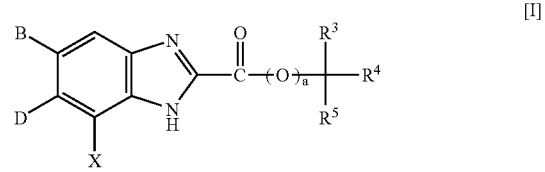

[in which X stands for hydrogen or halogen; B stands for halogen, cyano or optionally fluorine-substituted lower alkyl; D stands for a 3–10 membered aliphatic nitrogen-containing heterocyclic group; $R^3$, $R^4$ and $R^5$ may be same or different, and each stands for hydrogen, lower alkyl optionally having substituent group(s) and the like; and a is 0 or 1]. These compounds exhibit high affinity to nociceptin receptors and whereby inhibit actions of nociceptin, and are useful as an analgesic, antiobestic, agent for ameliorating brain function, treating agents for Alzheimer's disease and dementia, and therapeutic agents for schizophrenia, neurodegenerative diseases, depression, diabetes insipidus, polyuria, hypotension and the like.

9 Claims, No Drawings

BENZIMIDAZOLE DERIVATIVES

TECHNICAL FIELD

This invention relates to novel benzimidazole derivatives. These compounds exhibit an antagonism to binding of nociceptin to nociceptin receptor ORL1 (Opioid receptor-like-1 receptor) and are useful as an analgesic against diseases accompanied with pain such as cancerous pain, postoperative pain, migraine, gout, chronic rheumatism, chronic pain and neuralgia; a reliever against tolerance to narcotic analgesic represented by morphine; a reliever against dependence on narcotic analgesic represented by morphine or against addiction; an analgesic enhancer; an antiobestic or appetite suppressor; a treating or prophylactic agent for cognitive impairment and dementia/amnesia in aging, cerebrovascular diseases and Alzheimer's disease; an agent for treating developmental cognitive abnormality in attention deficit, hyperactivity disorder and learning disability; a remedy for schizophrenia; an agent for treating neurodegenerative diseases represented by Parkinsonism and chorea; an anti-depressant or treating agent for affective disorder; a treating or prophylactic agent for diabetes insipidus; a treating or prophylactic agent for polyuria; a remedy for hypotension, and the like.

BACKGROUND ART

Nociceptin (the same substance as orphanin FQ) is a peptide comprising 17 amino acid units having a similar structure to that of opioid peptide. Nociceptin has an augmenting activity on reaction against nociceptive stimulation, an appetite stimulating activity, an activity for reducing a space learning ability, an antagonism against an analgesic action of classic opiate agonists, a dopamine release inhibitory action, a water diuresis action, a vasodilative action and a systemic blood pressure-lowering action, and it is considered to take part in intracerebral controlling of pain, appetite and memory learning through a nociceptin receptor ORL1 [cf. *Nature*, 377, 532 (1995); *Society for Neuroscience*, 22, 455 (1996); *NeuroReport*, 8, 423 (1997); *Eur. J. Neuroscience*, 9, 194 (1997); *Neuroscience*, 75, 1 (1996); ibid., 333; *Life Sciences*, 60, PL15 (1997); ibid., PL141; *Proceedings for National Academy of Sciences*, 94, 14858 (1997)].

Further, it is known that morphine tolerance is reduced or memory and learning ability are improved in knockout mice in which expression of nociceptin receptor ORL1 is inhibited [cf. *Neuroscience Letters*, 237, 136 (1997)]; *Nature*, 394, 577 (1998)].

It has also been reported that nociceptin itself induces symptoms resembling withdrawal symptoms observed with morphine addicts, and that non-peptide nociceptin receptor antagonist improves morphine tolerance, dependence and symptoms resembling withdrawal symptoms [cf. *Psychopharmacology*, 151, 344–350 (2000); *Journal of Neuroscience*, 20, 7640 (2000)].

On the other hand, nociceptin protein precursor-defective mice are reported to show behaviors resembling anxiety and changes in stress response [cf *Proceedings for National Academy of Sciences*, 96, 10444 (1999)].

Hence the substances which specifically inhibit binding of nociceptin to nociceptin receptor ORL1 are useful as an analgesic against diseases accompanied with pain such as cancerous pain, postoperative pain, migraine, gout, chronic rheumatism, chronic pain and neuralgia; a reliever against tolerance to narcotic analgesic represented by morphine; a reliever against dependence on narcotic analgesic represented by morphine or against addiction; an analgesic enhancer; an antiobestic or appetite suppressor; a treating or prophylactic agent for cognitive impairment and dementia/amnesia in aging, cerebrovascular diseases and Alzheimer's disease; an agent for treating developmental cognitive abnormality in attention deficit, hyperactivity disorder and learning disability; a remedy for schizophrenia; an agent for treating neurodegenerative diseases represented by Parkinsonism and chorea; an anti-depressant or treating agent for affective disorder; a treating or prophylactic agent for diabetes insipidus; a treating or prophylactic agent for polyuria; a remedy for hypotension, and the like.

Substances which specifically inhibit binding of nociceptin to nociceptin receptor ORL1 are described, for example, in International Publications WO99/36421A, WO99/59997A, WO00/14067A and WO00/27815A; EPO Publications EP963987A2 and EP970957A1. None of these, however, relates to compounds having a benzimidazole ring.

Furthermore, EP 0254322 and EP 0370381 disclosed compounds resembling benzimidazole derivatives of the present invention, but none of the compounds disclosed in these publications has 1) a specific aliphatic carbonyl group or alicyclic amido group at 2-position of benzimidazole skeletal structure and/or 2) a nitrogen-containing heterocyclic ring at 6-position of said structure. They clearly differ from the compounds of the present invention.

DISCLOSURE OF THE INVENTION

We have concentratively investigated for compounds which inhibit binding of nociceptin to nociceptin receptor ORL1. In consequence, we now discovered that novel benzimidazole derivatives having structural characteristics of having 1) an aliphatic carbonyl group or alicyclic amido group at 2-position of benzimidazole skeletal structure and 2) a nitrogen-containing heterocyclic ring at 6-position of the same structure, possess antagonism to binding of nociceptin to nociceptin receptor ORL1 and, furthermore, such excellent physical properties suitable for medicines as high selectivity for nociceptin receptors and no side effect; and that they are effective as treating agents for a variety of diseases that are associated with nociceptin receptors. This invention is whereupon completed.

Thus, the invention provides benzimidazole derivatives which are represented by a general formula [I]

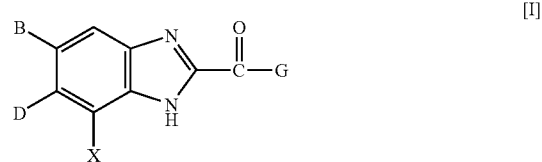

[in which

X stands for a hydrogen or halogen,

B stands for a halogen, cyano or optionally fluorine-substituted lower alkyl,

D stands for a group selected from a group consisting of the following formulae [D-1], [D-2] and [D-3]

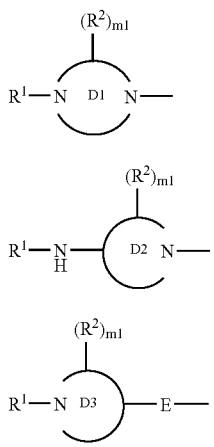

wherein

R¹ stands for hydrogen or a lower alkyl which may optionally be substituted with at least one substituent selected from a group consisting of halogen, hydroxyl, lower alkyloxy and lower cycloalkyl;

R² may be same or different where m1 is 2, which bind to optional carbon atom(s) on the aliphatic nitrogen-containing heterocyclic ring D1, D2 or D3, and stand for lower alkyl which may optionally be substituted with a substituent selected from a group consisting of halogen, hydroxyl, optionally fluorine-substituted lower alkyloxy, lower alkylcarbonyl, carboxyl, lower alkyloxycarbonyl, carbamoyl, mono-lower alkylcarbamoyl and di-lower alkylcarbamoyl, or R¹ and R² together form a C₂–C₄ alkylene, said alkylene being optionally substituted with a substituent selected from a group consisting of halogen, hydroxyl, lower alkyloxy, lower cycloalkyl, lower alkyloxycarbonyl, mono-lower alkylcarbamoyl and di-lower alkylcarbamoyl, m1 is 0 or an integer of 1 or 2, E stands for a binding hand, —NR— or —O—, where R stands for hydrogen, methyl or ethyl,

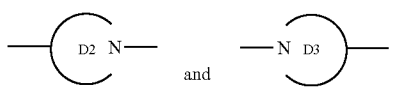

(hereinafter occasionally referred to as "D1 ring") stands for a 5–10 membered mono- or di-cyclic aliphatic, nitrogen-containing heterocyclic ring which has two nitrogen atoms; and (hereinafter occasionally referred to as "D2 ring" and "D3 ring", respectively) each stands for a 3–10 membered mono- or di-cyclic aliphatic nitrogen-containing heterocyclic ring having one nitrogen atom;

G stands for a group represented by a formula [G-1]

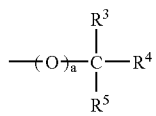

wherein
a is 0 or 1,
R³ stands for hydrogen, a substituent selected from a group consisting of the following list α, or a lower alkyl which may optionally be substituted with a substituent selected from the group consisting of the same list α, R⁴ and R⁵ may be same or different and each stands for hydrogen, a substituent selected from the group consisting of the list α, or a lower alkyl or lower cycloalkyl which may optionally be substituted with a substituent selected from the group consisting of the list α, or R⁴ and R⁵ together form, in combination with the carbon atom to which they bind, a 3–10 membered alicyclic group optionally having a hetero atom selected from a group consisting of nitrogen and oxygen, of the following formula [A]

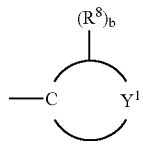

in which b is 0 or an integer of 1–4,

R⁸ may be same or different where b is 2–4, and bind to optional atom(s) on the aliphatic ring, each standing for a substituent selected from the group consisting of the list α or a lower alkyl which may optionally be substituted with a substituent selected from the group consisting of the list α, or two R⁸'s together form —NH—C(O)—O—CH₂— or an oxo group, Y¹ stands for —CH₂—, —NR⁹— or —O—, where R⁹ stands for a substituent selected from a group consisting of hydrogen, optionally fluorine-substituted lower alkyl, lower alkylcarbonyl, lower alkyloxycarbonyl, lower alkylsulfonyl, carbamoyl, mono-lower alkylcarbamoyl and di-lower alkylcarbamoyl;

[list α]

halogen, hydroxyl, amino, mono-lower alkylamino, di-lower alkylamino, optionally fluorine-substituted lower alkyloxy, lower alkyloxycarbonyl, (lower alkyloxycarbonyl)amino, (lower alkyloxycarbonyl)lower alkylamino, carboxyl, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl)lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsulfamoyl)lower alkylamino, (di-lower alkylsulfamoyl) lower alkylamino, phenyl which may optionally be substituted with lower alkyl, and tetrazolyl or oxadiazolyl which may optionally be substituted with lower alkyl] or their pharmaceutically acceptable salts.

The invention also provides a production process of the compounds represented by the general formula [I], which comprises condensing a compound represented by a general formula

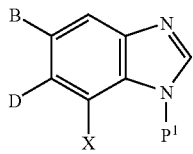

[in which
P$^1$ stands for a protective group.

B, D and X have the same significations as earlier defined, provided, where hydroxyl or carboxyl are present in the group D, they may optionally be also protected]

with a compound represented by a general formula

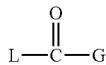

[in which
L stands for a leaving group;
G has the same signification as earlier defined]

in the presence of a base, and removing the protective group(s) from the formed compound where it contains such.

The invention furthermore provides pharmaceutical compositions containing the compounds represented by the general formula [I] and nociceptin receptor antagonists containing the compounds represented by the general formula [I] as active ingredients.

In the present specification, as examples of "halogen", fluorine, chlorine, bromine or iodine atom can be named.

"Lower alkyl" includes $C_1$–$C_6$ linear alkyl groups or $C_3$–$C_6$ branched alkyl groups, specific examples being methyl, ethyl, n-propyl, isopropyl, n-butyl, isobutyl, sec-butyl, tert-butyl, n-pentyl, isopentyl, neopentyl, tert-amyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like groups.

"Lower cycloalkyl" includes $C_3$–$C_6$ cycloalkyl, specific examples being cyclopropyl, cyclobutyl, cyclopentyl and cyclohexyl groups.

"Oxo group" signifies a group (=O) which forms carbonyl group (C=O) with a carbon atom in an organic compound. For example, taking the case of R$^8$, two R$^8$'s and the carbon atom to which they bind together form a carbonyl group.

"Optionally fluorine-substituted lower alkyl" includes lower alkyl or the lower alkyl in which a part or the whole of the hydrogen atoms are substituted with fluorine atom(s). As the latter, i.e., said fluorine-substituted lower alkyl groups, for example, fluoromethyl, difluoromethyl, trifluoromethyl, 2-fluoroethyl, 1,2-difluoroethyl and the like can be named.

"Optionally fluorine-substituted lower alkyloxy" includes groups in which a lower alkyl or fluorine-substituted lower alkyl binds to an oxygen atom, specific examples of lower alkyloxy being methoxy, ethoxy, n-propyloxy, isopropyloxy, n-butoxy, isobutoxy, tert-butoxy and n-pentyloxy; also as fluorine-substituted lower alkyloxy, for example, fluoromethoxy, difluoromethoxy, trifluoromethoxy and 1,2-difluoroethoxy can be named.

"Mono-lower alkylamino" is a group in which one of the hydrogen atoms of amino group (—NH$_2$) is substituted with lower alkyl, specific examples being methylamino, ethylamino, n-propylamino, isopropylamino, n-butylamino, sec-butylamino, tert-butylamino and the like groups.

"Di-lower alkylamino" is a group in which two hydrogen atoms of amino group (—NH$_2$) are each substituted with lower alkyl, specific examples being dimethylamino, diethylamino, ethylmethylamino, di-n-propylamino, methyl-n-propylamino, diisopropylamine and the like groups.

"Lower alkyloxycarbonyl" is a group formed by a carbonyl group (—CO—) binding to a lower alkyloxy and includes $C_1$–$C_6$ alkyloxycarbonyl, specific examples being methoxycarbonyl, ethoxycarbonyl, n-propyloxycarbonyl, isopropyloxycarbonyl, n-butoxycarbonyl, isobutoxycarbonyl, tert-butoxycarbonyl, n-pentyloxycarbonyl and the like groups.

"(Lower alkyloxycarbonyl)amino" is a group formed by an amino group (—NH$_2$) binding to a lower alkyloxycarbonyl and includes $C_1$–$C_6$ alkyloxycarbonylamino groups, specific examples being methoxycarbonylamino, ethoxycarbonylamino, n-propyloxycarbonylamino, isopropyloxycarbonylamino, n-butoxycarbonylamino, isobutoxycarbonylamino, tert-butoxycarbonylamino, n-pentyloxycarbonylamino and the like groups.

"(Lower alkyloxycarbonyl)lower alkylamino" is a group in which an alkyloxycarbonyl group binds, in place of the hydrogen, onto the nitrogen atom of mono-lower alkylamino group, specific examples being (methoxycarbonyl)methylamino, (ethoxycarbonyl)methylamino, (n-propyloxycarbonyl)methylamino and the like groups.

"Lower alkylcarbonyl" is a group formed by a carbonyl group (—CO—) binding to a lower alkyl and includes $C_1$–$C_6$ alkylcarbonyl, specific examples being acetyl, propionyl, butyryl, isobutyryl, valeryl, isovaleryl, pivaloyl and the like groups.

"Lower alkylcarbonylamino" is a group in which one of the hydrogens in an amino group (—NH$_2$) is substituted with a lower alkylcarbonyl, specific examples including acetamido, propionylamino, isobutyrylamino, valerylamino, isovalerylamino, pivaloylamino and the like groups.

"(Lower alkylcarbonyl)lower alkylamino" is a group in which the hydrogen on the nitrogen in mono-lower alkylamino is substituted with a lower alkylcarbonyl, specific examples including (methylcarbonyl)methylamino, (ethylcarbonyl)methylamino, (n-propylcarbonyl)methylamino and the like groups.

"Lower alkylcarbonyloxy" is a group formed by an oxygen atom binding to a lower alkylcarbonyl, specific examples including acetoxy, propionyloxy, valeryloxy, isovaleryloxy, pivaloyloxy and the like groups.

"Mono-lower alkylcarbamoyl" is a group in which one of the hydrogens in a carbamoyl group (—CONH$_2$) is substituted with a lower alkyl group, specific examples including methylcarbamoyl, ethylcarbamoyl, n-propylcarbamoyl, isopropylcarbamoyl, n-butylcarbamoyl, sec-butylcarbamoyl, tert-butylcarbamoyl and the like groups.

"Di-lower alkylcarbamoyl" is a group in which two hydrogen atoms in a carbamoyl group (—CONH$_2$) are substituted with lower alkyl groups, specific examples including dimethylcarbamoyl, diethylcarbamoyl, ethylmethylcarbamoyl, di-(n-propyl)carbamoyl, methyl(n-propyl)carbamoyl, diisopropylcarbamoyl and the like groups.

"Mono-lower alkylcarbamoylamino" is a group in which one of the hydrogen atoms of the amino group (—NH$_2$) is substituted with a mono-lower alkylcarbamoyl group, specific examples including methylcarbamoylamino, ethylcarbamoylamino, n-propylcarbamoylamino, isopropylcarbamoylamino, n-butylcarbamoylamino, sec-butylcarbamoylamino, tert-butylcarbamoylamino and the like groups.

"Di-lower alkyl carbamoylamino" is a group in which one of the hydrogen atoms in the amino group (—NH$_2$) is substituted with a di-lower alkylcarbamoyl group, specific examples including dimethylcarbamoylamino, diethylcarbamoylamino, di(n-propyl)carbamoylamino, diisopropylcarbamoylamino, di(n-butyl)carbamoylamino, di(sec-butyl)carbamoylamino, di(tert-butyl)carbamoylamino and the like groups.

"(Mono-lower alkylcarbamoyl)lower alkylamino" is a group in which the hydrogen atom on the nitrogen in mono-lower alkylamino is substituted with a mono-lower alkylcarbamoyl, specific examples including (mono-methylcarbamoyl)methylamino, (mono-ethylcarbamoyl)methylamino, [mono-(n-propyl)carbamoyl]methylamino and the like groups.

"(Di-lower alkyl carbamoyl)lower alkylamino" is a group in which the hydrogen atom on the nitrogen in a mono-lower alkylamino is substituted with a di-lower alkylcarbamoyl, specific examples including (dimethylcarbamoyl)methylamino, (diethylcarbamoyl)methylamino, [di-(n-propyl)carbamoyl]methylamino and the like groups.

"Mono-lower alkylcarbamoyloxy" is a group in which an oxygen atom is bound to a lower alkylcarbamoyl, specific examples including methylcarbamoyloxy, ethylcarbamoyloxy, n-propylcarbamoyloxy, isopropylcarbamoyloxy, n-butylcarbamoyloxy, sec-butylcarbamoyloxy, tert-butylcarbamoyloxy and the like groups.

"Di-lower alkylcarbamoyloxy" is a group in which an oxygen atom is bound to a di-lower alkylcarbamoyl, specific examples including dimethylcarbamoyloxy, diethylcarbamoyloxy, ethylmethylcarbamoyloxy, di(n-propyl)carbamoyloxy, methyl(n-propyl)carbamoyloxy, diisopropylcarbamoyloxy and the like groups.

"Lower alkylsulfonyl" is a group formed by a sulfonyl group (—SO$_2$) binding to a lower alkyl, specific examples including methylsulfonyl, ethylsulfonyl, n-propylsulfonyl, isopropylsulfonyl, n-butylsulfonyl, sec-butylsulfonyl, tert-butylsulfonyl and the like groups.

"Lower alkylsulfonylamino" is a group in which one of the hydrogen atoms of amino group (—NH$_2$) is substituted with a lower alkylsulfonyl, specific examples including methylsulfonylamino, ethylsulfonylamino, n-propylsulfonylamino, isopropylsulfonylamino, n-butylsulfonylamino, sec-butylsulfonylamino, tert-butylsulfonylamino and the like groups.

"Mono-lower alkylsulfamoyl" is a group in which one of the hydrogen atoms of sulfamoyl group (—SO$_2$NH$_2$) is substituted with a lower alkyl, specific examples including monomethylsulfamoyl, monoethylsulfamoyl, mono(n-propyl)sulfamoyl, monoisopropylsulfamoyl, mono(n-butyl)sulfamoyl, mono(sec-butyl)sulfamoyl, mono(tert-butyl)sulfamoyl and the like groups.

"Di-lower alkylsulfamoyl" is a group in which the two hydrogen atoms of sulfamoyl group (—SO$_2$NH$_2$) are each substituted with lower alkyl, specific examples including dimethylsulfamoyl, diethylsulfamoyl, di(n-propyl)sulfamoyl, diisopropylsulfamoyl, di(n-butyl)sulfamoyl, di(sec-butyl)sulfamoyl, di(tert-butyl)sulfamoyl and the like groups.

"(Mono-lower alkylsulfamoyl)amino" is a group in which one of the hydrogen atoms of amino group (—NH$_2$) is substituted with a mono-lower alkylsulfamoyl group, specific examples including (monomethylsulfamoyl)amino, (monoethylsulfamoyl)amino, [mono(n-propyl)sulfamoyl]amino, (monoisopropylsulfamoyl)amino, [mono(n-butyl)sulfamoyl]amino, [mono(sec-butyl)sulfamoyl]amino, [mono(tert-butyl)sulfamoyl]amino and the like groups.

"(Di-lower alkylsulfamoyl)amino" is a group in which one of the hydrogen atoms of amino group (—NH$_2$) is substituted with a di-lower alkylsulfamoyl group, specific examples including (dimethylsulfamoyl)amino, (diethylsulfamoyl)amino, (ethylmethylsulfamoyl)amino, [di(n-propyl)sulfamoyl]amino, [methyl(n-propyl)sulfamoyl]amino, (diisopropylsulfamoyl)amino and the like groups.

"(Mono-lower alkylsulfamoyl)lower alkylamino" is a group in which the hydrogen atom on the nitrogen of mono-lower alkylamino is substituted with a mono-lower alkylsulfamoyl, specific examples including (monomethylsulfamoyl)methylamino, (monoethylsulfamoyl)methylamino, [mono(n-propyl)sulfamoyl]methylamino and the like groups.

"(Di-lower alkylsulfamoyl)lower alkylamino" is a group in which the hydrogen atom on nitrogen of a mono-lower alkylamino group is substituted with a di-lower alkylsulfamoyl group, specific examples including (dimethylsulfamoyl)methylamino, (diethylsulfamoyl)methylamino, [di(n-propyl)sulfamoyl]methylamino and the like groups.

As examples of "3- to 10-membered mono- or di-cyclic nitrogen-containing aliphatic heterocyclic ring containing one nitrogen atom", azetidine ring, pyrrolidine ring, piperidine ring, hexamethyleneimine ring, heptamethyleneimine ring and the like can be named.

As examples of "5- to 10-membered mono- or di-cyclic nitrogen-containing aliphatic heterocyclic ring containing two nitrogen atoms", piperazine ring, 2,5-diazabicyclo[2.2.1]heptane ring, 1,4-diazepane ring, 2,5-diazabicyclo[2.2.2]octane ring, 1,4-diazabicyclo[3.2.1]octane ring, 3,4,5,6-tetrahydropyrrolo-[3,4-C]-2(1H)pyrrole ring, decahydro[1,6]naphthyridine ring and the like can be named.

The alicyclic ring in "3- to 10-membered alicyclic group optionally having hereto atom(s) selected from a group consisting of nitrogen and oxygen" is an aliphatic ring in which one or two of the 3 to 10 ring members may be replaced with nitrogen or oxygen, specific examples including cyclopropane ring, cyclobutane ring, cyclopentane ring, cyclohexane ring, azetidine ring, pyrrolidine ring, piperidine ring, piperazine ring, hexamethyleneimine ring, heptamethyleneimine ring, homopiperazine ring, 2,5-diazabicyclo[2.2.1]heptane ring, 1,4-diazepane ring, 2,5-diazabicyclo[2.2.2]octane ring, 1,4-diazabicyclo[3.2.1]octane ring, tetrahydrofuran ring, tetrahydropyran ring, morpholine ring and the like.

"Phenyl which may optionally be substituted with lower alkyl" includes phenyl and phenyl which is substituted with one or two lower alkyl groups. As examples of such lower alkyl-substituted phenyl, toluyl, xylyl and the like can be named.

As "tetrazolyl or oxadiazolyl which may optionally be substituted with lower alkyl", for example, tetrazolyl, oxadiazolyl, methyltetrazolyl, ethyltetrazolyl, methyloxadiazolyl, ethyloxadiazolyl and the like can be named.

"Pharmaceutically acceptable salts" of the benzimidazole derivatives represented by the general formula [I] can be customary salts which are acceptable for medicines. For example, where the compounds of the formula [I] have an amino group, acid addition salts at the amino group; or when they have a basic heterocyclic ring including piperidine ring, acid addition salts at said basic heterocyclic ring; or when the compounds of the general formula (I) have a carboxyl group, base-addition salts at the carboxyl group.

As the acid addition salts, for example, inorganic acid salts such as hydrochloride, sulfate, nitrate, phosphate and perchlorate; organic acid salts such as maleate, fumarate, tartarate, citrate, ascorbate and trifluoroacetate; and sulfonates such as methanesulfonate, isethionate, benzenesulfonate and p-toluenesulfonate can be named.

As the base addition salts, for example, alkali metal salts such as sodium salt and potassium salt; alkaline earth metal salts such as calcium salt and magnesium salt; ammonium salt; organic amine salts such as trimethylamine salt, triethylamine salt, dicyclohexylamine salt, ethanolamine salt, diethanolamine salt, triethanolamine salt, procaine salt and N,N'-dibenzylethylenediamine salt can be named.

Hereinafter benzimidazole derivatives of the present invention are explained in further details, referring to specific examples. In the present specification, the position numbers of benzimidazole skeleton are as in the formula below.

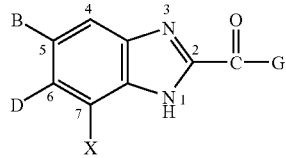
[I]

The compounds represented by the general formula [I] have isomers which are represented by the formula [b] having an equilibrium relationship, which compounds also being encompassed by the present invention.

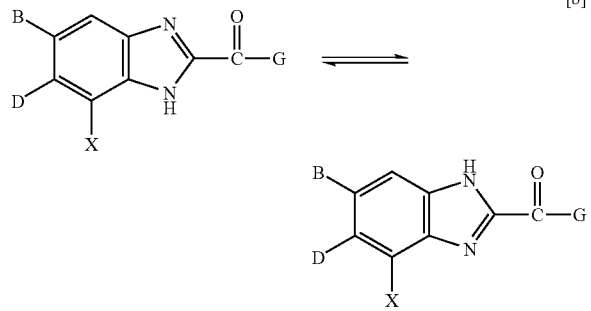
[b]

In the compounds represented by the general formula [I], as X, particularly hydrogen or halogen are preferred; and as B, particularly chlorine, cyano or methyl are preferred.

D stands for a group selected from the following 1) to 3):
1) groups represented by a formula [D-1]

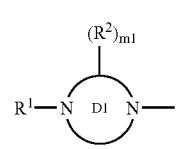
[D-1]

[in which $R^1$, $R^2$, m1 and D1 ring have the same significations as earlier defined];
2) groups represented by a formula [D-2]

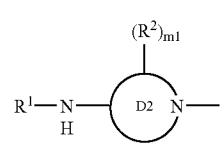
[D-2]

[in which $R^1$, $R^2$, m1 and D2 ring have the same significations as earlier defined];
3) groups represented by a formula [D-3]

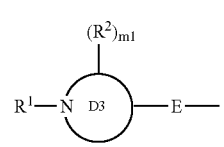
[D-3]

[in which $R^1$, $R^2$, E, m1 and D3 ring have the same significations as earlier defined].

In the above formulae [D-1] to [D-3], as specific $R^1$, for example, hydrogen, methyl, ethyl, isopropyl, 2-fluoroethyl, 3-fluoropropyl, 2-hydroxyethyl, 3-hydroxypropyl, 2-methoxyethyl, 3-methoxypropyl, cyclopropylmethyl, 2,2-dimethyl-2-hydroxyethyl, 2-hydroxy-1-(hydroxymethyl)ethyl, (1-hydroxycyclopropyl)methyl and the like can be named, of which methyl, ethyl, 2-hydroxyethyl, 2-fluoroethyl, 2-methoxyethyl and isopropyl are preferred. Also as $R^2$, methyl, ethyl, hydroxymethyl, fluoromethyl can be named as preferred examples.

Furthermore, as examples of $C_2$–$C_4$ alkylene which is formed by $R^1$ and $R^2$ together, 1,2-dimethylene, 1,3-trimethylene, 1,4-tetramethylene and the like can be named, which alkylene groups may optionally be substituted with a substituent selected from a group consisting of halogen, hydroxyl, lower alkyloxy, lower cycloalkyl, lower alkyloxycarbonyl, mono-lower alkylcarbamoyl and di-lower alkylcarbamoyl. Such $R^1$ and $R^2$ which together form a $C_2$–$C_4$ alkylene preferably are bound onto mutually adjacent atoms, and 1,3-trimethylene is particularly preferred.

The subscript m1 is 0, 1 or 2, and where m1 is 0, hydrogen binds to D1–D3 ring instead of $R^2$. When R1 and R2 together form a $C_2$–$C_4$ alkylene, m1 is 1 or 2.

As specific examples of the groups represented by the formula [D-1], 1,4-piperazin-1-yl (hereafter referred to as "piperazin-1-yl"), 4-methylpiperazin-1-yl, 4-ethylpiperazin-1-yl, 4-isopropylpiperazin-1-yl, 4-(cyclopropylmethyl)piperazin-1-yl, 4-(2-hydroxyethyl)piperazin-1-yl, 4-(3-hydroxypropyl)piperazin-1-yl, 4-(2-fluoroethyl)piperazin-1-yl, 4-(2-methoxyethyl)piperazin-1-yl, 4-(2-methyl-2-hydroxypropyl)piperazin-1-yl, 4-[2-hydroxy-1-(hydroxymethyl)ethyl]piperazin-1-yl, 4-methyl-3-(hydroxymethyl)piperazin-1-yl, 3-methylpiperazin-1-yl, 4-methyl-3-methylpiperazin-1-yl, 4-ethyl-3-methylpiperazin-1-yl, 4-isopropyl-3-methylpiperazin-1-yl, 4-cyclopropylmethyl-3-methylpiperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)-3-methylpiperazin-1-yl, 4-(3-hydroxypropyl)-3-methylpiperazin-1-yl, 4-(2-methyl-2-hydroxypropyl)-3-methylpiperazin-1-yl, 4-[2-hydroxy-1-(hydroxymethyl)ethyl]-3-methylpiperazin-1-yl, 4-methyl-5-(hydroxymethyl)-3-methylpiperazin-1-yl, 3-(hydroxymethyl)piperazin-1-yl, 3,5-dimethylpiperazin-1-yl, 1,4-diazepan-1-yl, 4-methyl-1,4-diazepan-1-yl, 4-ethyl-1,4-diazepan-1-yl, 4-isopropyl-1,4-diazepan-1-yl, 4-cyclopropylmethyl-1,4-diazepan-1-yl, 4-(2-hydroxyethyl)-1,4-diazepan-1-yl, 4-(3-hydroxypropyl)-1,4-diazepan-1-yl, 4-(2-methyl-2-hydroxypropyl)-1,4-diazepan-1-yl, 4-[2-hydroxy-1-(hydroxymethyl)ethyl]-1,4-diazepan-1-yl, 2,5-diazabicyclo[2.2.1]heptan-2-yl, 5-(2-hydroxyethyl)-2,5-diazabicyclo[2.2.1]heptan-2-yl, 1,4-diazabicyclo[3.2.1]octan-4-yl, 4-(1-hydroxycyclopropyl)methylpiperazin-1-yl, 4-(1-hydroxycyclopropyl)methyl-2-methylpiperazin-1-yl, 2,4-dimethylpiperazin-1-yl, 2,2-dimethyl-4-ethylpiperazin-1-yl, 1,4-diazabicyclo[4.3.0]nonan-4-yl and the like can be named.

As specific examples of the groups represented by the formula [D-2], 3-amino-azetidin-1-yl, 3-amino-hexamethyleneimin-1-yl, 4-amino-hexamethyleneimin-1-yl, 4-(methylamino)piperidin-1 yl, 4-(ethylamino)piperidin-1-yl, 4-(isopropylamino)piperidin-1-yl, 4-(cyclohexylmethylamino)piperidin-1-yl, 4-((2-hydroxyethyl)amino)piperidin-1-yl, 3-(methylamino)piperidin-1-yl, 3-(ethylamino)piperidin-1-yl, 3-(isopropylamino)piperidin-1-yl, 3-(cyclohexylmethylamino)piperidin-1-yl, 3-((2-hydroxyethyl)amino)piperidin-1-yl, 3-(methylamino)pyrrolidin-1-yl, 3-(ethylamino)pyrrolidin-1-yl, 3-(isopropylamino)pyrrolidin-1-yl, 3-(cyclohexylmethylamino)pyrrolidin-1-yl, 3-((2-hydroxyethyl)amino)pyrrolidin-1-yl and the like can be named.

As specific examples of the groups represented by the formula [D-3], pyrrolidin-2-yl, pyrrolidin-3-yl, piperidin-2-yl, piperidin-3-yl, piperidin-4-yl (which may hereinafter be referred to as "4-piperidinyl"), 1-ethylpiperidin-4-yl, 1-isopropylpiperidin-4-yl, 1-(cyclopropylmethyl)piperidin-4-yl, 1-(2-hydroxyethyl)piperidin-4-yl, 1-(3-hydroxypropyl)piperidin-4-yl, 1-(2-methyl-2-hydroxypropyl)piperidin-4-yl, 1-[2-hydroxy-1-(hydroxymethyl)ethyl]piperidin-4-yl, 1-ethylpyrrolidin-3-yl, 1-(2-methoxyethyl)pyrrolidin-3-yl, [1-(2-methoxyethyl)pyrrolidin-3-yl](methyl)amino, [1-(2-methoxyethyl)pyrrolidin-3-yl]oxy, 1-methylpiperidin-4-yl and the like can be named.

As the group [D], those represented by the formula [D-1] are preferred, in particular, 4-methylpiperazin-1-yl, 4-ethylpiperazin-1-yl, 4-isopropylpiperazin-1-yl, 4-(2-fluoroethyl)piperazin-1-yl, 4-(2-methoxyethyl)piperazin-1-yl, 4-ethyl-2-methylpiperazin-1-yl, 4-(2-fuoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl, 2,4-dimethylpiperazin-1-yl, 4-(1-hydroxycyclopropyl)methylpiperazin-1-yl, 4-(1-hydroxycyclopropyl)methyl-2-methylpiperazin-1-yl, 2,2-dimethyl-4-ethylpiperazin-1-yl and 1,4-diazabicyclo[4.3.0]nonan-4-yl are preferred. Inter alia, 4-methylpiperazin-1-yl, 4-ethylpiperazin-1-yl, 4-(2-fluoroethyl)piperazin-1-yl, 4-(2-methoxyethyl)piperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl and 1,4-diazabicyclo[4.3.0]nonan-4-yl are particularly favorable.

In the group represented by the formula [G-1] in the compounds represented by the general formula [I], as preferred $R^3$, hydrogen, methyl, ethyl, n-propyl, isopropyl, n-butyl, isobutyl, 1,1-dimethylpropyl, 2,2-dimethylpropyl, 1-ethylpropyl, 1-methoxy-1-methylethyl, 4-methylpentyl, 2-hydroxypropyl, 2-methoxypropyl, 2-hydroxy-2-methylpropyl, 2-methoxy-2-methylpropyl, 2-(methoxycarbonylamino)ethyl, 2-acetoxypropyl, 1-ethyl-2-hydroxy-2-methylpropyl, 1-ethyl-1-hydroxypropyl, 2,2-dimethyl-1-oxopropyl, 2-hydroxy-1,2-dimethylpropyl, 2-methoxy-1,2-dimethylpropyl, 2-amino-2-methylpropyl, hydroxymethyl, methoxymethyl, ethoxymethyl, 2-hydroxyethyl, 1,1-dimethyl-1-hydroxymethyl, (dimethylamino)methyl, (diisopropylamino)methyl, 1,3-dimethyl-3-hydroxybutyl, 1,3-dimethyl-3-methoxybutyl, 2-(methanesulfonamido)ethyl, fluorine, chlorine, hydroxyl, methoxy, ethoxy, acetyl, ethylcarbonyl, dimethylamino, diethylamino, diisopropylamino, methoxycarbonyl, phenyl, toluyl, tetrazolyl, methyltetrazolyl, oxadiazolyl, methyloxadiazolyl, methoxycarbonylamino, ethoxycarbonylamino, tert-butoxycarbonylamino, methoxyethyl, cyano, fluoromethyl, difluoromethyl, trifluoromethyl and (methoxycarbonylamino)methyl can be named.

As $R^4$ or $R^5$, hydrogen, methyl, ethyl, n-propyl, isopropyl, n-butyl, isobutyl, 1,1-dimethylpropyl, 2,2-dimethylpropyl, 1-ethylpropyl, 1-methoxy-1-methylethyl, 4-methylpentyl, 2-hydroxypropyl, 2-methoxypropyl, 2-hydroxy-2-methylpropyl, 2-methoxy-2-methylpropyl, 2-(methoxycarbonylamino)ethyl, 2-acetoxypropyl, 1-ethyl-2-hydroxy-2-methylpropyl, 1-ethyl-1-hydroxypropyl, 2,2-dimethyl-1-oxopropyl, 2-hydroxy-1,2-dimethylpropyl, 2-methoxy-1,2-dimethylpropyl, 2-amino-2-methylpropyl, hydroxymethyl, methoxymethyl, ethoxymethyl, 2-hydroxyethyl, 1,1-dimethyl-1-hydroxymethyl, (dimethylamino)methyl, (diisopropylamino)methyl, 1,3-dimethyl-3-hydroxybutyl, 1,3-dimethyl-3-methoxybutyl, 2-(methanesulfonamido)ethyl, fluorine, chlorine, hydroxyl, methoxy, ethoxy, acetyl, ethylcarbonyl, dimethylamino, diethylamino, diisopropylamino, methoxycarbonyl, phenyl, toluyl, tetrazolyl, methyltetrazolyl, oxadiazolyl, methyloxadiazolyl, methoxycarbonylamino, ethoxycarbonylamino, tert-butoxycarbonylamino, methoxyethyl, cyano, fluoromethyl, difluoromethyl, trifluoromethyl, (methoxycarbonylamino)methyl, cyclobutyl, cyclopentyl and cyclohexyl are preferred.

As the aliphatic ring in the occasion of $R^4$ and $R^5$ together forming an alicyclic ring group in combination with the carbon atom to which they bind, cyclobutane ring, cyclopentane ring, cyclohexane ring, tetrahydrofuran ring, tetrahydropyran ring, piperazine ring and pyrrolidine ring are preferred.

As $R^8$, methyl, ethyl, hydroxyl, acetyl, acetamido, N-methylacetamido, methylsulfonyl, ethylsulfonyl, methanesulfonamido, methylamino, methylaminocarbonyl, methoxycarbonyl, ethoxycarbonyl, pivaloyl, methoxycarbonylamino, ethoxycarbonylamino, isopropyloxycarbonylamino, carbamoyl, (dimethylamino)carbonyl, [(diethylamino)carbonyl], phenyl, toluyl, tetrazolyl, 2-methyltetrazolyl, 1,3,4-oxadiazolyl, 2-methyl-1,3,4-oxadiazolyl, 2-pyrrolidon-1-yl and cyano are preferred.

Thus, as specific examples of the groups represented by the formula [G-1], 1-methylethyl, 2-dimethylamino-1,1- dimethylethyl, 2-dimethylamino-2-methylethyl, 2-dimethylamino-1-methylethyl, 2-dimethylamino-2,2-dimethylethyl, 2-(diisopropylamino)ethyl, 2,2-dimethyl-2-hydroxyethyl, 2-hydroxy-1-(hydroxymethyl)ethyl, 2-ethoxy-1-(ethoxymethyl)ethyl, 2-methoxy-1-(methoxymethyl)ethyl, 1-ethylpropyl, 1-(methoxycarbonyl)propyl, 2-methoxy-2-methylpropyl, 1-acetyl-2-oxopropyl, 1-[(tert-butylamino)carbonyl] propyl, tert-butyl, 1,1-dimethylpropyl, 1,1-dimethylbutyl, 2-ethylbutyl, 3-amino-3-methylbutyl, 3-methoxy-3-methylbutyl, 3-methoxy-1,3-dimethylbutyl, 3-methoxybutyl, 1,3,3-trimethylbutyl, 3-hydroxy-2,3-dimethylbutyl, 3,3-dimethyl-2-oxobutyl, 1-ethyl-3-methyl-3-hydroxybutyl, 2-ethyl-2-hydroxybutyl, 2-ethyl-3-hydroxy-3-methylbutyl, 3-acetoxy-1,1-dimethylbutyl, 3-hydroxy-1,1-dimethylbutyl, 3-hydroxy-1,3-dimethylbutyl, 3-hydroxy-3-methylbutyl, 3-hydroxy-1-methylbutyl, 2,4-dimethyl-4-methoxypentyl, 3-ethyl-3-hydroxypentyl, 5-methylhexyl, 1-methylethyloxy, 1-ethylpropyloxy, 2-methylpropyloxy, 1,1-dimethylpropyloxy, 3-methoxycarbonylamino-1,1-dimethylpropyl, 3-methanesulfonamido-1,1-dimethylpropyl, 2,2-dimethylpropyl, cyclopentylmethyl, 2-cyclopentylethyl, 2-(1-hydroxycyclopentyl)ethyl, cyclohexylmethyl, cyclohexylethyl, 2-(1-hydroxycyclohexyl)ethyl, 1,1-bis(methoxymethyl)ethyl, 1-methyl-1-(p-toluyl)ethyl and the like can be named.

As specific examples of the substituent group [G-1] wherein $R^4$ and $R^5$ together form an aliphatic ring group of the formula [A] in combination with the carbon atom to which they bind, cyclobutyl, 1-methylcyclobutyl, 3-methoxycarbonylamino-1-methylcyclobutyl, cyclopentyl, 1-methylcyclopentyl, cyclohexyl, 1-methylcyclohexyl, 4-oxocyclohexyl, 4-acetamido-1-methylcyclohexyl, 4-(N-methylacetamido)-1-methylcyclohexyl, 4-(acetamino) cyclohexyl, 4-methanesulfonamido-1-methylcyclohexyl, 4-(methylamino)carbonyl-1-methylcyclohexyl, 4-(methoxycarbonyl)cyclohexyl, 4-(ethoxycarbonylamino)cyclohexyl, 4-hydroxycyclohexyl, 4-hydroxy-4-methylcyclohexyl, 1,4-dimethyl-4-hydroxycyclohexyl, 4-methoxycarbonylamino-1-methoxymethylcyclohexyl, 4-hydroxy-1-methoxymethyl-4-methylcyclohexyl, 4-(methoxycarbonylamino)cyclohexyl, 4-(isopropoxycarbonylamino)cyclohexyl, 4-methoxycarbonylamino-1-methylcyclohexyl, 4-methoxycarbonylamino-1-ethylcyclohexyl, 4-ethoxycarbonylamino-1-methylcyclohexyl, 4-hydroxy-1-methylcyclohexyl, 4-(2-pyrrolidon-1-yl)-1-methylcyclohexyl, 4-(1-methyltetrazol-3-yl)-1-methylcyclohexyl, 4-(2-methyltetrazol-5-yl)-1-methylcyclohexyl, 4-(2-methyl-1,3,4-oxadiazol-5-yl)-1-methylcyclohexyl, 4-(1,3,4-oxadiazol-2-yl)-1-methylcyclohexyl, 1-methylpyrrolidin-3-yl, 1-acetyl-4-methylpiperidin-4-yl, 1-(methoxycarbonyl)pyrrolidin-3-yl, 1-methylpiperidin-4-yl, 1-(ethoxycarbonyl)piperidin-4-yl, 1-(methoxycarbonyl)piperidin-4-yl, 1-(methylsulfonyl)piperidin-4-yl, 1-(ethylsulfoyl)piperidin-4-yl, 1-acetylpiperidin-4-yl, 1-(ethoxycarbonyl)piperidin-4-yl, 1-pivaloylpiperidin-4-yl, 1-([(diethylamino)carbonyl])piperidin-4-yl, 1-methylpiperidin-3-yl, 1-(methoxycarbonyl)piperidin-3-yl, 1-methoxycarbonyl-4-methylpiperidin-4-yl, 1-ethoxycarbonyl-4-methylpiperidin-4-yl, 1,4-oxaspiro[4,5]decan-8-yl, 7-methyl-3-oxa-1-azaspiro[4,5]decan-2-on-7-yl, tetrahydro-2H-pyran-4-yl, tetrahydro-2H-pyran-4-ylmethyl, 4-methyl-tetrahydro-2H-pyran-4-yl, 4-ethyl-tetrahydro-2H-pyran-4-yl and the like can be named.

Of these substituents of the formula [G-1], those of the following groups a) and b), inter alia, the following group c), are preferred:

a) formula [G-2]

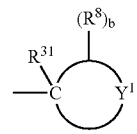

[G-2]

[in which

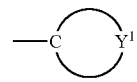

stands for a 3- to 10-membered alicyclic ring optionally having hetero atom(s) selected from a group consisting of nitrogen and oxygen,
$R^{31}$ stands for a lower alkyl optionally substituted with substituent(s) selected from the earlier given list α, and
$Y^1$, $R^8$ and b have the same significations to those earlier defined];

b) formula [G-3]

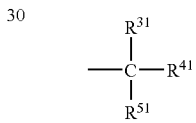

[G-3]

[in which
$R^{31}$ has the same signification as above, and
$R^{41}$ and $R^{51}$ may be same or different and each has the same signification to $R^{31}$];

c) formula [G-4]

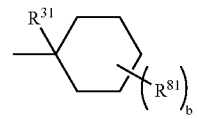

[G-4]

[in which
$R^{81}$ stands for a substituent selected from said list α, or a lower alkyl optionally substituted with a substituent selected from the list α, and
$R^{31}$ and b have the above significations].

In the formula [G-3] or [G-4]: preferred $R^{31}$, $R^{41}$ or $R^{51}$ are, for example, methyl, ethyl, n-propyl, isopropyl, n-butyl, isobutyl, 1,1-dimethylpropyl, 2-(methoxycarbonylamino) ethyl, methoxymethyl, and 2-(methanesulfonamido)ethyl; preferred examples of $R^{81}$ include methyl, ethyl, hydroxyl, acetyl, acetamido, N-methylacetamido, methylsulfonyl, ethylsulfonyl, methanesulfonamido, methylamino, methylaminocarbonyl, methoxycarbonyl, ethoxycarbonyl, pivaloyl, methoxycarbonylamino, ethoxycarbonylamino, isopropyloxycarbonylamino, carbamoyl, (dimethylamino)carbonyl and (diethylamino)carbonyl; and b is preferably 1 or 2.

Thus as G, 4-methoxycarbonylamino-1-methylcyclohexyl, 4-methoxycarbonylamino-1-ethylcyclohexyl, 2,2-dimethylpropyl, tert-amyl, 1-acetyl-4-methylpiperidin-4-yl, 4-hydroxy-1-methylcyclohexyl, 1,4-dimethyl-4-hydroxycyclohexyl, 4-methoxycarbonylamino-1-methoxymethylcyclohexyl, 4-hydroxy-1-methoxymethyl-4-methylcyclohexyl, 4-methyltetrahydro-2H-pyran-4-yl, 4-(1-methyltetrazol-3-yl)-1-methylcyclohexyl, 4-(2-methyl-1,3,4-oxadiazol-5-yl)-1-methylcyclohexyl, 4-(1,3,4-oxadiazol-2-yl)-1-methylcyclohexyl, 4-acetamido-1-methylcyclohexyl, 4-(N-methylacetamido)-1-methylcyclohexyl, 4-methanesulfonamido-1-methylcyclohexyl, 4-[(methylamino)carbonyl]-1-methylcyclohexyl, 3-methoxycarbonylamino-1,1-dimethylpropyl, 3-methanesulfonamido-1,1-dimethylpropyl, 3-methoxycarbonylamino-1-methylcyclobutyl, 7-methyl-3-oxa-1-azaspiro[4,5]decan-2-on-7-yl and 1,1-bis(methoxymethyl)ethyl are preferred.

Of those preferred G groups, in particular, 4-methoxycarbonylamino-1-methylcyclohexyl, 4-methoxycarbonylamino-1-ethylcyclohexyl, 1-acetyl-4-methylpiperidin-4-yl, 4-hydroxy-1-methylcyclohexyl, 1,4-dimethyl-4-hydroxycyclohexyl, 4-methoxycarbonylamino-1-methoxymethylcyclohexyl, 4-hydroxy-1-methoxymethyl-4-methylcyclohexyl, 4-methyltetrahydro-2H-pyran-4-yl, 4-(1-methyltetrazol-3-yl)-1-methylcyclohexyl, 4-acetamido-1-methylcyclohexyl, 4-[(methylamino)carbonyl]-1-methylcyclohexyl, 3-methoxycarbonylamino-1-methylcyclobutyl and 1,1-bis(methoxymethyl)ethyl are advantageous.

Among the compounds represented by the general formula [I], those preferred are the following. In the following structural formulae, signs and symbols have the same significations as earlier defined:

a1) compounds represented by a general formula [I-1]

[I-1]

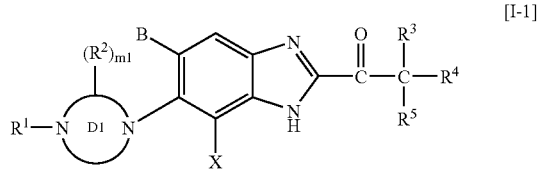

a2) compounds represented by a general formula [I-2]

[I-2]

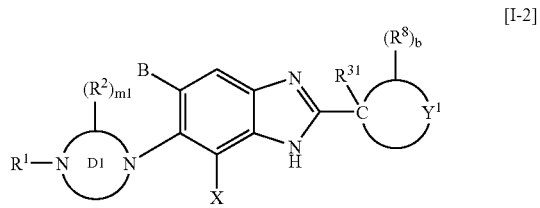

a3) compounds represented by a general formula [I-3]

[I-3]

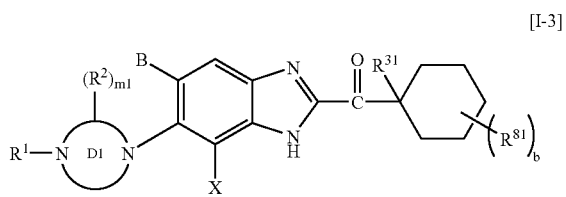

a4) compounds represented by a general formula [I-4]

[I-4]

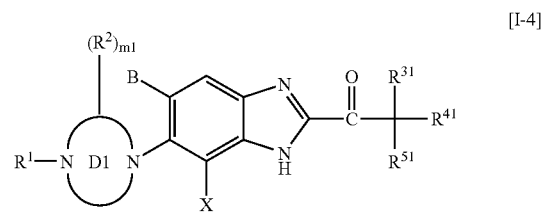

a5) compounds of above a1) to a4) in which X is hydrogen or fluorine;

a6) compounds of above a1) to a5) in which B is chlorine, cyano or methyl;

a7) compounds of above a1) to a6) in which the substituent corresponding to the substituent D is selected from the group consisting of 4-methylpiperazin-1-yl, 4-ethylpiperazin-1-yl, 4-(2-fluoroethyl)piperazin-1-yl, 4-(2-methoxyethyl)piperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl and 1,4-diazabicyclo[4.3.0]nonan-4-yl;

a8) compounds of above a3) in which the substituent corresponding to substituent G is selected from the group consisting of 4-methoxycarbonylamino-1-methylcyclohexyl, 4-methoxycarbonylamino-1-ethylcyclohexyl, 4-hydroxy-1-methylcyclohexyl, 1,4-dimethyl-4-hydroxycyclohexyl, 4-methoxycarbonylamino-1-methoxymethylcyclohexyl, 4-hydroxy-1-methoxymethyl-4-methylcyclohexyl, 4-(1-methyltetrazol-3-yl)-1-methylcyclohexyl, 4-acetamido-1-methylcyclohexyl and 4-[(methylamino)carbonyl]-1-methylcyclohexyl.

Inter alia, the compounds represented by above general formulae [I-2] to [I-4], in particular, those of the general formula [I-3], exhibit high selectivity for nociceptin receptors and excellent antagonism, little action on functions of the central nervous system attributable to their binding to other receptors, excellent in vivo metabolic properties, no side-action on cardiac function or liver function and excellent properties as medicines. Still in addition, these compounds exhibit, when they are caused to act as medicines on the central system, excellent intracerebral transmigration; and when they are orally administered, exhibit excellent in vivo maintenance of effective concentration.

As the typical examples of the compounds represented by the general formula [I], the following are listed.

| Example | Structural formula |
|---------|-------------------|
| 1 | 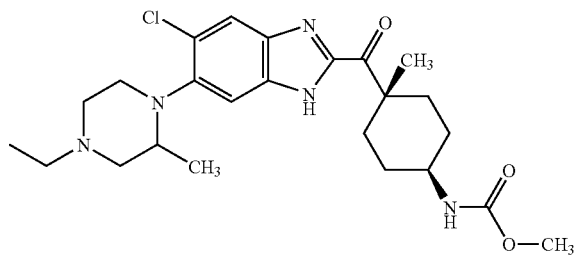 |
| 2 | 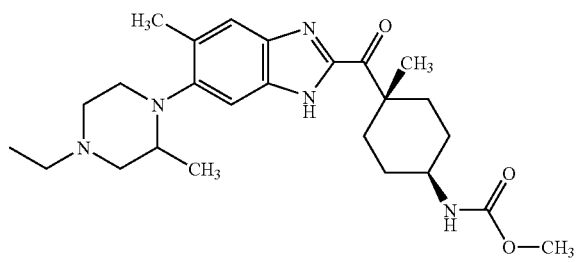 |
| 3 | 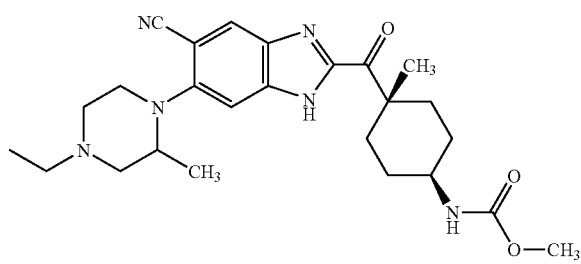 |
| 4 | 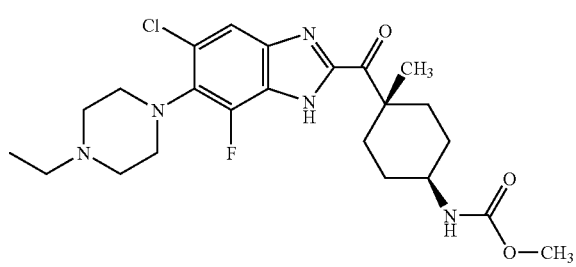 |
| 5 | 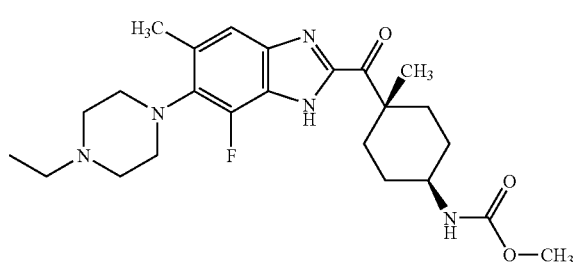 |
| 6 | 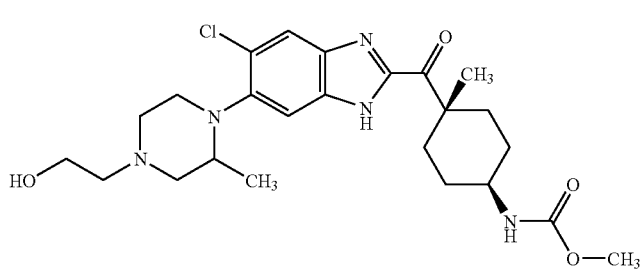 |

-continued
| Example | Structural formula |
|---|---|
| 7 | 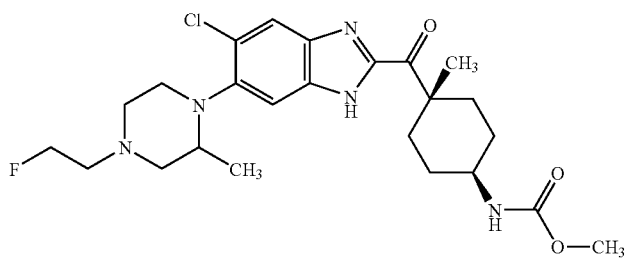 |
| 8 | 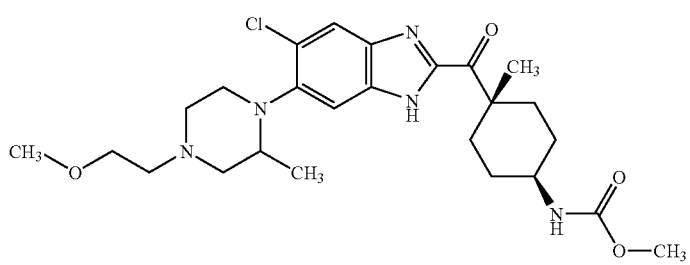 |
| 9 | 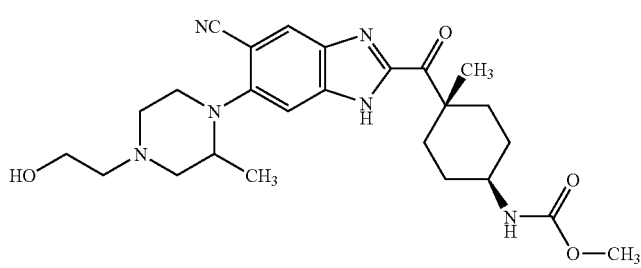 |
| 10 | 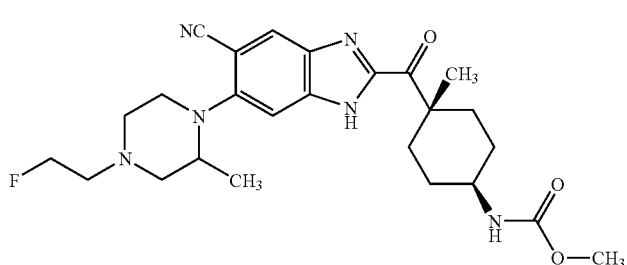 |
| 11 | 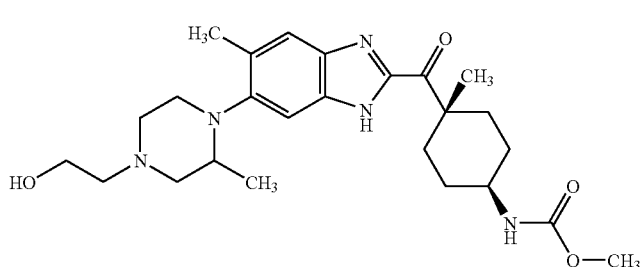 |
| 12 | 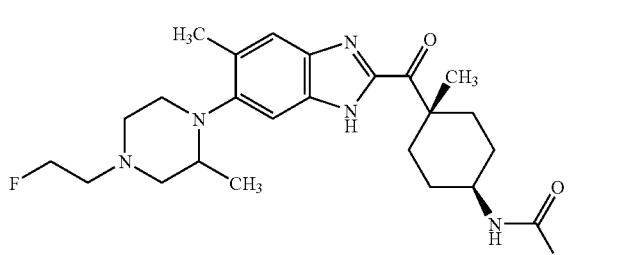 |

| Example | Structural formula |
|---------|-------------------|
| 13 | 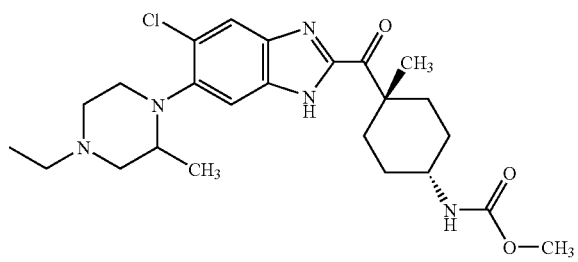 |
| 14 | 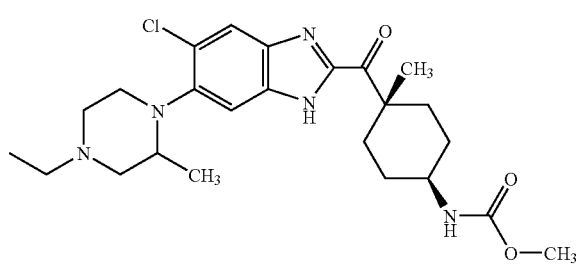 |
| 15 | 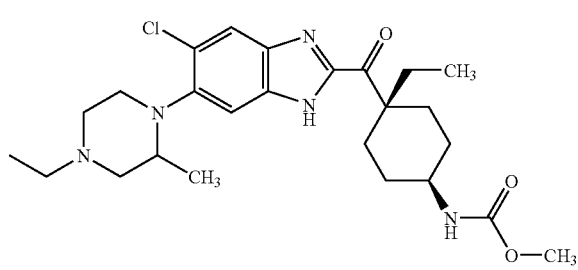 |
| 16 | 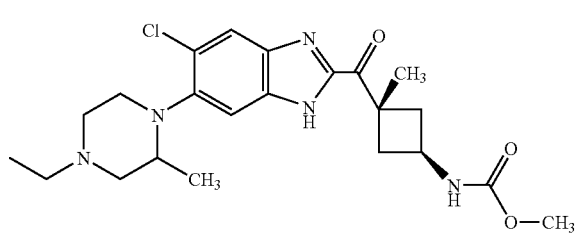 |
| 17 | 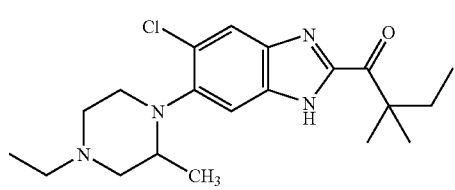 |
| 18 | 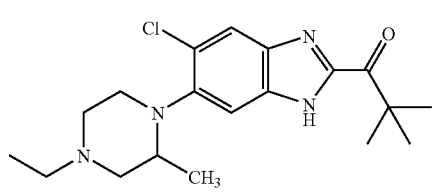 |
| 19 | 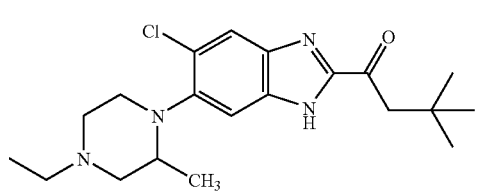 |

-continued
| Example | Structural formula |
|---|---|
| 20 | 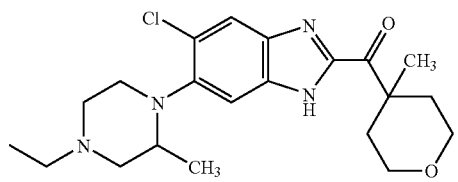 |
| 21 | 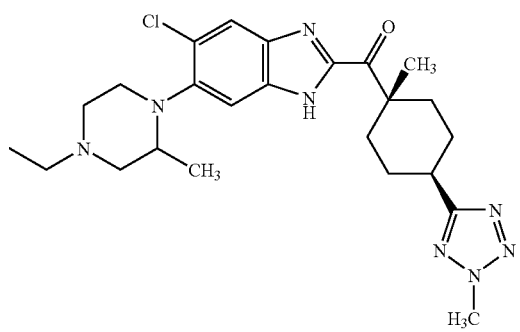 |
| 22 | 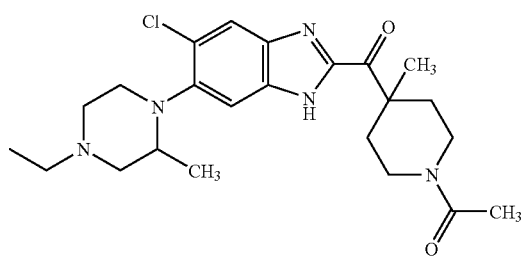 |
| 23 | 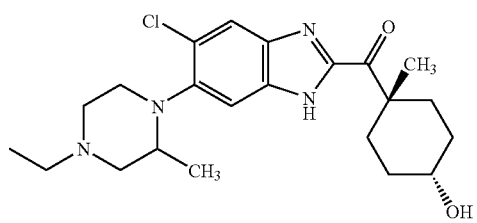 |
| 24 | 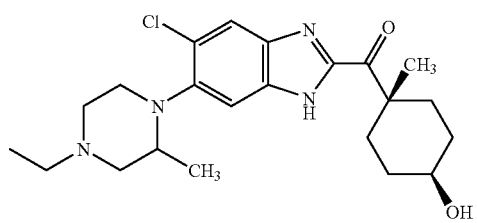 |
| 25 | 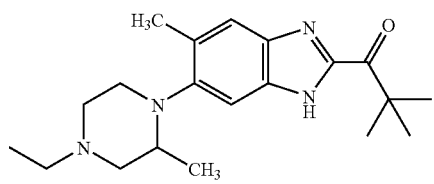 |

-continued
| Example | Structural formula |
|---|---|
| 26 | 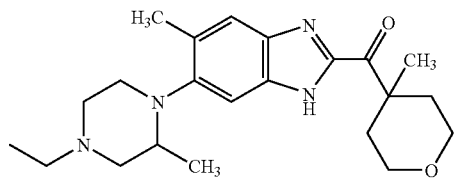 |
| 27 | 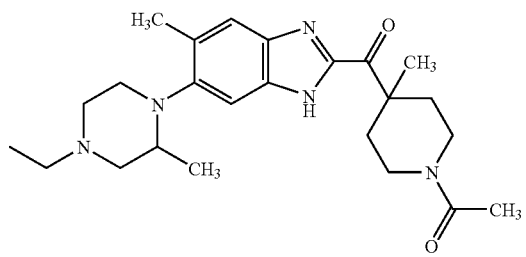 |
| 28 | 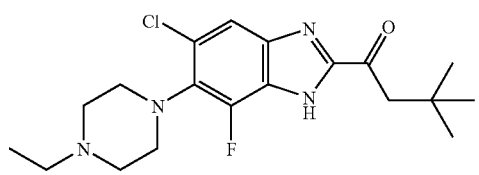 |
| 29 | 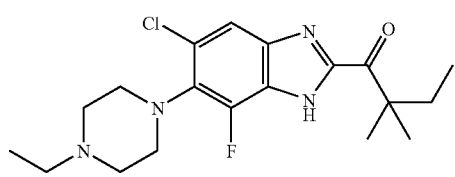 |
| 30 | 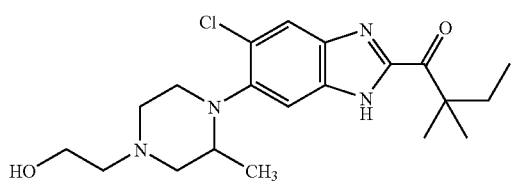 |
| 31 | 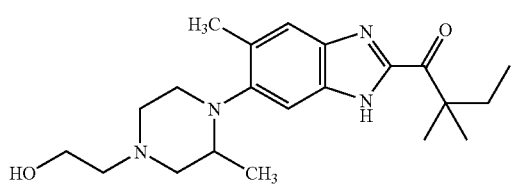 |
| 32 | 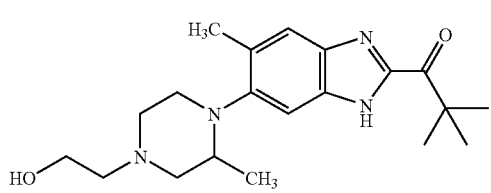 |
| 33 | 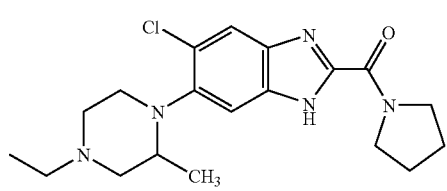 |

-continued
| Example | Structural formula |
|---|---|
| 34 | 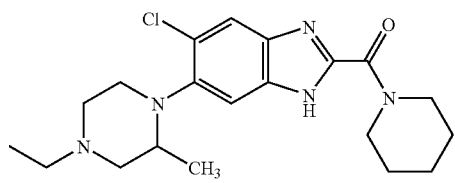 |
| 35 | 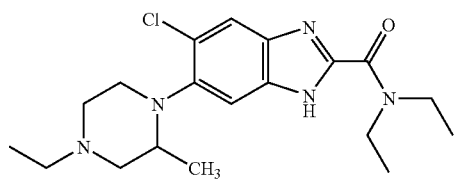 |
| 36 | 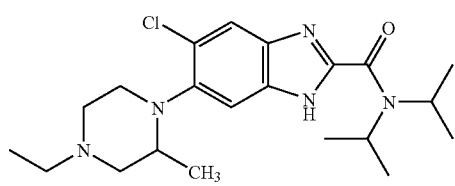 |
| 37 | 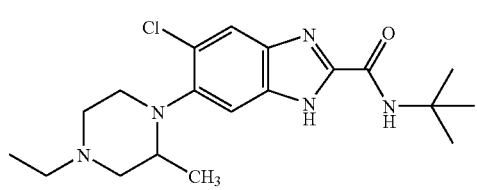 |
| 38 | 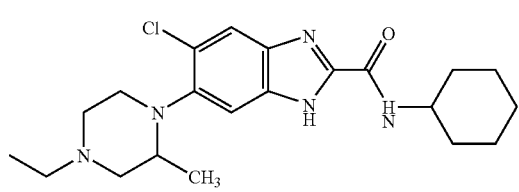 |
| 39 | 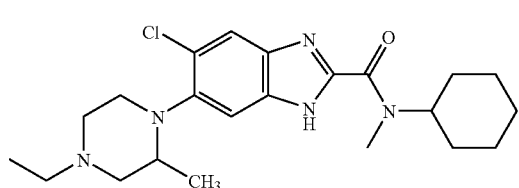 |
| 40 | 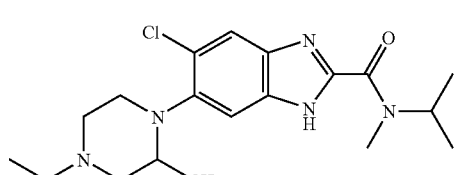 |
| 41 | 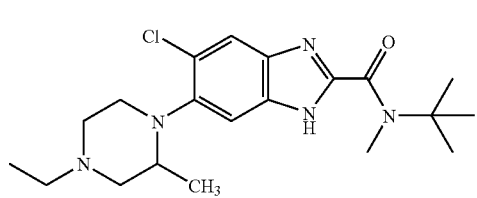 |

-continued
| Example | Structural formula |
|---------|-------------------|
| 42 | 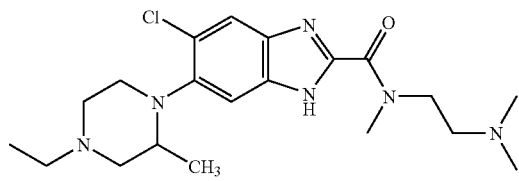 |
| 43 | 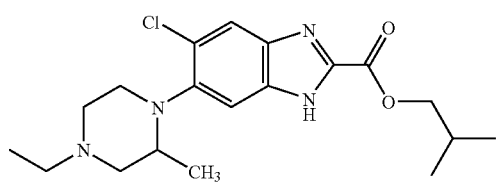 |
| 44 | 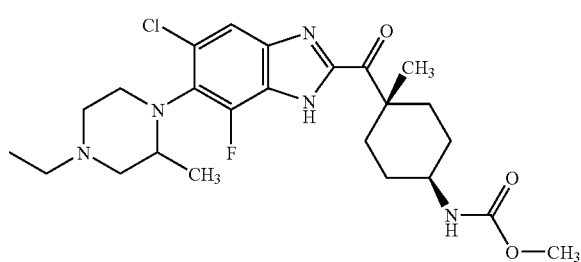 |
| 45 | 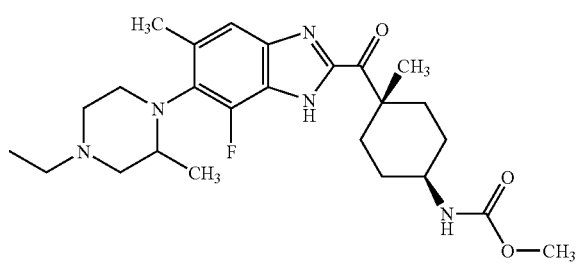 |
| 46 | 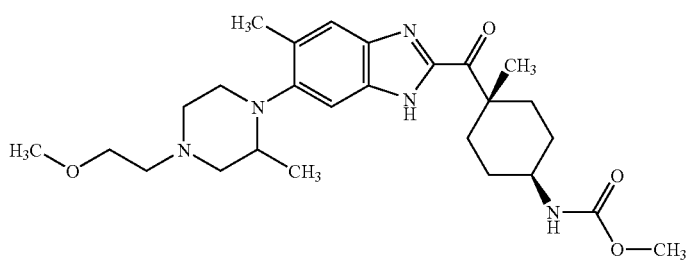 |
| 47 | 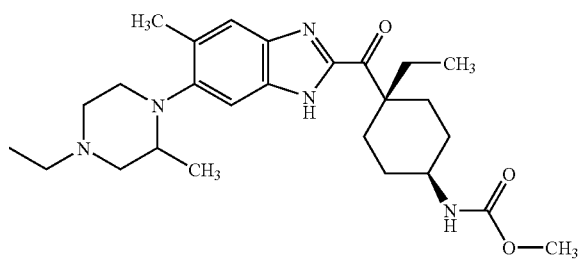 |

| Example | Structural formula |
|---------|--------------------|
| 48 | 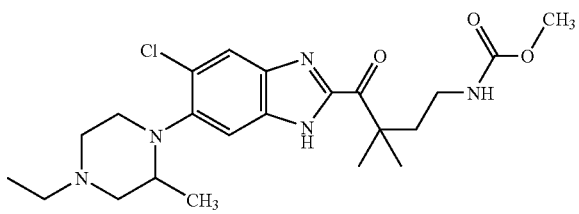 |
| 49 | 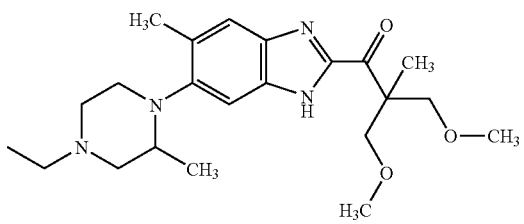 |
| 50 | 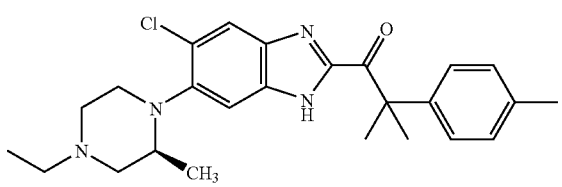 |
| 51 | 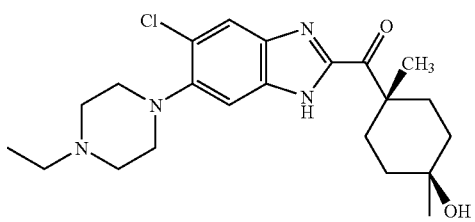 |
| 52 | 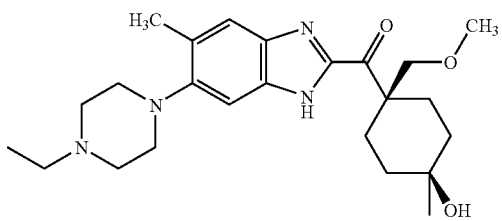 |
| 53 | 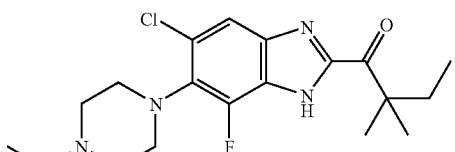 |

As the compounds represented by the general formula [I], the following are particularly preferred:

5-chloro-6-[4-ethyl-2-methylpiperazin-1-yl]-2-[(1,4-trans)-4-methoxycarbonylamino-1-methylcyclohexylcarbonyl]benzimidazole, 6-[4-ethyl-2-methylpiperazin-1-yl]-2-[(1,4-trans)-4-methoxycarbonylamino-1-methylcyclohexylcarbonyl]-5-methylbenzimidazole, 5-chloro-6-[4-(2-hydroxyethyl)-2-methylpiperazin-1-yl]-2-[(1,4-trans)-4-methoxycarbonylamino-1-methylcyclohexylcarbonyl]benzimidazole, 6-[4-(2-hydroxyethyl)-2-methylpiperazin-1-yl]-2-[(1,4-trans)-4-methoxycarbonylamino-1-methylcyclohexylcarbonyl]-5-methylbenzimidazole, 5-chloro-2-[(1,4-trans)-1-ethyl-4-(methoxycarbonylamino)cyclohexylcarbonyl]-6-[4-ethyl-2-methylpiperazin-1-yl]benzimidazole, 2-[(1,4-trans)-1-ethyl-4-(methoxycarbonylamino)cyclohexylcarbonyl]-6-[4-ethyl-2-methylpiperazin-1-yl]-5-methylbenzimidazole, 5-chloro-6-[4-ethyl-2-methylpiperazin-1-yl]-2-[(1,4-trans)-4-hydroxy-1-methylcyclohexylcarbonyl]benzimidazole, 2-(1-acetyl-4-methylpiperidinyl-4-carbonyl)-6-[4-ethyl-2-methylpiperazin-1-yl]-5-methylbenzimidazole, 6-[4-ethyl-2-methylpiperazin-1-yl]-5-methyl-2-(4-methyltetrahydropyranyl-4-carbonyl)benzimidazole 6-(4-ethyl-2-methylpiperazin-1-yl)-7-fluoro-2-[(1,4-trans)-4-methoxycarbonylamino-1-methylcyclohexylcarbonyl]-5-methylbenzimidazole, 5-chloro-2-[(1,4-trans)-1,4-dimethyl-4-hydroxycyclohexylcarbonyl]-6-(4-ethylpiperazin-1-yl)benzimidazole, 5-chloro-6-(4-ethylpiperazin-1-yl)-2-[(1,4-trans)-4-methoxycarbonylamino-1-methoxymethylcyclohexylcarbonyl]benzimidazole, 6-[(S)-1,4-diazabicyclo[4.3.0]nonan-4-yl]-2-[(1,4-trans)-4-hydroxy-1-methoxymethyl-4-methylcyclohexylcarbonyl]-5-methylbenzimidazole, 6-(4-ethylpiperazin-1-yl)-2-[(1,4-trans)-4-hydroxy-1-methoxymethyl-4-methylcyclohexylcarbonyl]-5-methylbenzimidazole.

A compound of the general formula [I] which is provided by the present invention can be prepared by a process comprising condensing a compound of a general formula,

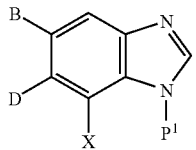

[in which
P$^1$ stands for a protective group;
B, D and X have the same significations as defined earlier, and where the group D contains hydroxyl or carboxyl, they may also be optionally protected]

with a compound of a general formula,

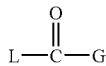

[in which
L stands for a leaving group;
G has the same signification as defined earlier]

in the presence of a base, and removing the protective group(s) where the formed compound contains protective group(s). More specifically, it can be prepared by conducting any of the following production processes 1–5, either singly or in suitable combination.

Production Process 1

This is a process for producing a compound of the general formula [I-1] according to the following reaction scheme 1:

Reaction Scheme 1

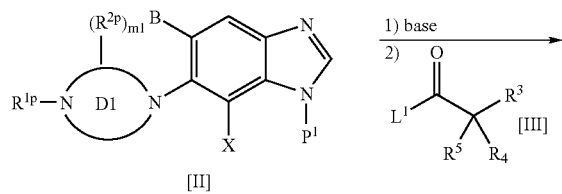

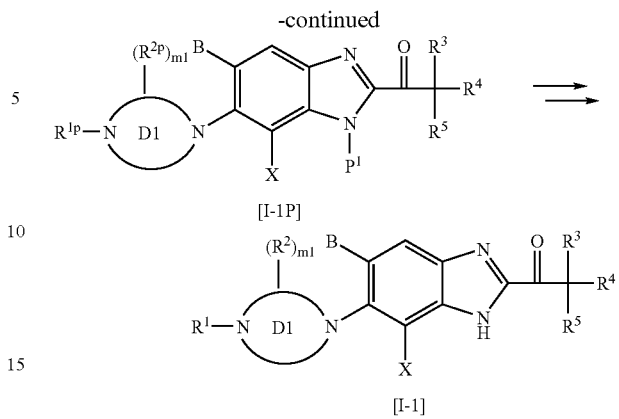

[in the formulae,
R$^{1P}$ has the same signification to R$^1$ or stands for a lower alkyl substituted with protected hydroxyl;
R$^{2P}$ has the same signification as R$^2$ or stands for a lower alkyl substituted with protected hydroxyl or protected carboxyl;
P$^1$ stands for an imidazolic amine-protective group;
L$^1$ stands for a leaving group such as hydrogen, halogen, —OR, —N(R), (OR) or the like, here R standing for lower alkyl;
B, X, R$^1$, R$^2$, R$^3$, R$^4$, R$^5$, m1 and D1 ring have the same significations as defined earlier].

Step 1-1: Production of a Compound of the General Formula [I-1P] from a Compound of the General Formula [II]

This step comprises, for example, mixing a compound of the general formula [II] with base in an organic solvent for a prescribed period, adding to the resulting solution a compound of the general formula [III] and conducting its condensation reaction with the compound of the general formula [II] to produce a compound of the formula [I-1P].

As the organic solvent, for example, ethers such as dimethyl ether, diethyl ether, tetrahydrofuran and 1,4-dioxane; benzene, toluene, hexane and the like can be used.

As the base, for example, n-butyl lithium, sec-butyl lithium, tert-butyl lithium, lithium diisopropylamide, lithium tetramethylpiperidide and the like can be used. Its use amount generally ranges 0.9–5.0 moles, preferably 1.1–3.0 moles, per mole of a compound of the general formula [II].

The temperature at which a compound of the general formula [II] is mixed with the base is normally within a range of –100° C.–0° C., preferably –78––10° C. Also as the mixing time, it can be around 10–120 minutes, preferably around 10–90 minutes.

To the resulting reaction liquid, successively a compound of the general formula [III] is added. The amount of the compound to be added can be within a range of 0.9–5.0 moles, preferably 1.1–3.0 moles, per mole of the compound of the general formula [II].

The temperature at which a compound of the general formula [III] reacts with a compound of the general formula [II] is normally within a range of –100° C.—room temperature, preferably –78–20° C. Also the adequate reaction time is around 1–20 hours, preferably around 1–3 hours.

After the reaction, a compound of the general formula [I-1P] can be isolated from the reaction liquid containing said compound where necessary, by treating the liquid by a purification means known per se such as liquid-liquid extraction, column chromatography or the like.

Step 1-2: Deprotection of the Compound of the General Formula [I-1P]

Where $R^{1P}$ and/or $R^{2P}$ in the resultant compound of the general formula [I-1P] are(is) protected, by removing said protective group(s) and also removing the protective group $P^1$, a compound of the general formula [I-1] is obtained. That is, where $R^1$ in the compound of the general formula [II] is a hydroxyl-substituted lower alkyl, or $R^2$ is a hydroxyl-substituted lower alkyl or carboxyl-substituted lower alkyl, each of said hydroxyl and/or carboxyl group(s) may be protected with suitable protective group(s) in advance of conducting the production step 1-1. Also the imidazolic amine can be protected with a protective group $P^1$. After a compound of the general formula [I-1P] is obtained according to the step 1-1, all of the protective groups are removed to provide the corresponding compound of the general formula [I-1]. Selection of respective protective groups, their introduction and removal can be effected by methods known per se, for example, by the methods as described in literature such as *Protective Groups in Organic Synthesis*, T. W. Green, John Wiley & Sons (1981). Protective Group $P^1$ is explained in the later described production process 3. Whereas, when $P^1$ is trimethylsilylethoxymethyl group, it can be readily removed with fluorine ion (tetrabutylammonium fluoride), hydrous trifluoroacetic acid or 2N-hydrochloric acid or the like.

As compounds of the general formula [III], for example, the following can be used.

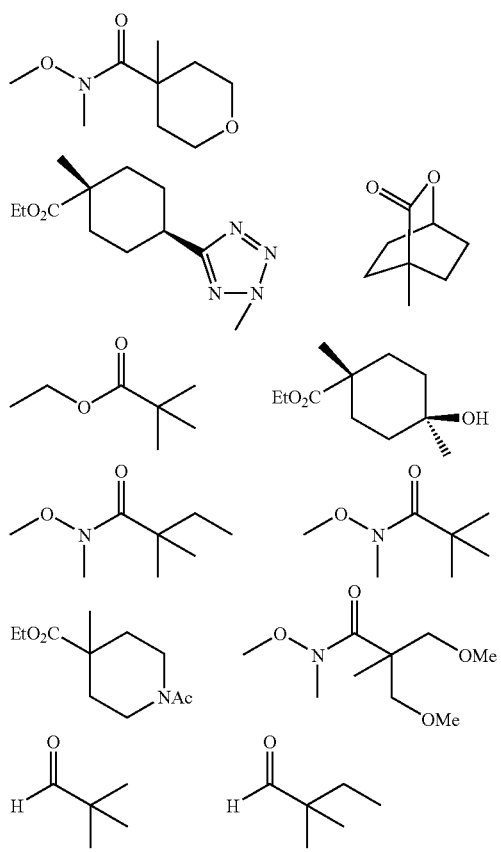

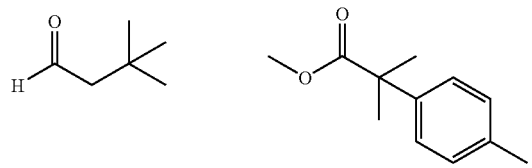

Whereas, where $L^1$ in a compound of the general formula [III] is hydrogen, a compound of the following general formula (C) is obtained through the production process 1, which compound can be converted to the corresponding compound of the general formula [I-1P] by oxidizing the hydroxyl group by the oxidizing method known per se using an oxidizing agent such as manganese dioxide, pyridium dichlorochromate or the like.

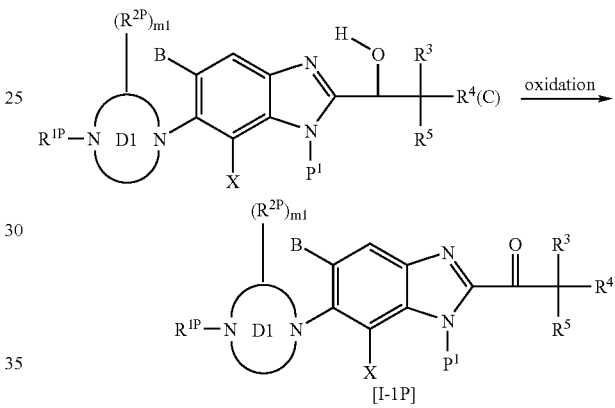

It is also possible to use, as a compound of the general formula [III], azide derivatives of a formula [III-1],

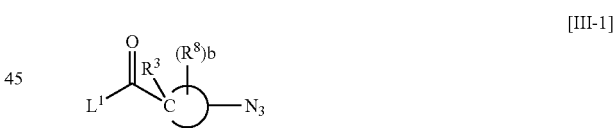

such as those of the following formulae:

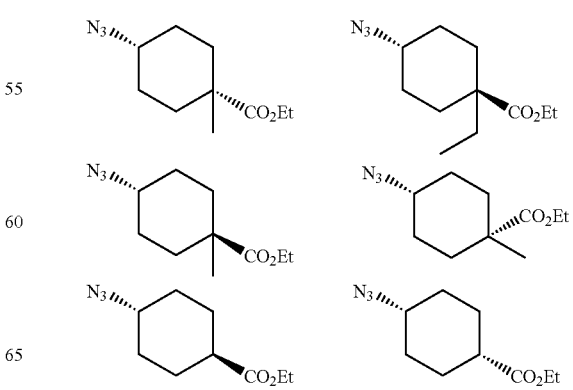

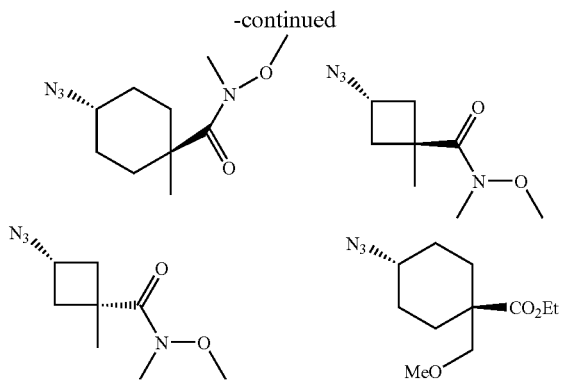

Upon conducting said production process 1-1 using such an azide derivative as the compound of the general formula [III], a compound of the following general formula (D) is obtained, which is convertible to the corresponding compound of the following general formula [I-1P$_P$] through reactions following the reaction scheme 1A as follows:

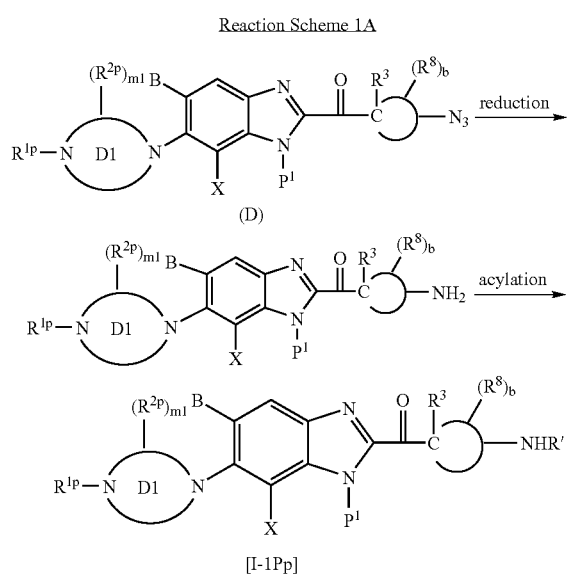

[in the formulae,
R' stands for a lower alkylcarbonyl, lower alkyloxycarbonyl or the like;
B, X, R$^{1P}$, R$^{2P}$, R$^3$, R$^8$, P$^1$, b, m1 and D1 ring are same as earlier defined].

That is, through the step of 1) condensing a compound having an azido group as represented by the general formula [III-1] with a compound of the general formula [II] to form an azide compound of the general formula (D), 2) reducing the azido site of said azide compound to form an amine derivative and 3) introducing a desired substituent group (R') into the formed amine by an acylation reaction, an intended compound of the general formula [I-1P$_P$] is derived.

Production Process 2

A compound of the general formula [I] in which a=1 can be obtained by conducting the production process 1 using a compound of a general formula [IIIb] in place of a compound of the general formula [III] according to the following reaction scheme 2:

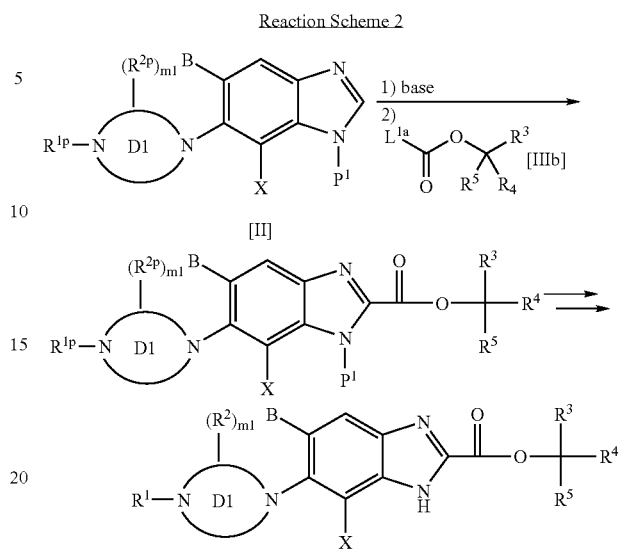

[in which
L$^{1a}$ stands for chlorine, cyano, lower alkyloxy or the like;
B, X, R$^{1P}$, R$^{2P}$, R$^1$, R$^2$, R$^3$, R$^4$, R$^5$, P$^1$, m1 and D1 ring signify the same as earlier defined].

This production process 2 is conducted in the manner following production process 1, using reaction conditions similar to those stated as to production process 1. Here, as P$^1$, pyrrolidinomethyl, dimethylaminomethyl, trimethylsilylethoxymethyl and the like are preferred.

Production Process 3

Those compounds represented by the general formula [II] which are used as the starting materials in the production processes 1 and 2 can be prepared by, for example, the following reaction scheme 3:

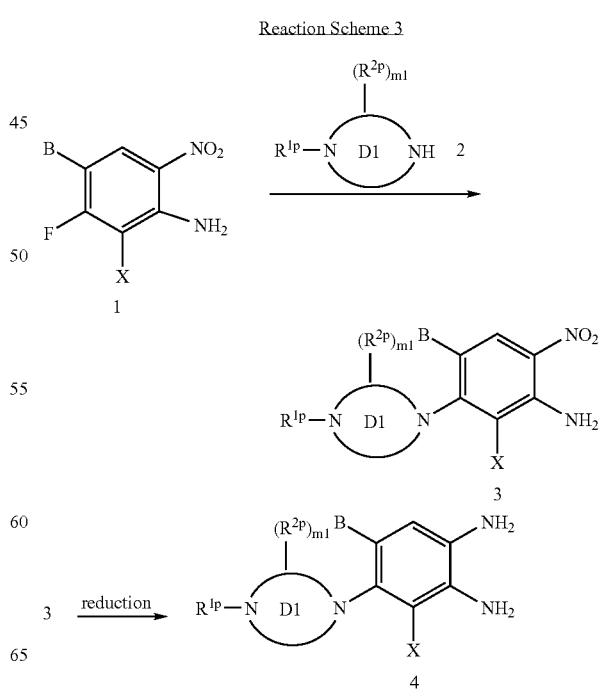

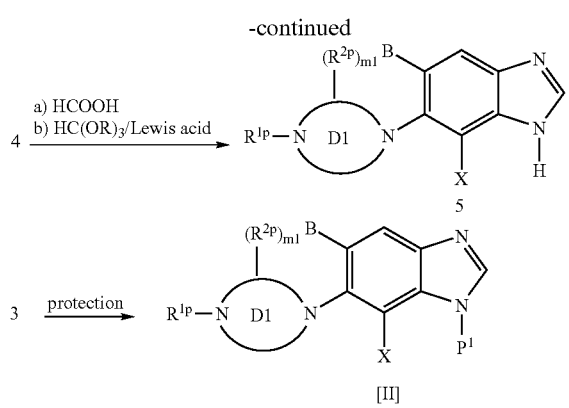

[in which B, X, $R^{1P}$, $R^{2P}$, $P^1$, m1 and D1 ring signify the same as earlier defined].

Step 3-1: Synthesis of Compound 3 from Compound 1

A compound 1 is reacted with a compound 2 to form a compound 3. This reaction can be conducted in a reaction solvent, in the presence of a basic compound. As the reaction solvent, for example, halogenated hydrocarbons such as methylene chloride, chloroform, dichloroethane, carbon tetrachloride and the like; aliphatic hydrocarbons such as n-heptane, n-hexane and the like; aromatic hydrocarbons such as benzene, toluene, xylene and the like; alcohols such as methanol, ethanol, isopropyl alcohol, cyclohexanol and the like; ethers such as diethyl ether, tetrahydrofuran, 1,4-dioxane, ethylene glycol dimethyl ether and the like; esters such as methyl acetate, ethyl acetate and the like; and aprotic solvents such as N,N-dimethylformamide, dimethylsulfoxide and the like can be used. Also as the basic compound, for example, potassium carbonate, sodium carbonate, lithium carbonate, triethylamine, diisopropylethylamine and the like can be used.

The use rate of the compound 2 generally can be within a range of 0.9–5.0 moles, preferably 0.95–3.0 moles, per mole of the compound 1. The use rate of the basic compound generally can be a range of 0.9–20 moles, preferably 0.95–5.0 moles, per mole of the compound 1.

Generally suitable reaction temperature is within a range of 0–200° C., preferably 60–180° C., and the reaction under such reaction conditions normally terminates in around 2–20 hours.

Step 3-2: Synthesis of Compound 4 from Compound 3

By reducing the nitro group in compound 3, the corresponding compound 4 having an amino group is formed. As the reduction methods, for example, 1) reduction with a combination of a transition metal such as iron, tin and the like with hydrochloric acid or ammonium chloride, 2) catalytic reduction, or 3) reduction using such reducing agent as sodium hydrosulfite, ammonium sulfide or the like, can be used.

In the reduction with the combination of a transition metal such as tin, iron or the like with hydrochloric acid or ammonium chloride (hereafter referred to as "transition metal reduction"), the transition metal can be used generally in an amount ranging 3–20 moles, preferably 10–15 moles, per mole of the compound 3. Also the amount of hydrochloric acid or ammonium chloride can generally be within a range of 2–10 moles, preferably 2.5–7 moles, per mole of the compound 3.

As the reaction solvent in the transition metal reduction, for example, inert solvents, e.g. alcohols such as methanol, ethanol or isopropyl alcohol; ethers such as dimethyl ether, diethyl ether, diisopropyl ether, dibutyl ether, dimethoxyethane, dioxane, tetrahydrofuran or diglyme; aliphatic hydrocarbons such as pentane, hexane, heptane or cyclohexane; or aromatic hydrocarbons such as benzene or toluene; and mixed solvents of these solvents with water can be used.

In the transition metal reduction, the reaction temperature is normally within a range of 0–150° C., preferably 60–130° C., and the reaction time may range from about 30 minutes to 5 hours.

Also as the catalyst useful in the occasion of converting compound 3 to compound 4 by catalytic reduction, for example, palladium on carbon, palladium-alumina, platinum oxide, ruthenium, rhodium, Raney-nickel and the like can be named. Such a catalyst can be used generally within a range of 0.1–2 wt parts, preferably 0.1–0.5 wt part, per 100 wt parts of compound 3.

Hydrogen pressure in the catalytic reduction can be 1–6 atmospheres, preferably 1–4 atmospheres. As the reaction solvent, any of those above-enumerated can be used.

The reaction temperature in the catalytic reduction normally ranges 0–100° C., preferably 10–40° C., and the reaction time can be about 1–8 hours.

Where compound 3 is converted to compound 4 using a reducing agent, the use amount of the reducing agent is generally within a range of 1–20 moles, preferably 1–10 moles, per mole of compound 3.

As the reaction solvent, those above-enumerated can be used, the reaction temperature is normally within a range of 0–150° C., preferably 20–120° C., and the reaction time can usually be about 1–24 hours.

Step 3-3: Synthesis of Compound 5 from Compound 4

This reaction can be conducted by, for example, the following method a) or b):
a) method of reacting compound 4 with formic acid, or
b) method of reacting compound 4 with trialkyl orthoformate [HC(OR)$_3$]/Lewis acid system.

a) Method of Reacting Formic Acid:

Compound 5 is obtained by reacting compound 4 with formic acid in an organic solvent or in the absence of solvent. The amount of formic acid is generally 0.9—a large molar excess, preferably 0.9—an amount sufficient to function as the solvent, per mole of the compound 4. The reaction temperature is normally within a range of 10–150° C., preferably 50–120° C., and the reaction time can be about 20 minutes–5 hours.

As the organic solvent, ethers such as diethyl ether, tetrahydrofuran, 1,4-dioxane and the like; chlorine-containing solvents such as methylene chloride, chloroform and the like, and toluene, benzene and the like can be used.

b) Reaction with Trialkyl Orthoformate/Lewis Acid System

Compound 4 can be converted to compound 5, by reacting it with trialkyl orthoformate in an organic solvent, in the presence of a Lewis acid such as p-toluenesulfonic acid, methanesulfonic acid, boron fluoride, hydrogen chloride, trifluoroacetic acid or the like.

As examples of trialkyl orthoformate, trimethyl orthoformate and triethyl orthoformate can be named, which is used generally within a range of 0.9–2.0 moles, preferably 0.95–1.2 moles, per mole of compound 4.

The amount of Lewis acid is not critical so long as it allows the reaction to progress, while generally a range of 0.01–1.0 mole, in particular, 0.01–0.2 mole, per mole of trialkyl orthoformate is preferred.

The reaction temperature can normally be within a range of 20–150° C., preferably 50–120° C. Also as the organic solvent, those exemplified in a) above can be used.

Step 3-4: Synthesis of Compound of the General Formula [II] from Compound 5

By protecting the imidazolic nitrogen atom of compound 5 with protective group $P^1$, compound of the general formula [II] is obtained. Here the selection of suitable protective group and its introduction can be effected by the methods known per se, for example, following the methods described in the literature earlier referred to, *Protective Groups in Organic Synthesis*.

As examples of specific protective group, 2-ethoxyethyl, trialkylsilyl, trimethylsilylethoxymethyl, pyrrolidinomethyl, dimethylaminomethyl, methoxymethyl and dialkyloxy groups are named, among which trimethylsilylethoxymethyl and pyrrolidinomethyl are preferred.

Production Process 3a

By using compound 2a in place of compound 2 in the production process 3, compound 5a can be obtained according to the following reaction scheme 3A. This compound 5a can be directly led to the corresponding compound of the general formula [I-1] through the steps which follow the production process 1.

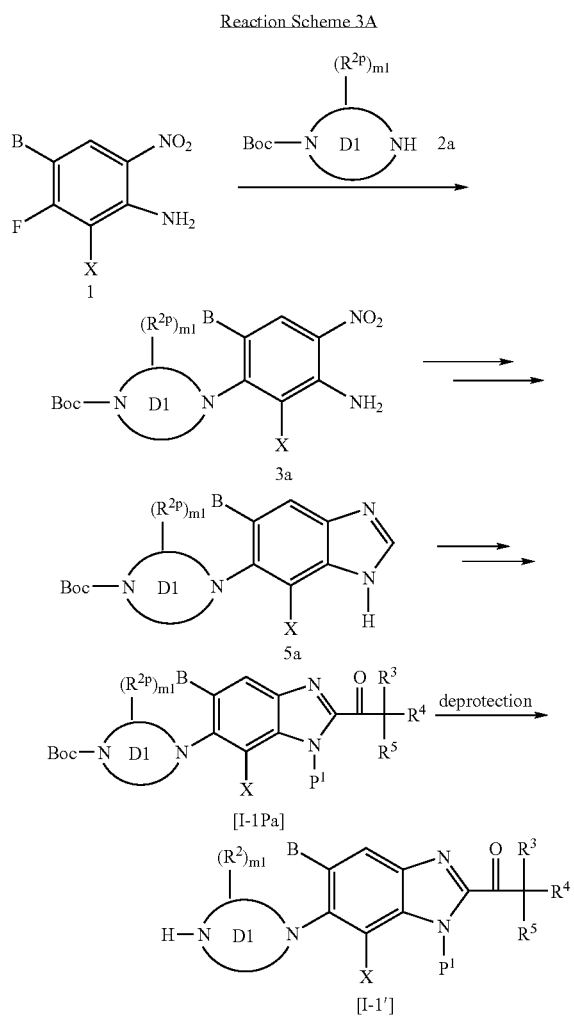

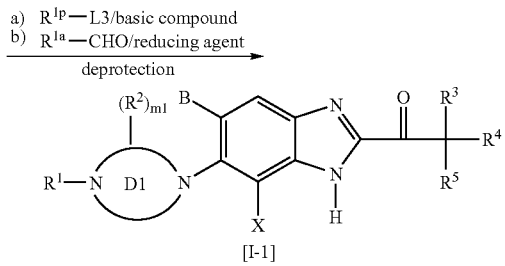

[In the formula,
$L^3$ stands for a leaving group;
$R^{1a}$ is a group forming $R^{1P}$ as $R^{1a}$—$CH_2$—;
B, X, $R^{1P}$, $R^{2P}$, $R^2$, $R^3$, $R^4$, $R^5$, $P^1$, m1 and D1 ring signify the same as earlier defined].

Compound 1 and compound 2a are reacted following the step 3-1 to provide a compound 3a. The compound 3a is treated similarly to the steps 3-3 and 3-4 to provide compound 5a. To this compound 5a as the starting material, the production process 1 is applied, to convert it to the corresponding compound of a general formula [I-1Pa]. Removing the Boc group from said compound of the general formula [I-1Pa], the corresponding compound of the general formula [I-1'] is obtained.

Successively, the compound of the general formula [I-1'] is subjected to:

a) an alkylation reaction with $R^{1P}$—$L^3$/basic compound, or b) a reductive alkylation reaction with $R^{1a}$—CHO/reducing agent, and finally the protective group $P^1$ is removed by the means known per se, for example, those described in the earlier cited literature, *Protective Group in Organic Synthesis*, to provide the corresponding compound of the general formula [I-1].

a) Alkylation Reaction with $R^{1P}$-$L^3$/Basic Compound:

As $L^3$ leaving groups, for example, halogen such as chlorine, bromine, iodine and the like; lower alkylsulfonyloxy such as methanesulfonyloxy, trifluoromethanesulfonyloxy and the like; arylsulfonyloxy such as p-toluenesulfonyloxy and the like; and 1-imidazolyl, 0-isourea and the like can be used.

In this reaction, a compound of the general formula [I-1'] and a compound of the formula $R^{1P}$-$L^3$ are reacted in a reaction solvent, in the presence of a basic compound and, where necessary, in the presence of potassium iodide, to provide the corresponding compound of the general formula [I-1].

As the reaction solvent, for example, halogenated hydrocarbons such as methylene chloride, chloroform, dichloroethane and carbon tetrachloride; hydrocarbons such as n-heptane and n-hexane; aromatic hydrocarbons such as benzene, toluene and xylene; ethers such as diethyl ether, tetrahydrofuran and 1,4-dioxane; esters such as methyl acetate and ethyl acetate; and aprotic solvents such as N,N-dimethylformamide and dimethylsulfoxide and the like can be used. As the basic compound, for example, potassium carbonate, sodium carbonate, sodium hydroxide, potassium hydroxide, triethylamine, diisopropylethylamine and the like can be used, in particular, potassium carbonate and sodium carbonate being preferred.

The compound of the formula $R^{1P}$-$L^3$ can be used in an amount generally within a range of 0.9–1.5 moles, preferably 1.05–1.2 moles, per mole of the compound of the general formula [I-1']. Furthermore, when potassium iodide is used, its amount may range about 0.1–1 mole, preferably about 0.1–0.5 mole, per mole of $R^{1P}$-$L^3$.

The basic compound can be used in an amount of generally within a range of 0.1–5 moles, preferably 0.1–2 moles, per mole of the compound of the general formula [I-1'].

The reaction temperature may normally be within a range of 0–150° C., preferably 40–90° C., and the reaction time can be about 1–24 hours.

b) Reductive Alkylation Reaction with $R^{1a}$—CHO/Reducing Agent:

A compound of the general formula [I-1'] and a compound of the formula $R^{1a}$—CHO are reacted in a reaction solvent, in the presence of a reducing agent (hereafter this reaction may be referred to as "reductive alkylation").

In this reaction, the aldehyde group in the formula $R^{1a}$—CHO reacts with the nitrogen atom in the compound of the general formula [I-1'] to form a carbon-nitrogen double bond (Schiff base). By hydrogenation reduction of this double bond, $R^{1P}$ is formed.

As the reaction solvent, for example, alcohols such as methanol, ethanol, propanol and 2-propanol; ethers such as diethyl ether, tetrahydrofuran and dioxane; halogenated hydrocarbons such as methylene chloride, chloroform and 1,2-dichloroethane; aromatic hydrocarbons such as benzene, toluene, chlorobenzene and xylene; aprotic solvents such as N,N-dimethylformamide and dimethylsulfoxide; and mixed solvents of these can be used.

The compound of the formula $R^{1a}$—CHO can be used generally within a range of 1–5 moles, preferably 1–3 moles, per mole of the compound of the general formula [I-1'].

As the reducing agent, for example, sodium cyanoborohydride, zinc cyanoborohydride, sodium triacetoxyborohydride and the like can be used. It is generally convenient to use the reducing agent in an amount within a range of 1–10 moles, in particular, 1–5 moles, per mole of the compound of the formula $R^{1a}$—CHO.

The reaction temperature is normally within a range of 0–150° C., preferably 20–100° C., and the reaction time can be around 5 minutes–48 hours, preferably 10 minutes–24 hours.

Production Process 4

Production process 4 can be illustrated by the following reaction scheme 4, and is effective for producing compounds of the general formula [I] in which D stands for the formula [D-2].

Reaction Scheme 4

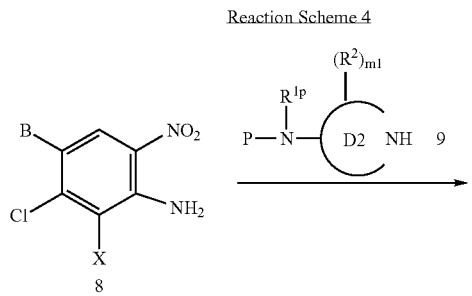

-continued

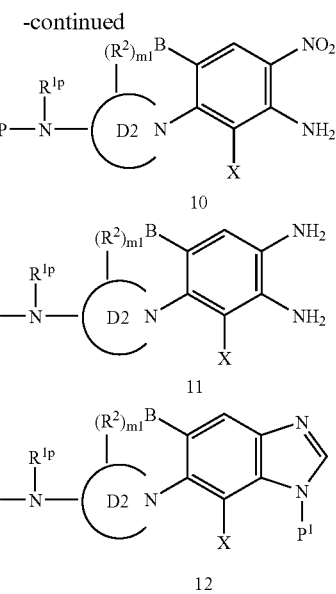

Step 4-1: Production of Compound 10 from Compound 8

A compound 8 and a compound 9 are condensed following the method as described in the step 3-1, to form a compound 10. As the reaction conditions and molar ratio in the reaction, those given for the step 3-1 are applicable.

Step 4-2: Production of Compound 11 from Compound 10

Reducing the nitro group of the compound 10 by hydrogenation following the method as described in the step 3-2, the corresponding diamine 11 is formed. As the reaction conditions and molar ratio in the reaction, those given for the step 3-2 are applicable.

Step 4-3: Production of Compound 12 from Compound 11

Compound 12 can be obtained by treating the diamine compound 11 following the methods as described in the steps 3-3 and 3-4. Compound 12 can be converted to a compound of the general formula [I] in which D stands for the formula [D-2] similarly to the Production process 1 according to the following reaction scheme 4A, by introducing a substituent at 2-position of the imidazole group following the method as described in the Production process 1.

Reaction Scheme 4A

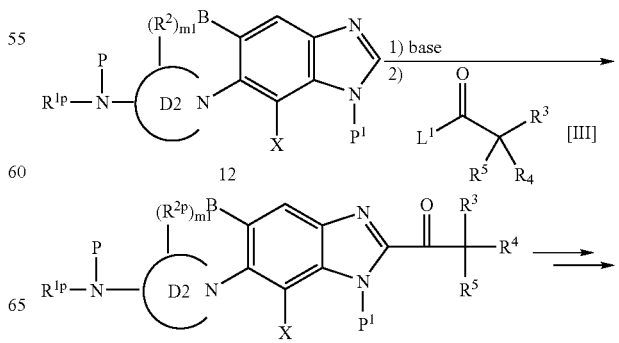

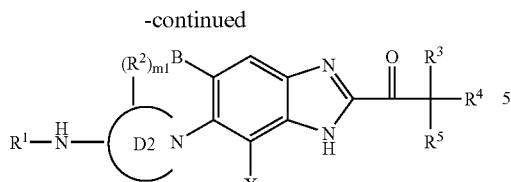

[in which

B, X, $R^{1p}$, $R^1$, $R^2$, $R^3$, $R^4$, $R^5$, P, $P^1$, m1 and D2 ring have the same significations as earlier defined].

As examples of the compound 9 in the reaction scheme 4, 4-(tert-butoxycarbonylamino)piperidine, 3-(tert-butoxycarbonylamino)pyrrolidine and 3-(tert-butoxycarbonylamino)piperidine can be named.

A compound of the general formula [I] in which a=1 can be obtained by conducting reactions following above production process 4 using a compound of the formula [III b] which is described in relation to the production process 2, in place of a compound of the formula [III] in above reaction scheme 4A.

Production Process 5

This is a process useful in the occasion of producing a compound of the general formula [I] in which D stands for the formula [D-3], according to the following reaction scheme 5:

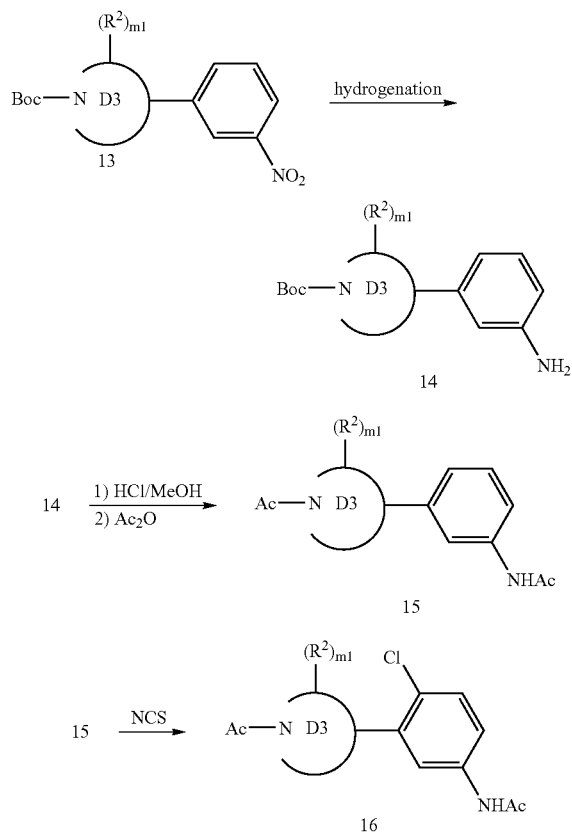

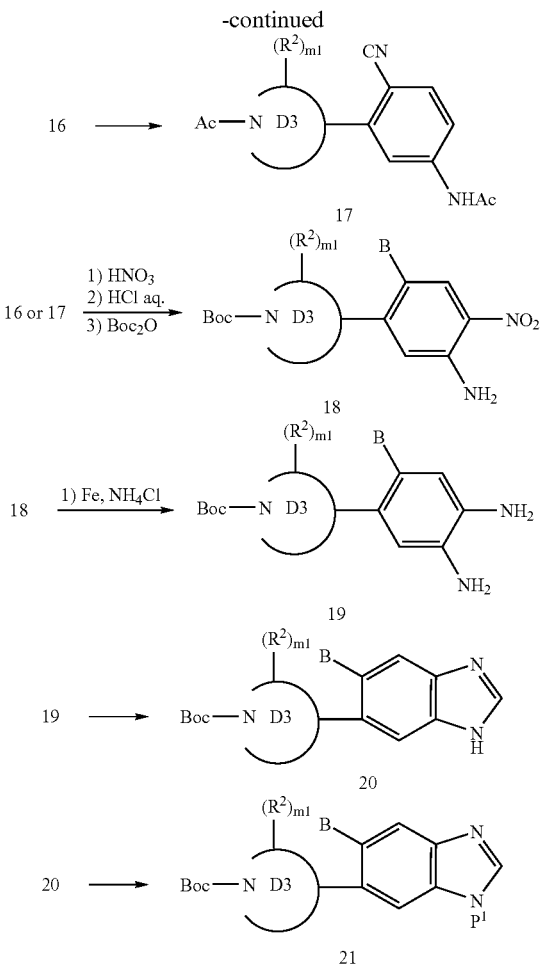

[in which

B, $R^2$, m1 and D3 ring have the same significations as earlier defined; and

Ac stands for acetyl].

Step 5-1: Production of Compound 14 from Compound 13

Through hydrogenation reduction of the nitro group in compound 13, compound 14 is formed. Here the hydrogenation reduction can be conducted by catalytic reduction using metal catalyst, and as the catalyst, palladium-on-carbon, Raney-nickel, platinum, rhodium-alumina catalysts and the like can be named. As the amount of such a catalyst, 5–50 wt parts, preferably 10–20 wt parts, of the catalyst is used per 100 wt parts of compound 13. The hydrogen pressure may range 1–6 atmospheres, preferably, 1–4 atmospheres.

As the reaction solvent, inert solvents, e.g., alcohols such as methanol, ethanol, isopropyl alcohol and the like; ethers such as dimethyl ether, diethyl ether, diisopropyl ether, dibutyl ether, dimethoxyethane, dioxane, tetrahydrofuran, diglyme and the like; and aliphatic hydrocarbons such as pentane, hexane, heptane, cyclohexane and the like; or mixed solvents of these solvents with water can be used.

The reaction temperature normally is within a range of 0–80° C., preferably 10–50° C., and the reaction time, normally 1 to 6 hours.

Step 5-2: Production of Compound 15 from Compound 14

Deprotecting the Boc group in compound 14 by, for example, treating the compound in a methanol solution of hydrogen chloride and acetylating the resulting amine, compound 15 is obtained. Said acetylation can be performed using an acetylating agent known per se, such as acetyl chloride, acetyl bromide, acetic anhydride and the like.

Where acetic anhydride is used, for example, 100 wt parts of the amine as obtained by the deprotection of compound 14 is dissolved in 50–500 wt parts of acetic anhydride and 50–3,000 wt parts of pyridine, preferably 100–300 wt parts of acetic anhydride and 100–1,000 wt parts of pyridine, and the solution is stirred at temperatures ranging 0–100° C., preferably 10–40° C., for 1–8 hours, to provide compound 15.

Step 5-3: Production of Compound 16 from Compound 15

Reacting compound 15 with N-chlorosuccinimide (NCS) in a reaction solvent, compound 16 is formed.

As the reaction solvent, halogenated hydrocarbon such as methylene chloride, chloroform, dichloroethane, carbon tetrachloride and the like; alcohols such as methanol, ethanol, isopropyl alcohol and the like; hydrocarbon solvents such as n-heptane, n-hexane and the like; ether solvents such as diethyl ether, tetrahydrofuran, 1,4-dioxane and the like; and aprotic solvents such as N,N-dimethylformamide, dimethylsulfoxide and the like can be named.

As the use rate of NCS, generally 1.0–5.0 moles, preferably 1.1–2.0 moles, of NCS is used per mole of compound 15. The reaction temperature normally is within a range of 50–200° C., preferably 70–120° C., and the reaction time can be around 0.5–2 hours.

Where N-bromosuccinimide is used in place of NCS, corresponding Br-substituted compound is obtained. Also by reacting compound 16 with sodium cyanide, potassium cyanide, copper cyanide or the like, compound 17 is obtained.

Step 5-4: Production of Compound 18 from Compound 16 (or 17)

Compound 16 (or 17) is converted to compound 18, by nitration thereof with a nitrating agent, hydrolyzing the acetyl group in the resulting compound and then t-butyloxycarbonylating the same.

Nitration of compound 16 (or 17) can be effected using nitrating agent known per se, and as such nitrating agent, fuming nitric acid can be named. The solvent to be used in the nitration reaction is preferably optionally selected according to individual nitrating agent used. For example, acetic acid, acetic anhydride, trifluoroacetic acid, sulfuric acid, dichloroethane, chloroform, carbon tetrachloride and the like can be named.

Use rate of fuming nitric acid can generally be 5.0–15.0 moles, preferably 3.0–8.0 moles, per mole of compound 16 (or 17). The reaction temperature is normally within a range of 0–150° C., preferably 0–50° C., and the reaction time is normally around 1–2 hours.

The acetyl group in the resulting compound is then hydrolyzed by a method known per se. In this reaction, normally hydrolysis using an acid is preferred, while that using a base is also possible. As useful base, for example, lithium hydroxide, sodium hydroxide, potassium hydroxide, sodium carbonate, potassium carbonate, sodium methoxide, sodium ethoxide and the like may be named. Also as examples of useful acid, hydrochloric acid, hydrobromic acid, sulfuric acid and the like can be named.

The solvent to be used in the hydrolysis can be optionally selected according to the hydrolyzing method, for example, from water, methanol, ethanol, propanol, tetrahydrofuran, dioxane, benzene, toluene, xylene, chlorobenzene, N,N-dimethylformamide, dimethylsulfoxide, formic acid, acetic acid, and mixed solvents of the foregoing.

The reaction temperature in the occasion of the hydrolysis is normally within a range of 0–150° C., preferably 50–130° C., and the reaction time can normally be 2–24 hours.

Successively the deacetylated amine is t-butyloxycarboxylated following, for example, the step 1-2 of the production process 1, by treating it with a t-butyloxycarbonylating agent, to provide compound 18.

Step 5-5: Production of Compound 20 from Compound 18

Compound 18 is hydrogenated and reduced following the method described in the step 3-2 of the production process 3, to be converted to compound 19. The compound 19 so obtained is subjected to a reaction following the method described in the step 3-3, to be converted to compound 20.

Furthermore, $P^1$ is introduced into the compound 20 following the method described in the step 3-4 and then $R^{1P}$ is introduced thereinto by the method following the production process 3A, to form compound 21, which is subjected to the following reaction scheme 5A, to provide the object compound. In the reaction scheme 5A, Boc group is represented as $R^{1P}$, which can be deprotected after the reaction, where necessary, by a means known per se.

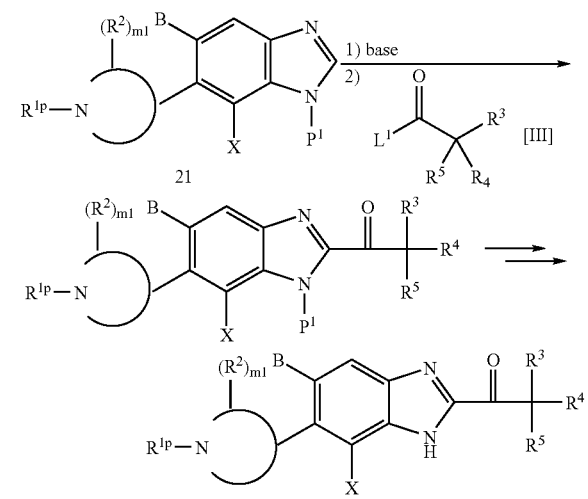

Reaction Scheme 5A

[in which
B, X, $R^{1P}$, $R^2$, $R^3$, $R^4$, $R^5$, $L^1$, $P^1$ and m1 have the same significations as earlier defined].

A compound of the general formula [I] in which a=1 can be obtained through reactions following the above production process 5, using a compound of the formula [IIIb] as described in the production process 2 in place of the compound of the formula [III] in above reaction scheme 5A.

Those compounds of the general formula [I] which are obtained by those heretofore described methods can be given improved purity through purification methods known per se. As the purification methods, column chromatography using an adsorbing resin such as silica gel or alumina, purification using ion-exchange resin, liquid chromatography, solvent extraction or recrystallization, reprecipitation and the like, and their combinations can be used.

Where the compounds of the present invention contain asymmetric carbon atoms in the substituent G or substituent D, optical isomers are present. In such a case, the compound can be used in the form of a racemic mixture, or each of the isomers may be isolated by optical resolution by such means as column chromatography using a column packed with an optically active filler.

The compounds of the present invention can be converted to pharmacologically acceptable salts by the means known per se. Conversely, conversion from salts to free compounds can also be easily conducted.

Utility of compounds of the invention as medicines is verified, for example, by the following pharmacological test examples.

Pharmacological Test Example 1 (Nociceptin Receptor Binding Inhibition Assay)

cDNA which codes a human nociceptin receptor gene was cloned into an expression vector pCR3 (Invitrogen) to prepare pCR3/ORL1. Next, pCR3/ORL1 was transfected in CHO cells using a transfectam (Nippongene) to obtain a stable expression strain (CHO/ORL1 cells) having resistance against 1 mg/ml G418. Membrane fractions were prepared from this stable expression strain to carry out a receptor binding assay.

The membrane of 11 μg, 50 pM [$^{125}$I] Tyr$^{14}$-Nociceptin (Amersham Pharmacia), 1 mg Wheatgerm agglutinin SPA beads (PVT based; Amersham Pharmacia) and each test compound were suspended in an NC buffer (50 mM Hepes, 10 mM sodium chloride, 1 mM magnesium chloride, 2.5 mM calcium chloride, 0.1% BSA, 0.025% bacitracin, pH 7.4) and incubated at 37° C. for 60 minutes, and then the radioactivity was determined. The binding activity to the nociceptin receptor was indicated by the 50% inhibition concentration (IC$_{50}$ value) of [$^{125}$I]Tyr$^{14}$-Nociceptin binding by each compound of the present invention. The results were as shown in Table 1.

TABLE 1

Nociceptin receptor binding inhibition action

| Compound | IC$_{50}$ value(nM) |
| --- | --- |
| Example 1(2S*) | 0.51 |
| Example 2(2S*) | 0.20 |
| Example 6(2S*) | 0.41 |
| Example 11(2S*) | 0.99 |
| Example 15(2S*) | 0.19 |
| Example 24(2S*) | 2.10 |
| Example 27(2S*) | 1.90 |
| Example 39(2S*) | 29.00 |
| Example 47(2S*) | 0.22 |
| Example 51 | 1.40 |
| Example 53 | 0.55 |

Pharmacological Test Example 2 (Antagonism Against Nociceptin-elicited G Protein Activation)

CHO cells which stably represented a nociceptin receptor ORL1 were used to investigate the action of each tested compound against nociceptin-elicited G protein activation. A membrane prepared from the CHO/ORL1 cells, 50 nM nociceptin, 200 pM GTPγ[$^{35}$S] (NEN), 1.5 mg Wheatgerm agglutinin SPA beads (Amersham Pharmacia) and each of the tested compounds were mixed in a GDP buffer (20 mM Hepes, 100 mM sodium chloride, 10 mM magnesium chloride, 1 mM EDTA, 5 μM GDP, pH 7.4) and incubated at 25° C. for 150 minutes, and then the radioactivity was determined. The antagonism against nociceptin-elicited G protein activation was shown by the 50% inhibition concentration (IC$_{50}$ value) of each tested compound against GTPγ[$^{35}$S] binding. The results were as shown in Table 2.

TABLE 2

Antagonism against nociceptin-elicited G protein activation

| Compound | IC$_{50}$ value(nM) |
| --- | --- |
| Example 1(2S*) | 0.82 |
| Example 2(2S*) | 0.63 |
| Example 6(2S*) | 0.92 |
| Example 11(2S*) | 0.63 |
| Example 15(2S*) | 0.42 |
| Example 24(2S*) | 2.80 |
| Example 27(2S*) | 1.50 |
| Example 39(2S*) | — |
| Example 47(2S*) | 0.36 |
| Example 51 | 0.65 |
| Example 53 | 1.00 |

Pharmacological Test Example 3: Antagonism Test

Using male ICR (CD-1) mice (weighing 20–40 g), antagonism to hypokinesis (suppression of motion) induced by nociceptin agonist was observed. That is, quantity of motion of each mouse in a 20 cm×30 cm×20 cm cage was measured with an infrared sensor. The test compound (1–10 mg/kg) as dissolved in either 0.5% methyl cellulose liquid or a solvent, and nociceptin agonist (0.3–1 mg/kg) were administered to the tested mice hypodermically and their quantity of motion in 60 minutes was measured. To the control group mice, the solvent only was administered. The evaluation was made by representing the kinetic quantity of the mice administered with the tested compounds by percent, where the difference in kinetic quantity between the nociceptin agonist-administered group and that of the solvent-administered control group during the measurement time was set to be 100%. In consequence, those tested compounds of the present invention were found to exhibit strong antagonism.

As can be understood from the results of above pharmacological tests, the compounds of the present invention antagonize to nociceptin receptors at very low concentration levels, and also exhibit antagonism to nociceptin-elicited G protein activation at very low concentration levels. Hence the compounds of the present invention are useful for pharmaceutical preparations for prophylaxis or treatment of various diseases attributable to nociceptin activities, for example, as an analgesic against diseases accompanied with pain such as cancerous pain, postoperative pain, migraine, gout, chronic rheumatism, chronic pain and neuralgia; a reliever against tolerance to narcotic analgesic represented by morphine; a reliever against dependence on narcotic analgesic represented by morphine or against addiction; an analgesic enhancer; an antiobestic or appetite suppressor; a treating or prophylactic agent for cognitive impairment and dementia/amnesia in aging, cerebrovascular diseases and Alzheimer's disease; an agent for treating developmental cognitive abnormality in attention deficit, hyperactivity disorder and learning disability; a remedy for schizophrenia; an agent for treating neurodegenerative diseases represented by Parkinsonism and chorea; an anti-depressant or treating agent for affective disorder; a treating or prophylactic agent for diabetes insipidus; a treating or prophylactic agent for polyuria; a remedy for hypotension, and the like.

In particular, the compounds of the present invention are especially useful as an analgesic; a reliever against tolerance to narcotic analgesic represented by morphine; a reliever against dependence on narcotic analgesic represented by morphine or against addiction; an analgesic enhancer; a treating or prophylactic agent for cognitive impairment and dementia/amnesia in aging, cerebrovascular diseases and Alzheimer's disease; an agent for treating developmental cognitive abnormality in attention deficit, hyperactivity disorder and learning disability; a remedy for schizophrenia and an agent for treating neurodegenerative diseases represented by Parkinsonism and chorea.

The compounds of the present invention can be administered orally or parenterally and, as formulated into preparation forms suitable for such administration routes, can be used as an analgesic against diseases accompanied with pain such as cancerous pain, postoperative pain, migraine, gout, chronic rheumatism, chronic pain and neuralgia; a reliever against tolerance to narcotic analgesic represented by morphine; a reliever against dependence on narcotic analgesic represented by morphine or against addiction; an analgesic enhancer; an antiobestic or appetite suppressor; a treating or prophylactic agent for cognitive impairment and dementia/amnesia in aging, cerebrovascular diseases and Alzheimer's disease; an agent for treating developmental cognitive abnormality in attention deficit, hyperactivity disorder and learning disability; a remedy for schizophrenia; an agent for treating neurodegenerative diseases represented by Parkinsonism and chorea; an anti-depressant or treating agent for affective disorder; a treating or prophylactic agent for diabetes insipidus; a treating or prophylactic agent for polyuria; a remedy for hypotension, and the like.

In actually using the compounds of the present invention clinically, they can be formulated into various preparation forms suitable for individual mode of administration, with pharmaceutically acceptable adjuvants. As the adjuvants, various additives customarily used in the field of medical preparations can be used, examples of which including gelatin, lactose, sucrose, titanium oxide, starch, crystalline cellulose, hydroxypropylmethyl cellulose, carboxymethyl cellulose, corn starch, microcrystalline wax, white petrolatum, magnesium aluminate metasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic anhydride, talc, vegetable oil, benzyl alcohol, acacia, propylene glycol, polyalkylene glycol, cyclodextrin or hydroxypropyl cyclodextrin and the like.

As the forms of preparations formulated as pharmaceutical compositions, solid preparations such as tablets, capsules, granules, powders and suppositories; liquid preparations such as syrups, elixirs and injections; and the like can be named. These preparations can be formulated according to conventional methods used in the field of pharmaceutics. Liquid preparations may be in a form which is dissolved or suspended in water or other suitable medium immediately prior to use. In particular, injections may be in the form of a solution or suspension in physiological saline solution or a glucose solution, to which a buffer agent, a preservative or the like may be added.

These preparations can contain a compound or compounds of the present invention at the ratios of 1–100 wt %, preferably 1–60 wt %, based on the total pharmaceutical composition. These preparations may further contain other therapeutically active compounds.

Where the compounds of the present invention are used as an analgesic against diseases accompanied with pain such as cancerous pain, postoperative pain, migraine, gout, chronic rheumatism, chronic pain and neuralgia; a reliever against tolerance to narcotic analgesic represented by morphine; a reliever against dependence on narcotic analgesic represented by morphine or against addiction; an analgesic enhancer; an antiobestic or appetite suppressor; a treating or preventive agent for cognitive impairment and dementia/amnesia in aging, cerebrovascular diseases and Alzheimer's disease; an agent for treating developmental cognitive abnormality in attention deficit, hyperactivity disorder and learning disability; a remedy for schizophrenia; an agent for treating neurodegenerative diseases represented by Parkinsonism and chorea; an anti-depressant or treating agent for affective disorder; a treating or prophylactic agent for diabetes insipidus; a treating or prophylactic agent for polyuria; a remedy for hypotension; their administration dosage or frequency can be varied depending on gender, age, body weight, degree of symptoms of individual patient and kind and extent of intended therapeutic effect. In general terms, for oral administration it is preferred to dispence 0.01–20 mg/kg per adult per day at a time or in a few times; and for parenteral administration, 0.002–10 mg/kg per day at a time or in a few times. Furthermore, it is also possible to administer them for prophylactic purpose, depending on symptoms of individual patients.

BEST MODES FOR CARRYING OUT THE INVENTION

Hereinafter the present invention is explained more specifically, referring to working Examples, it being understood that the invention is not limited to those working Examples. Unless otherwise specified, those various reagents used in the working Examples are the goods available on the market.

In the following, H-NMR values were measured, using tetramethylsilane as the reference material. Also the mass spectra were measured with Quattro II (MicroMass Co.), by electro spray ionizing method (ESI).

PRODUCTION EXAMPLE 1

Production of 4-chloro-5-fluoro-2-nitroaniline 1) 4-chloro-3-fluoroaniline

Into a solution of 96 ml of 3-fluoroaniline in 1000 ml of dichloromethane, 147 g of N-chlorosuccinimide was added at 0° C., and stirred for 12 hours at room temperature. After addition of water to the reaction solution, the system was extracted with chloroform. The chloroform layer was washed with saturated brine, dried on anhydrous magnesium sulfate and the solvent was distilled off. The resulting residue was separated and purified on silica gel column chromatography (hexane/ethyl acetate=5/1) to provide 21 g of the title compound.

2) 4-chloro-5-fluoro-2-nitroaniline

To 250 ml of trifluoroacetic anhydride, 21 g of the compound as obtained in 1) above and 15 g of potassium nitrate were added at 0° C. by the order stated, and stirred for 12 hours at room temperature. Ice water was added to the reaction solution, followed by extraction with ethyl acetate. The ethyl acetate layer was washed with saturated brine, dried on anhydrous magnesium sulfate and the solvent was distilled off. To a solution of the resulting residue in 400 ml of methanol, 200 ml of 7% aqueous potassium carbonate solution was added and stirred for 30 minutes at room temperature. Filtering the formed yellow solid off, 26.5 g of the title compound was obtained.

PRODUCTION EXAMPLE 2

Production of 5-chloro-6-(4-ethyl-2-methylpiperazin-1-yl)-1-[2-(trimethylsilyl)ethoxymethyl]benzimidazole and 6-chloro-5-(4-ethyl-2-methylpiperazin-1-yl)-1-[2-(trimethylsilyl)-ethoxymethyl] benzimidazole (1:1 Mixture)

1) 4-Chloro-5-(4-ethyl-2-methylpiperazin-1-yl)-2-nitroaniline

To a solution of 2.06 g of the compound obtained in Production Example 1 and 2.16 g of 1-ethyl-3-methylpiperazine in 30 ml of dimethylsulfoxide, 3.6 ml of diisopropylethylamine was added, and stirred for 12 hours at 140° C. Water was added to the reaction liquid, followed by extraction with ethyl acetate. The ethyl acetate layer was successively washed with water and saturated brine, dried on anhydrous magnesium sulfate, and the solvent was distilled off. The residue was separated and purified on silica gel column chromatography (chloroform/methanol=40/1) to provide 2.70 g of the title compounds.

2) 2-Amino-4-chloro-5-(4-ethyl-2-methylpiperazin-1-yl) aniline

In 60 ml of tetrahydrofuran, 2.70 g of the compound as obtained in 1) above, 2.40 g of ammonium chloride and 5.00 g of iron were suspended, and to which 20 ml of methanol and 20 ml of water were added, followed by 2 hours' stirring at 100° C. Cooling the reaction liquid to room temperature, saturated aqueous sodium hydrogencarbonate solution was added thereto, and the insoluble matter was filtered off with Celite. The filtrate was extracted with ethyl acetate, and the ethyl acetate layer was washed with saturated brine and dried on anhydrous magnesium sulfate. The solvent was distilled off to provide 2.28 g of the title compound.

3) 5-Chloro-6-(4-ethyl-2-methylpiperazin-1-yl) benzimidazole

Ten (10) ml of formic acid was added to 2.28 g of the compound as obtained in 2) above, followed by an hour's stirring at 100° C. The reaction liquid was condensed under reduced pressure. Saturated aqueous sodium hydrogencarbonate solution was added to the residue, followed by extraction with chloroform. The chloroform layer was dried on anhydrous magnesium sulfate, and the solvent was distilled off. The residue was separated and purified on silica gel column chromatography (chloroform/methanol/aqueous ammonia=100/10/1) to provide 2.75 g of the title compound.

4) 5-Chloro-6-(4-ethyl-2-methylpiperazin-1-yl)-1-[2-(trimethylsilyl)-ethoxymethyl]benzimidazole and 6-chloro-5-(4-ethyl-2-methylpiperazin-1-yl)-1-[2-(trimethylsilyl) ethoxymethyl]benzimidazole (1:1 Mixture)

To a solution of 1.50 g of the compound as obtained in 3) above in 20 ml of tetrahydrofuran, 323 mg of sodium hydride was added at 0° C., followed by 15 minutes' stirring at the same temperature. To the same solution 1.05 g of 2-(trimethylsilyl)ethoxymethyl chloride was added at 0° C., followed by 30 minutes' stirring at the same temperature. Ice was added to the reaction solution, followed by extraction with ethyl acetate. The ethyl acetate layer was washed with saturated brine, dried on anhydrous magnesium sulfate, and the solvent was distilled off. Separating and purifying the residue on silica gel column chromatography (chloroform/methanol=10/1) to provide 1.77 g of the title compounds as a position isomeric mixture.

EXAMPLE 1

Production of 5-chloro-6-[4-ethyl-(2S*)-2-methylpiperazin-1-yl]-2-[(1,4-trans)-4-methoxycarbonylamino-1-methylcyclohexylcarbonyl]benzimidazole and 5-chloro-6-[4-ethyl-(2R*)-2-methylpiperazin-1-yl]-2-[(1,4-trans)-4-methoxycarbonylamino-1-methylcyclohexylcarbonyl]benzimidazole 1) 2-[(1,4-trans)-4-azido-1-methylcyclohexylcarbonyl]-5-chloro-6-(4-ethyl-2-methylpiperazin-1-yl)-1-[2-(trimethylsilyl)ethoxymethyl]benzimidazole and 2-[(1,4-trans)-4-azido-1-methylcyclohexylcarbonyl]-6-chloro-5-(4-ethyl-2-methylpiperazin-1-yl)-1-[2-(trimethylsilyl)-ethoxymethyl]benzimidazole (1:1 Mixture)

To a solution of 2.53 g of the compounds as obtained in Production Example 2 in 20 ml of tetrahydrofuran, 6.2 ml of 1.5 N n-butyl lithium-hexane solution was added at −78° C. in a nitrogen atmosphere, followed by an hour's stirring at the same temperature. To the resulting solution a solution of 2.10 g of (1,4-trans)-4-azido-N,1-dimethyl-N-methoxycyclohexanecarboxamide [which compound was prepared from (1,4-trans)-4-azido-1-methylcyclohexanecarboxylic acid as described in WO 92/218463 and N,O-dimethylhydroxylamine hydrochloride, by the method taught by WO 99/70330] in 5 ml of tetrahydrofuran was added at −78° C., followed by 3 hour's stirring at room temperature. Saturated aqueous sodium hydrogencarbonate solution was added to the reaction liquid, which was then extracted with ethyl acetate. The ethyl acetate layer was washed with saturated brine, dried on anhydrous magnesium sulfate and the solvent was distilled off. The residue was separated and purified on silica gel column chromatography (chloroform/methanol=20/1) to provide 2.00 g of the title compounds as a position isomeric mixture.

2) 2-[(1,4-Trans)-4-amino-1-methylcyclohexylcarbonyl]-5-chloro-6-(4-ethyl-2-methylpiperazin-1-yl)-1-[2-(trimethylsilyl)ethoxymethyl]benzimidazole and 2-[(1,4-trans)-4-amino-1-methylcyclohexylcarbonyl]-6-chloro-5-(4-ethyl-2-methylpiperazin-1-yl)-1-[2-(trimethylsilyl)ethoxymethyl]benzimidazole (1:1 Mixture)

To a solution of 2.00 g of the compounds as obtained in 1) above in 20 ml of tetrahydrofuran, 2 ml of water and 1.62 g of triphenylphosphine were added, followed by 2 hours' heating under reflux. The reaction liquid was condensed under reduced pressure, and the residue was separated and purified on silica gel column chromatography (chloroform/methanol/aqueous ammonia=100/5/0.5) to provide 1.11 g of the title compounds as a position isomeric mixture.

3) 5-Chloro-6-(4-ethyl-2-methylpiperazin-1-yl)-2-[(1,4-trans)-4-methoxycarbonylamino-1-methylcyclohexylcarbonyl]-1-[2-(trimethylsilyl)ethoxymethyl]benzimidazole and 6-chloro-5-(4-ethyl-2-methylpiperazin-1-yl)-2-[(1,4-trans)-4-methoxycarbonylamino-1-methylcyclohexylcarbonyl]-1-[2-(trimethylsilyl)ethoxymethyl]benzimidazole (1:1 Mixture)

To a solution containing 1.11 g of the compounds as obtained in 2) above in 10 ml of chloroform, 1.10 g of potassium carbonate and 0.17 ml of methyl chloroformate were added, followed by an hour's stirring at room temperature. Water was added to the reaction solution which then was extracted with chloroform. The chloroform layer was washed with saturated brine, dried on anhydrous magnesium sulfate and the solvent was distilled off to provide 1.22 g of the title compounds as a position isomeric mixture.

4) 5-Chloro-6-[4-ethyl-(2S*)-2-methylpiperazin-1-yl] 2-[(1,4-trans)-4-methoxycarbonylamino-1-methylcyclohexylcarbonyl]benzimidazole and 5-chloro-6-[4-ethyl-(2R*)-2-methylpiperazin-1-yl]-2-[(1,4-trans)-4-methoxycarbonylamino-1-methylcyclohexylcarbonyl] benzimidazole To 10 ml of trifluoroacetic acid and 1 ml of water, 1.22 g of the compounds as obtained in 3) above were added, followed by 3 hours' stirring at room temperature. The reaction liquid was condensed under reduced pressure, and to the resulting residue 1N aqueous sodium hydroxide solution was added, followed by extraction with chloroform. The chloroform layer was washed with saturated brine, dried on anhydrous magnesium sulfate and the solvent was distilled off. The residue was separated and purified on silica gel column chromatography (chloroform/methanol/aqueous ammonia=100/5/0.5) to provide a racemic modification of the title compounds.

This racemic modification was optically resolved with an optically active column (Daicel Chemical Ind., Ltd., CHIRALPAK AD Column; 0.1% diethylamine, hexane/isopropyl alcohol=4/1). From the earlier fraction 408 mg of 5-chloro-6-(4-ethyl-2-methylpiperazin-1-yl)-2-[(1,4-trans)-4-methoxycarbonylamino-1-methylcyclohexylcarbonyl]benzimidazole (2S*-configuration) was obtained and from the later fraction, 408 mg of the same compound (2R*-configuration), both as pale yellow, oily substances. (Because the two were unidentified, the former is called 2S*-configuration and the other, 2R*-configuration, as also in the subsequent Examples.)

1HNMR(400 MHz, CDCl3)δ: 0.93(3H, d, J=6.4 Hz), 1.15(3H, t, J=6.8 Hz),1.45–2.30(12H, m),2.36–2.60(3H, m), 2.65–3.00(3H, m),3.12–3.90(6H, m),4.60–4.80(1H, m), 7.20–8.00(2H, m)

ESI-MS Found: m/z 476.2[M+H]+

PRODUCTION EXAMPLE 3

Production of 6-(4-ethyl-2-methylpiperazin-1-yl)-5-methyl-1-[2-(trimethylsilyl)ethoxymethyl]benzimidazole and 5-(4-ethyl-2-methylpiperazin-1-yl)-6-methyl-1-[2-(trimethylsilyl)-ethoxymethyl] benzimidazole (1:1 Mixture)

Reactions were conducted following the steps of Production Example 2, using 5-fluoro-4-methyl-2-nitroaniline (which was prepared by the method described in *J. Chem. Soc.*, 1949, S95–S99), in place of the compound obtained in Production Example 1, to provide the title compounds as a position isomeric mixture.

EXAMPLE 2

Production of 6-[4-ethyl-(2S*)-2-methylpiperazin-1-yl]-2-[(1,4-trans)-4-methoxycarbonylamino-1-methylcyclohexylcarbonyl]-5-methylbenzimidazole and 6-[4-ethyl-(2R*)-2-methylpiperazin-1-yl]-2-[(1,4-trans)-4-methoxycarbonylamino-1-methylcyclohexylcarbonyl]-5-methylbenzimidazole Reactions were conducted following the steps of Example 1, using the compounds as obtained in Production Example 3 in place of the compounds as obtained in Production Example 2, to provide the title compounds as a white powder.

1HNMR(300 MHz, CD3OD)δ: 0.82(3H, d, J=6.0 Hz), 1.58(3H, t, J=7.2 Hz),1.56(3H, s),1.56–1.68(2H, m), 1.72–1.86(2H, m),1.98–2.21(5H, m),2.28–2.39(1H, m),2.41 (3H, s), 2.46–2.57(2H, m),2.72–2.86(1H, m),2.89–3.05(3H, m), 3.24–3.34(1H, m),3.41–3.51(1H, m),3.62(3H, s),7.30–7.70(2H, m)

ESI-MS Found: m/z 456.3[M+H]+

PRODUCTION EXAMPLE 4

Production of 5-cyano-6-(4-ethyl-2-methylpiperazin-1-yl)-1-[2-(trimethylsilyl)ethoxymethyl]benzimidazole and 6-cyano-5-(4-ethyl-2-methylpiperazin-1-yl)-1-[2-(trimethylsilyl)ethoxymethyl] benzimidazole (1:1 Mixture)

Reactions were conducted following the steps of Production Example 2, using 4-cyano-5-fluoro-2-nitroaniline (which was prepared by the method described in *J. Med. Chem.*, 1994, 37, 467–475) in place of the compound obtained in Production Example 1, to provide the title compounds as a position isomeric mixture.

EXAMPLE 3

Production of 5-cyano-6-[4-ethyl-(2S*)-2-methylpiperazin-1-yl]-2-[(1,4-trans)-4-methoxycarbonylamino-1-methylcyclohexylcarbonyl]benzimidazole-fumaric acid salt and 5-cyano-6-[4-ethyl-(2R*)-2-methylpiperazin-1-yl]-2-[(1,4-trans)-4-methoxycarbonylamino-1-methylcyclohexylcarbonyl]benzimidazole-fumaric acid salt 1) 5-Cyano-6-[4-ethyl-(2S*)-2-methylpiperazin-1-yl]-2-[(1,4-trans)-4-methoxycarbonylamino-1-methylcyclohexylcarbonyl]benzimidazole and 5-cyano-6-[4-ethyl-(2R*)-2-methylpiperazin-1-yl]-2-[(1,4-trans)-4-methoxycarbonylamino-1-methylcyclohexylcarbonyl]benzimidazole Reactions were conducted following the steps of Example 1, using the compounds as obtained in production Example 4 in place of those obtained in Production Example 2, to provide the title compounds.

2) 5-Cyano-6-[4-ethyl-(2S*)-2-methylpiperazin-1-yl]-2-[(1,4-trans)-4-methoxycarbonylamino-1-methylcyclohexylcarbonyl]benzimidazole-fumaric acid salt and 5-cyano-6-[4-ethyl-(2R*)-2-methylpiperazin-1-yl]-2-[(1,4-trans)-4-methoxycarbonylamino-1-methylcyclohexylcarbonyl]benzimidazole-fumaric acid salt To a solution of 43 mg each of the compounds as obtained in 1) above in 1 ml of methanol, 11 mg of fumaric acid was added, and the solvent was distilled off under reduced pressure, to provide 52 mg of the title compound (2S*-configuration), and 53 mg of (2R*-configuration) of the same compound, both as pale yellow powder.

1HNMR(300 MHz, CD3OD)δ: 0.98(3H, d, J=6.0 Hz), 1.33(3H, t, J=7.3 Hz),1.52(3H, s),1.51–1.62(2H, m),1.70–1.81(2H, m), 1.96–2.20(4H, m),2.80–2.92(1H, m),3.19–3.20(2H, m), 3.13(2H, q, J=7.3 Hz),3.32–3.60(5H, m),3.58(3H, s),6.66(2H, s), 7.49–7.70(1H, br),8.02–8.16 (1H, br)

ESI-MS Found: m/z 467.3[M+H]+

PRODUCTION EXAMPLE 5

Production of 5-chloro-6-(4-ethylpiperazin-1-yl)-7-fluoro-1-[2-(trimethylsilyl)-ethoxymethyl]benzimidazole and 6-chloro-5-(4-ethylpiperazin-1-yl)-4-fluoro-1-[2-(trimethylsilyl)ethoxymethyl] benzimidazole (1:1 Mixture)

1) 4-Chloro-3-(4-ethylpiperazin-1-yl)-2-fluoro-6-nitroaniline

To a solution of 768 mg of 4-chloro-2,3-difluoro-6-nitroaniline (which was prepared by the method described in WO 98/56761 or WO 98/35977) and 629 mg of 1-ethylpiperazine in 5 ml of dimethylsulfoxide, 1.00 g of potassium carbonate was added, followed by 2 hours' stirring at 50° C. Water was added to the reaction liquid, followed by extraction with ethyl acetate. The ethyl acetate layer was washed with saturated brine, dried on anhydrous magnesium sulfate, and the solvent was distilled off. The residue was separated and purified on silica gel column chromatography (chloroform/methanol=50/1) to provide 704 mg of the title compounds.

2) 5-Chloro-6-(4-ethylpiperazin-1-yl)-7-fluoro-1-[2-(trimethylsilyl)-ethoxymethyl]benzimidazole and 6-chloro-5-(4-ethylpiperazin-1-yl)-4-fluoro-1-[2-(trimethylsilyl)ethoxymethyl]benzimidazole (1:1 Mixture)

Reactions were conducted following the steps 2),3) and 4) of Production Example 2, using the compounds as obtained in 1) above in place of the compound obtained in the step 1) of Production Example 2, to provide the title compounds as a position isomeric mixture.

EXAMPLE 4

Production of 5-chloro-6-(4-ethylpiperazin-1-yl)-7-fluoro-2-[(1,4-trans)-4-methoxycarbonylamino-1-methylcyclohexylcarbonyl]benzimidazole Reactions were conducted following the steps of Example 1, except that those as obtained in Production Example 5 were used in place of those as obtained in Production Example 2 and that the optical resolution step was not conducted, to provide the title compound as a white powder.

1HNMR(300 MHz, CDCl3+CD3OD)δ: 1.08(3H, t, J=7.3 Hz), 1.39–1.56(5H, m),1.70–1.85(2H, m),1.90–2.12(4H, m), 2.20–3.52(11H, m),3.59(3H, s),5.10–5.22(1H, m),7.28–7.67(1H, m)

ESI-MS Found: m/z 480.2[M+H]+

PRODUCTION EXAMPLE 6

Production of 6-(4-ethylpiperazin-1-yl)-7-fluoro-5-methyl-1-[2-(trimethylsilyl)ethoxymethyl]benzimidazole and 5-(4-ethylpiperazin-1-yl)-4-fluoro-6-methyl-1-[2-(trimethylsilyl)-ethoxymethyl] benzimidazole (1:1 Mixture)

1) 5-(4-Ethylpiperazin-1-yl)-4-methyl-2-nitroaniline

A reaction similar to the step 1) of Production Example 5 was conducted using 5-fluoro-4-methyl-2-nitroaniline in place of 4-chloro-2,3-difluoro-6-nitroaniline, to provide the title compound.

2) 3-(4-Ethylpiperazin-1-yl)-2-fluoro-4-methyl-6-nitroaniline

To a suspension of 4.20 g of the compound as obtained in 1) above and 2.70 g of sodium hydrogencarbonate in 84 ml of nitromethane, 11.3 g of N-fluoro-N'-(chloromethyl)triethylenediamine bis(tetrafluoroborate) was added, followed by 2 hours' stirring at 80° C. Saturated aqueous sodium hydrogencarbonate solution and water were added to the reaction liquid, followed by extraction with chloroform. The chloroform layer was successively washed with water and saturated brine, dried on anhydrous magnesium sulfate, and the solvent was distilled off. The residue was separated and purified on silica gel column chromatography (chloroform/methanol=10/1) to provide 1.33 g of the title compound.

3) 6-(4-Ethylpiperazin-1-yl)-7-fluoro-5-methyl-1-[2-(trimethylsilyl)-ethoxymethyl]benzimidazole and 5-(4-ethylpiperazin-1-yl)-4-fluoro-6-methyl-1-[2-(trimethylsilyl)ethoxymethyl]benzimidazole (1:1 Mixture)

Reactions were conducted following the steps 2),3) and 4) of Production Example 2, using the compounds as obtained in 2) above in place of the compound obtained in the step 1) of Production Example 2, to provide the title compounds as a position isomeric mixture.

EXAMPLE 5

Production of 6-(4-ethylpiperazin-1-yl)-7-fluoro-2-[(1,4-trans)-4-methoxycarbonylamino-1-methylcyclohexylcarbonyl]-5-methylbenzimidazole-fumaric acid salt Reactions were conducted following the steps of Example 1, except that the compounds as obtained in Production Example 6 were used in place of those as obtained in Production Example 2 and that no optical resolution step was conducted, to provide 6-(4-ethylpiperazin-1-yl)-7-fluoro-2-[(1,4-trans)-4-methoxycarbonylamino-1-methylcyclohexylcarbonyl]-5-methylbenzimidazole.

The same compound was converted to a fumaric acid salt thereof in the manner similar to step 2) of Example 3, and the title compound was obtained as a white solid.

1HNMR(400 MHz, CD3OD)δ: 1.40(3H, t, J=7.2 Hz), 1.44–1.83(7H, m),1.95–2.20(4H, m),2.45(3H, s),3.00–3.80 (14H, m), 6.70H(2H, s),7.21(1H, s)

ESI-MS Found: m/z 460.4[M+H]+

PRODUCTION EXAMPLE 7

Production of 6-(4-tert-butoxycarbonyl-2-methylpiperazin-1-yl)-5-chloro-1-[2-(trimethylsilyl) ethoxymethyl]benzimidazole and 5-(4-tert-butoxycarbonyl-2-methylpiperazin-1-yl)-6-chloro-1-[2-(trimethylsilyl)-ethoxymethyl]benzimidazole (1:1 Mixture)

1) 2-Amino-5-(4-tert-butoxycarbonyl-2-methylpiperazin-1-yl)-4-chloroaniline

Reactions were conducted following steps 1) and 2) of Production Example 2, using 1-tert-butoxycarbonyl-3-methylpiperazine in place of 1-ethyl-3-methylpiperazine, to provide the title compound.

2) 6-(4-Tert-butoxycarbonyl-2-methylpiperazin-1-yl)-5-chlorobenzimidazole

To a solution of 3.00 g of the compound as obtained in 1) above and 1.47 ml of triethyl orthoformate in 90 ml of toluene, 70 mg of p-toluenesulfonic acid monohydrate was added, followed by 2 hours' stirring at 120° C. Saturated aqueous sodium hydrogencarbonate solution was added to the reaction liquid which then was extracted with ethyl acetate. The ethyl acetate layer was dried on anhydrous magnesium sulfate and the solvent was distilled off. Separating and purifying the residue on silica gel column chromatography (ethyl acetate/hexane=3/1),2.46 g of the title compound was obtained.

3) 6-(4-Tert-butoxycarbonyl-2-methylpiperazin-1-yl)-5-chloro-1-[2-(trimethylsilyl)ethoxymethyl]benzimidazole and 5-(4-tert-butoxycarbonyl-2-methylpiperazin-1-yl)-6-chloro-1-[2-(trimethylsilyl)-ethoxymethyl]benzimidazole (1:1 Mixture)

The reaction was conducted following the step 4) of Production Example 2 using the compound as obtained in 2) above in place of the compound as obtained in step 3) of Production Example 2, to provide the title compounds as a position isomeric mixture.

EXAMPLE 6

Production of 5-chloro-6-[4-(2-hydroxyethyl)-(2S*)-2-methylpiperazin-1-yl]-2-[(1,4-trans)-4-methoxycarbonylamino-1-methylcyclohexylcarbonyl]benzimidazole-fumaric acid salt and 5-chloro-6-[4-(2-hydroxyethyl)-(2R*)-2-methylpiperazin-1-yl]-2-[(1, 4-trans)-4-methoxycarbonylamino-1-methylcyclohexylcarbonyl]benzimidazole-fumaric acid salt 1) 5-Chloro-2-[(1,4-trans)-4-methoxycarbonylamino-1-methylcyclohexylcarbonyl]-6-(2-methylpiperazin-1-yl) benzimidazole Reactions were conducted following the steps of Example 1, except that the compounds as obtained in Production Example 7 were used in place of those as obtained in Production Example 2 and that the optical resolution step was not conducted, to provide the title compound.

2) 6-{4-[2-(Tert-butyldimethylsilyloxy)ethyl]-2-methylpiperazin-1-yl}-5-chloro-2-[(1,4-trans)-4-methoxycarbonylamino-1-methylcyclohexylcarbonyl]benzimidazole To a solution of 99 mg of the compound as obtained in 1) above and 193 mg of (tert-butyldimethylsilyloxy)acetaldehyde in 4 ml of dimethylformamide, 93 mg of sodium triacetoxyborohydride was added, followed by 1.5 hours' stirring at room temperature. Saturated aqueous sodium hydrogencarbonate solution was added to the reaction liquid, followed by extraction with ethyl acetate. The ethyl acetate layer was successively washed with water and saturated brine, dried on anhydrous magnesium sulfate, and the solvent was distilled off. Separating and purifying the residue on silica gel column chromatography (ethyl acetate/hexane=2/1),76 mg of the title compound was obtained.

3) 5-Chloro-6-[4-(2-hydroxyethyl)-(2S*)-2-methylpiperazin-1-yl]-2-[(1,4-trans)-4-methoxycarbonylamino-1-methylcyclohexylcarbonyl]benzimidazole-fumaric acid salt and 5-chloro-6-[4-(2-hydroxyethyl)-(2R*)-2-methylpiperazin-1-yl]-2-[(1,4-trans)-4-methoxycarbonylamino-1-methylcyclohexylcarbonyl]benzimidazole-fumaric acid salt To 69 mg of the compound as obtained in 2) above, 1 ml of 10% hydrogen chloride in methanol solution was added, followed by 2.5 hours' stirring at room temperature. The reaction liquid was condensed under reduced pressure. Saturated aqueous sodium hydrogencarbonate solution was added to the residue, followed by extraction with chloroform. The chloroform layer was dried on anhydrous magnesium sulfate, and the solvent was distilled off. The residue was separated and purified by preparative thin-layer chromatography [Kieselgel™ 60F$_{254}$, Art 5744(Merck); chloroform/methanol/aqueous ammonia=100/10/1] to provide 5-chloro-6-[4-(2-hydroxyethyl)-2-methylpiperazin-1-yl]-2-[(1,4-trans)-4-methoxycarbonylamino-1-methylcyclohexylcarbonyl]benzimidazole as a racemic modification.

This racemic modification was optically resolved with an optically active column (Daicel Chemical Ind., Ltd., CHIRALPAK AD Column; 0.1% diethylamine, hexane/isopropyl alcohol=4/1). From the earlier fraction 5-chloro-6-(4-(2-hydroxyethyl)-2-methylpiperazin-1-yl)-2-[(1,4-trans)-4-methoxycarbonylamino-1-methylcyclohexylcarbonyl]benzimidazole (2S*-configuration) was obtained and from the later fraction, the same compound (2R*-configuration). (Because the two were unidentified, the former is called 2S*-configuration and the other, 2R*-configuration.) Each of the above compounds was converted to corresponding fumaric acid salt similarly to step 2) of Example 3, to provide 24 mg each of the title compounds as pale yellow solids.

1HNMR(300 MHz, CD3OD)δ: 0.98(3H, d, J=6 Hz),1.55 (3H, s), 1.62(2H, m),1.79(2H, m),2.01–2.22(4H, m),2.98 (1H, m), 3.13(1H, m),3.30(1H, m),3.47(1H, m),3.53–3.72 (3H, m),3.63(3H, s), 3.93(2H, t, J=5 Hz),7.61(1H, brs),7.78 (1H, brs)

ESI-MS Found: m/z 492.3[M+H]+

EXAMPLE 7

Production of 5-chloro-6-[4-(2-fluoroethyl)-(2S*)-2-methylpiperazin-1-yl]-2-[(1,4-trans)-4-methoxycarbonylamino-1-methylcyclohexylcarbonyl]benzimidazole-fumaric acid salt and 5-chloro-6-[4-(2-fluoroethyl)-(2R*)-2-methylpiperazin-1-yl]-2-[(1,4-trans)-4-methoxycarbonylamino-1-methylcyclohexylcarbonyl]benzimidazole-fumaric acid salt 1) 6-(4-Tert-butoxycarbonyl-2-methylpiperazin-1-yl)-5-chloro-2-[(1,4-trans)-4-methoxycarbonylamino-1-methylcyclohexylcarbonyl]-1-[2-(trimethylsilyl)ethoxymethyl]benzimidazole and 5-(4-tert-butoxycarbonyl-2-methylpiperazin-1-yl)-6-chloro-2-[(1,4-trans)-4-methoxycarbonylamino-1-methylcyclohexylcarbonyl]-1-[2-(trimethylsilyl)ethoxymethyl]benzimidazole (1:1 Mixture)

Reactions were conducted following the steps 1),2) and 3) of Example 1, using the compounds as obtained in Production Example 7 in place of those obtained in Production Example 2, to provide the title compounds as a position isomeric mixture.

2) 5-Chloro-2-[(1,4-trans)-4-methoxycarbonylamino-1-methylcyclohexylcarbonyl]-6-(2-methylpiperazin-1-yl)-1-[2-(trimethylsilyl)ethoxymethyl]benzimidazole and 6-chloro-2-[(1,4-trans)-4-methoxycarbonylamino-1-methylcyclohexylcarbonyl]-5-(2-methylpiperazin-1-yl)-1-[2-(trimethylsilyl)ethoxymethyl]benzimidazole (1:1 Mixture)

To 230 mg of the compound as obtained in 1) above, 6 ml of formic acid was added, followed by 2 hours' stirring at room temperature. The reaction liquid was condensed under reduced pressure, and saturated aqueous hydrogencarbonate solution was added to the residue, followed by extraction with chloroform. The chloroform layer was dried on anhydrous magnesium sulfate and the solvent was distilled off. The residue was separated and purified on silica gel column chromatography (chloroform/methanol=5/1) to provide 170 mg of the title compounds as a position isomeric mixture.

3) 5-Chloro-6-[4-(2-fluoroethyl)-2-methylpiperazin-1-yl]-2-[(1,4-trans)-4-methoxycarbonylamino-1-methylcyclohexylcarbonyl]-1-[2-(trimethylsilyl)ethoxymethyl]benzimidazole and 6-chloro-5-[4-(2-fluoroethyl)-2-methylpiperazin-1-yl]-2-[(1,4-trans)-4-methoxycarbonylamino-1-methylcyclohexylcarbonyl]-1-[2-(trimethylsilyl)ethoxymethyl]benzimidazole (1:1 Mixture)

To a solution of 81 mg of the compounds as obtained in 2) above and 39 mg of 2-fluoroethyl methanesulfonate (which was prepared from 2-fluoroethanol and methanesulfonyl chloride by a method known per se) in 3.5 ml of dimethylformamide, 39 mg of potassium carbonate was added, followed by 15 hours' stirring at 70° C. Water was added to the reaction liquid, followed by extraction with ethyl acetate. The ethyl acetate layer was successively washed with water and saturated brine, dried on anhydrous magnesium sulfate and the solvent was distilled off. The residue was separated and purified on silica gel column chromatography (ethyl acetate/hexane=2/1) to provide 63 mg of the title compounds as a position isomeric mixture.

4) 5-Chloro-6-[4-(2-fluoroethyl)-(2S*)-2-methylpiperazin-1-yl]-2-[(1,4-trans)-4-methoxycarbonylamino-1-methylcyclohexylcarbonyl]benzimidazole-fumaric acid salt and 5-chloro-6-[4-(2-fluoroethyl)-(2R*)-2-methylpiperazin-1-yl]-2-[(1,4-trans)-4-methoxycarbonylamino-1-methylcyclohexylcarbonyl]benzimidazole-fumaric acid salt To 3 ml of trifluoroacetic acid and 0.5 ml of water, 63 mg of the compounds as obtained in 3) above were added, followed by 5 hours' stirring at room temperature. The reaction liquid was condensed under reduced pressure, and to the residue 1N aqueous sodium hydroxide solution was added, followed by extraction with chloroform. The chloroform layer was washed with saturated brine, dried on anhydrous magnesium sulfate and the solvent was distilled off. The residue was separated and purified by preparative thin layer chromatography (Kieselgel™ 60F$_{254}$, Art. 5744 (Merck); chloroform/methanol/aqueous ammonia=100/10/1) to provide 5-chloro-6-[4-(2-fluoroethyl)-2-methylpiperazin-1-yl]-2-[(1,4-trans)-4-methoxycarbonylamino-1-methylcyclohexylcarbonyl]benzimidazole as a racemic modification.

This racemic modification was optically resolved with an optically active column (Daicel Co., Ltd., CHIRALPAK AD Column; 0.1% diethylamine, hexane/isopropyl alcohol=4/1), to obtain from the earlier fraction 5-chloro-6-[4-(2-fluoroethyl)-2-methylpiperazin-1-yl]-2-[(1,4-trans)-4-methoxycarbonylamino-1-methylcyclohexylcarbonyl]benzimidazole (2S*-configuration) and from the later fraction the same (2R*-configuration). (Because the two were unidentified, one of them was called 2S*-configuration and the other, 2R*-configuration, for convenience.)

Each of the above compounds were converted to its fumaric acid salt through a step similar to the step 2) of Example 3, and 24 mg each of the title compounds were obtained as pale yellow solids.

1HNMR(300 MHz, CD3OD)δ: 0.95(3H, d, J=6.2 Hz), 1.55(3H, s), 1.62(2H, m),1.77(2H, m),1.98–2.22(4H, m),2.77(1H, m),3.06(2H, m), 3.20–3.52(7H, m),3.52–3.68 (1H, m),3.62(3H, s),4.72(1H, t, J=4.5 Hz), 7.58(1H, brs), 7.76(1H, brs)

ESI-MS Found: m/z 494.4[M+H]+

EXAMPLE 8

Production of 5-chloro-2-[(1,4-trans)-4-methoxycarbonylamino-1-methylcyclohexylcarbonyl]-6-[4-(2-methoxyethyl)-(2S*)-2-methylpiperazin-1-yl]benzimidazole-fumaric acid salt and 5-chloro-2-[(1,4-trans)-4-methoxycarbonylamino-1-methylcyclohexylcarbonyl]-6-[4-(2-methoxyethyl)-(2R*)-2-methylpiperazin-1-yl]benzimidazole-fumaric acid salt Reactions were conducted following the steps 3) and 4) of Example 7 using bromoethyl methyl ether in place of 2-fluoroethyl methanesulfonate, to provide the title compounds as pale yellow solids.

1HNMR(300 MHz, CD3OD)δ: 0.96(3H, d, J=6.2 Hz), 1.55(3H, s), 1.62(2H, m),1.78(2H, m),2.01–2.23(4H, m),2, 90(1H, m), 3.02–3.34(5H, m),3.42(3H, s),3.42–3.69(4H, m),3.62(3H, s), 3.75(2H, t, J=5 Hz),7.59(1H, brs),7.77(1H, brs)

ESI-MS Found: m/z 506.2[M+H]+

PRODUCTION EXAMPLE 8

Production of 6-(4-tert-butoxycarbonyl-2-methylpiperazin-1-yl)-5-cyano-1-[2-(trimethylsilyl)ethoxymethyl]benzimidazole and 5-(4-tert-butoxycarbonyl-2-methylpiperazin-1-yl)-6-cyano-1-[2-(trimethylsilyl)ethoxymethyl]benzimidazole (1:1 Mixture)

Reactions were conducted following the steps of Production Example 7 using 4-cyano-5-fluoro-2-nitroaniline in place of the compound as obtained in Production Example 1, to provide the title compounds as a position isomeric mixture.

EXAMPLE 9

Production of 5-cyano-6-[4-(2-hydroxyethyl)-(2S*)-2-methylpiperazin-1-yl]-2-[(1,4-trans)-4-methoxycarbonylamino-1-methylcyclohexylcarbonyl]benzimidazole-fumaric Acid Salt and 5-cyano-6-[4-(2-hydroxyethyl)-(2R*)-2-methylpiperazin-1-yl]-2-[(1,4-trans)-4-methoxycarbonylamino-1-methylcyclohexylcarbonyl]benzimidazole-fumaric acid salt 1) 5-Cyano-2-[(1,4-trans)-4-methoxycarbonylamino-1-methylcyclohexylcarbonyl]-6-(2-methylpiperazin-1-yl) benzimidazole Reactions were conducted following the steps of Example 1 except that the compounds as obtained in Production Example 8 were used in place of those as obtained in Production Example 2 and that no optical resolution step was conducted, to provide the title compound.

2) 5-Cyano-6-[4-(2-hydroxyethyl)-(2S*)-2-methylpiperazin-1-yl]-2-[(1,4-trans)-4-methoxycarbonylamino-1-methylcyclohexylcarbonyl]benzimidazole-fumaric acid salt and 5-cyano-6-[4-(2-hydroxyethyl)-(2R*)-2-methylpiperazin-1-yl]-2-[(1,4-trans)-4-methoxycarbonylamino-1-methylcyclohexylcarbonyl]benzimidazole-fumaric acid salt Reactions were conducted following the steps 2) and 3) of Example 6 using the compound as obtained in 1) above in place of that as obtained in Example 6-1), to provide the title compounds as a pale yellow powder.

1HNMR(300 MHz, CD3OD)δ: 1.01(3H, d, J=6.2 Hz), 1.56(3H, s), 1.55–1.69(2H, m),1.72–1.86(2H, m),2.00–2.26 (4H, m), 2.82–2.95(1H, m),3.12–3.26(2H, m),3.18(2H, t, J=6.5 Hz), 3.31–3.63(5H, m),3.62(3H, s),3.88(2H, d, J=6.5 Hz),6.71(2H, s), 6.48–6.80(1H, brs),8.05–8.21(1H, br)

ESI-MS Found: m/z 483.3[M+H]+

EXAMPLE 10

Production of 5-cyano-6-[4-(2-fluoroethyl)-(2S*)-2-methylpiperazin-1-yl]-2-[(1,4-trans)-4-methoxycarbonylamino-1-methylcyclohexylcarbonyl]benzimidazole and 5-cyano-6-[4-(2-fluoroethyl)-(2R*)-2-methylpiperazin-1-yl]-2-[(1,4-trans)-4-methoxycarbonylamino-1-methylcyclohexylcarbonyl]benzimidazole 1) 6-(4-Tert-butoxycarbonyl-2-methylpiperazin-1-yl)-5-cyano-2-[(1,4-trans)-4-methoxycarbonylamino-1-methylcyclohexylcarbonyl]-1-[2-(trimethylsilyl)ethoxymethyl]benzimidazole and 5-(4-tert-butoxycarbonyl-2-methylpiperazin-1-yl)-6-cyano-2-[(1,4-trans)-4-methoxycarbonylamino-1-methylcyclohexylcarbonyl]-1-[2-(trimethylsilyl) ethoxymethyl]benzimidazole (1:1 Mixture)

Reactions were conducted following the steps 1),2) and 3) of Example 1, using the compounds as obtained in Production Example 8 in place of those as obtained in Production Example 2 to provide the title compounds as a position isomeric mixture.

2) 5-Cyano-6-[4-(2-fluoroethyl)-(2S*)-2-methylpiperazin-1-yl]-2-[(1,4-trans)-4-methoxycarbonylamino-1-methylcyclohexylcarbonyl]benzimidazole and 5-cyano-6-[4-(2-fluoroethyl)-(2R*)-2-methylpiperazin-1-yl]-2-[(1,4-trans)-4-methoxycarbonylamino-1-methylcyclohexylcarbonyl]benzimidazole Reactions were conducted following the steps 2),3) and 4) of Example 7 using the compounds obtained in 1) above in place of the compounds obtained in the step 1) of Example 7, to provide the title compounds as a pale yellow powder, without converting them to fumaric acid salts.

1HNMR(400 MHz, CDCl3)δ: 0.91(3H, d, J=6.2 Hz),1.52 (3H, s), 1.52–1.64(2H, m),1.70–1.82(2H, m),1.98–2.18(4H, m), 2.22–2.31(1H, m),2.51–2.99(6H, m),3.18–3.23(1H, m), 3.37–3.49(2H, m),3.58(3H, s),4.50(1H, t, J=5.0 Hz), 4.66 (1H, t, J=5.0 Hz),7.38–7.52(1H, br),8.02–8.20(1H, br)

ESI-MS Found: m/z 485.3[M+H]+

PRODUCTION EXAMPLE 9

Production of 6-(4-tert-butoxycarbonyl-2-methylpiperazin-1-yl)-5-methyl-1-[2-(trimethylsilyl)ethoxymethyl]benzimidazole and 5-(4-tert-butoxycarbonyl-2-methylpiperazin-1-yl)-6-methyl-1-[2-(trimethylsilyl)-ethoxymethyl]benzimidazole (1:1 Mixture)

1) 4-Bromo-5-(4-tert-butoxycarbonyl-2-methylpiperazin-1-yl)-2-nitroalinine

Reaction was conducted following the step 1) of Production Example 2, except that 4-bromo-5-fluoro-2-nitroaniline (which was prepared by the method described in WO 94/00124 or U.S. Pat. No. 5,514,680) was used in place of the compound as obtained in Production Example 1 and 1-tert-butoxycarbonyl-3-methylpiperazine was used instead of 1-ethyl-3-methylpiperazine, to provide the title compound.

2) 5-(4-Tert-butoxycarbonyl-2-methylpiperazin-1-yl)-4-methyl-2-nitroalinine

To a solution of 2.99 g of the compound as obtained in 1) above and 405 mg of tetrakis(triphenylphosphine) palladium in 72 ml of dimethylformamide, 2 ml of tetramethyltin was added, followed by 14 hours' stirring at 130° C. Water was added to the reaction liquid which then was extracted with ethyl acetate. The ethyl acetate layer was washed with saturated brine, dried on anhydrous magnesium sulfate and the solvent was distilled off. The residue was separated and purified on silica gel column chromatography (ethyl acetate/hexane=1/4) to provide 1.86 g of the title compound.

3) 2-Amino-5-(4-tert-butoxycarbonyl-2-methylpiperazin-1-yl)-4-methylaniline

Reaction was conducted following the step 2) of Production Example 2 using the compound as obtained in 2) above in place of the compound as obtained in the step 1) of Production Example 2, to provide the title compound.

4) 6-(4-Tert-butoxycarbonyl-2-methylpiperazin-1-yl)-5-methyl-1-[2-(trimethylsilyl)ethoxymethyl]benzimidazole and 5-(4-tert-butoxycarbonyl-2-methylpiperazin-1-yl)-6-methyl-1-[2-(trimethylsilyl)-ethoxymethyl]benzimidazole (1:1 Mixture)

Reactions were conducted following the steps 2) and 3) of Production Example 7 using the compound as obtained in 3) above in place of the compound as obtained in the step 1) of Production Example 7, to provide the title compounds as a position isomeric mixture.

EXAMPLE 11

Production of 6-[4-(2-hydroxyethyl)-(2S*)-2-methylpiperazin-1-yl]-2-[(1,4-trans)-4-methoxycarbonylamino-1-methylcyclohexylcarbonyl]-5-methylbenzimidazole-fumaric acid salt and 6-[4-(2-hydroxyethyl)-(2R*)-2-methylpiperazin-1-yl]-2-[(1,4-trans)-4-methoxycarbonylamino-1-methylcyclohexylcarbonyl]-5-methylbenzimidazole-fumaric acid salt 1) 2-[(1,4-Trans)-4-methoxycarbonylamino-1-methylcyclohexylcarbonyl]-5-methyl-6-(2-methylpiperazin-1-yl) benzimidazole Reactions were conducted following the steps of Example 1 except that the compounds as obtained in Production Example 9 were used in place of those as obtained in Production Example 2 and that the optical resolution step was not conducted, to provide the title compound.

2) 6-[4-(2-Hydroxyethyl)-(2S*)-2-methylpiperazin-1-yl]-2-[(1,4-trans)-4-methoxycarbonylamino-1-methylcyclohexylcarbonyl]-5-methylbenzimidazole-fumaric acid salt and 6-[4-(2-hydroxyethyl)-(2R*)-2-methylpiperazin-1-yl]-2-[(1,4-trans)-4-methoxycarbonylamino-1-methylcyclohexylcarbonyl]-5-methylbenzimidazole-fumaric acid salt Reactions were conducted following the steps 2) and 3) of Example 6 using the compound as obtained in 1) above in place of the compound as obtained in the step 1) of Example 6, to provide the title compounds as a pale brown powder.

1HNMR(300 MHz, CD3OD)δ: 0.92(3H, d, J=6.1 Hz), 1.50–1.90(4H, m),1.56(3H, s),1.95–2.30(4H, m),2.45(3H, s), 2.70–3.80(9H, m),3.63(3H, s),3.82–3.98(2H, m),6.70 (2H, s), 6.85–7.03(1H, m),7.30–7.85(2H, m)

ESI-MS Found: m/z 472.4[M+H]+

EXAMPLE 12

Production of 6-[4-(2-fluoroethyl)-(2S*)-2-methylpiperazin-1-yl]-2-[(1,4-trans)-4-methoxycarbonylamino-1-methylcyclohexylcarbonyl]-5-methylbenzimidazole-fumaric acid salt and 6-[4-(2-fluoroethyl)-(2R*)-2-methylpiperazin-1-yl]-2-[(1,4-trans)-4-methoxycarbonylamino-1-methylcyclohexylcarbonyl]-5-methylbenzimidazole-fumaric acid salt 1) 6-(4-Tert-butoxycarbonyl-2-methylpiperazin-1-yl)-2-[(1,4-trans)-4-methoxycarbonylamino-1-methylcyclohexylcarbonyl]-5-methyl-1-[2-(trimethylsilyl)ethoxymethyl]benzimidazole and 5-(4-tert-butoxycarbonyl-2-methylpiperazin-1-yl)-2-[(1,4-trans)-4-methoxycarbonylamino-1-methylcyclohexylcarbonyl]-6-methyl-1-[2-(trimethylsilyl)ethoxymethyl]benzimidazol (1:1 Mixture)

Reactions were conducted following the steps 1),2) and 3) of Example 1 using the compounds as obtained in Production Example 9 in place of those as obtained in Production Example 2, to provide the title compounds as a position isomeric mixture.

2) 6-[4-(2-Fluoroethyl)-(2S*)-2-methylpiperazin-1-yl]-2-[(1,4-trans)-4-methoxycarbonylamino-1-methylcyclohexylcarbonyl]-5-methylbenzimidazole-fumaric acid salt and 6-[4-(2-fluoroethyl)-(2R*)-2-methylpiperazin-1-yl]-2-[(1,4-trans)-4-methoxycarbonylamino-1-methylcyclohexyl carbonyl]-5-methylbenzimidazole-fumaric acid salt Reactions were conducted following the steps 2),3) and 4) of Example 7 using the compounds as obtained in 1) above in place of the compound as obtained in the step 1) of Example 7, to provide the title compounds as a pale brown powder.

1HNMR(300 MHz, CD3OD)δ: 0.88(3H, d, J=5.9 Hz), 1.17(2H, t, J=7.0 Hz),1.52–1.90(4H, m),1.56(3H, s), 1.97–2.30(4H, m),2.30–3.70(7H, m),2.44(3H, s),3.55–3.70 (2H, m), 3.63(3H, s),4.60–4.77(1H, m),6.72(2H, s),6.85–7.00(1H, m), 7.30–7.75(2H, m)

ESI-MS Found: m/z 474.4[M+H]+

EXAMPLE 13

Production of 5-chloro-6-[4-ethyl-(2S*)-2-methylpiperazin-1-yl]-2-[(1,4-cis)-4-methoxycarbonylamino-1-methylcyclohexylcarbonyl]benzimidazole and 5-chloro-6-[4-ethyl-(2R*)-2-methylpiperazin-1-yl]-2-[(1,4-cis)-4-methoxycarbonylamino-1-methylcyclohexylcarbonyl]benzimidazole Reactions were conducted following the steps of Example 1 using ethyl (1,4-cis)-4-azido-1-methylcyclohexanecarboxylate* in place of (1,4-trans)-4-azido-N,1-dimethyl-N-methoxycyclohexanecarboxamide to provide the title compounds as a colorless, oily substance.

1HNMR(200 MHz, CDCl3)δ: 0.95(3H, d, J=6.0 Hz), 1.16–1.30(4H, m),1.33(3H, t, J=7.3 Hz),1.39–1.68(4H, m), 1.81–2.42(3H, m),2.52–2.81(2H, m),2.82–3.32(6H, m), 3.41–3.78(5H, m),4.90–5.03(1H, m),7.31–7.96(2H, m)

ESI-MS Found: m/z 476.3[M+H]+

PRODUCTION EXAMPLE 10

Production of ethyl (1,4-cis)-4-azido-1-methylcyclohexanecarboxylate

To a solution of 156 mg of ethyl (1,4-trans)-4-methanesulfonyloxy-1-methylcyclohexanecarboxylate [which was prepared from ethyl (1,4-trans)-4-hydroxy-1-methylcyclohexanecarboxylate (prepared by the method described in *Chem. Pharm. Bull.*, 1984, 32, 2267–2278) and methanesulfonyl chloride by a hitherto known production method] in 2 ml of dimethylformamide, 86 mg of sodium azide was added, followed by 14 hours' stirring at 80° C. Water was added to the reaction liquid, followed by extraction with ethyl acetate. The ethyl acetate layer was washed with saturated brine, dried on anhydrous magnesium sulfate, and the solvent was distilled off. The residue was separated and purified on silica gel column chromatography (ethyl acetate/hexane=1/9) to provide 161 mg of the title compound.

Example 14

Production of 5-chloro-6-[4-ethyl-(2S*)-2-methylpiperazin-1-yl]-2-[(1,4-trans)-4-(methoxycarbonylamino)cyclohexylcarbonyl]benzimidazole and 5-chloro-6-[4-ethyl-(2R*)-2-methylpiperazin-1-yl]-2-[(1,4-trans)-4-(methoxycarbonylamino)cyclohexylcarbonyl]benzimidazole Reactions were conducted following the steps of Example 1 using ethyl (1,4-trans)-4-azidocyclohexanecarboxylate* in place of (1,4-trans)-4-azido-N,1-dimethyl-N-methoxycyclohexanecarboxamide, to provide the title compounds as a pale yellow, oily substance.

1HNMR(200 MHz, CDCl3)δ: 0.81–0.97(3H, m), 1.07–1.83(11H, m),2.01–2.22(4H, m),2.39–2.60(2H, m), 2.65–3.00(2H, m),3.32–3.72(3H, m),3.66(3H, s),4.49–4.61 (1H, m), 7.58–7.96(2H, m)

ESI-MS Found: m/z 462.3[M+H]+

PRODUCTION EXAMPLE 11

Production of ethyl (1,4-trans)-4-azidocyclohexanecarboxylate

Reactions were conducted following the steps of Production Example 10, using ethyl (1,4-cis)-4-(methanesulfonyloxy)cyclohexanecarboxylate [which was prepared from ethyl (1,4-cis)-4-hydroxycyclohexanecarboxylate (prepared by the method as described in *Tetrahedron Lett.*, 1994, 35, 5915–5918) and methanesulfonyl chloride by the known production method] in place of ethyl (1,4-trans)-4-methanesulfonyloxy-1-methylcyclohexanecarboxylate, to provide the title compound.

EXAMPLE 15

Production of 5-chloro-2-[(1,4-trans)-1-ethyl-4-(methoxycarbonylamino)-cyclohexylcarbonyl]-6-[4-ethyl-(2S*)-2-methylpiperazin-1-yl]benzimidazole-fumaric acid salt and 5-chloro-2-[(1,4-trans)-1-ethyl-4-(methoxycarbonylamino)-cyclohexylcarbonyl]-6-[4-ethyl-(2R*)-2-methylpiperazin-1-yl]benzimidazole-fumaric acid salt Reactions were conducted following the steps of Example 1 using ethyl (1,4-trans)-4-azido-1-ethylcyclohexanecarboxylate* in place of (1,4-trans)-4-azido-N,1-dimethyl-N-methoxycyclohexanecarboxamide, to provide (2S*-configuration) and (2R*-configuration) of 5-chloro-2-[(1,4-trans)-1-ethyl-4-(methoxycarbonylamino)-cyclohexylcarbonyl]-6-(4-ethyl-2-methylpiperazin-1-yl) benzmidazole. Each of said compounds was converted to the corresponding fumaric acid salt through a step similar to 2) of Example 3, and the title compounds were obtained as a pale yellow powder.

1HNMR(300 MHz, CD3OD)δ: 0.69(3H, t, J=7.3 Hz), 0.99(3H, d, J=6.0 Hz),1.39(3H, t, J=7.3 Hz),1.50–1.80(4H, m), 1.98–2.37(6H, m),2.86–3.18(2H, m),3.18–3.37(4H, m), 3.40–3.71(7H, m),6.71(2H, s),6.90–7.88(2H, m)
ESI-MS Found: m/z 490.3[M+H]+

PRODUCTION EXAMPLE 12

Production of ethyl (1,4-trans)-4-azido-1-ethylcyclohexanecarboxylate

1) Ethyl (1,4-cis)-1-ethyl-4-hydroxycyclohexanecarboxylate

To a solution of 1.65 g of ethyl 1-ethyl-4-oxocyclohexanecarboxylate (which was prepared by the method as described in *J. Am. Chem. Soc.*, 1979, 101, 6414–6420) in 17 ml of methanol, 250 mg of sodium borohydide was added at 0° C., followed by 35 minutes' stirring at the same temperature. After adding water to the reaction liquid, the solvent was distilled off under reduced pressure. Water was added to the residue, followed by extraction with ethyl acetate. The ethyl acetate layer was washed with saturated brine, dried on anhydrous magnesium sulfate, and the solvent was distilled off. The residue was separated and purified on silica gel column chromatography (ethyl acetate/hexane=1/3) to provide 648 mg of the title compound.

2) Ethyl (1,4-trans)-4-azido-1-ethylcyclohexanecarboxylate

Reactions were conducted following the steps of Production Example 10 using ethyl (1,4-cis)-1-ethyl-4-(methanesulfonyloxy)-cyclohexanecarboxylate [which was prepared by the hitherto known method, from the compound as obtained in 1) above and methanesulfonyl chloride] in place of ethyl (1,4-trans)-4-methanesulfonyloxy-1-methylcyclohexanecarboxylate, to provide the title compound. Moreover, by conducting the same procedures using ethyl 1-methoxymethyl-4-oxocyclohexanecarboxylate as the starting material, ethyl (1,4-trans)-4-azido-1-(methoxymethyl)-cyclohexanecarboxylate can be prepared.

EXAMPLE 16

Production of 5-chloro-6-[4-ethyl-(2S*)-2-methylpiperazin-1-yl]-2-[(1,3-trans)-3-methoxycarbonylamino-1-methylcyclobutylcarbonyl]benzimidazole and 5-chloro-6-[4-ethyl-(2R*)-2-methylpiperazin-1-yl]-2-[(1,3-trans)-3-methoxycarbonylamino-1-methylcyclobutylcarbonyl]benzimidazole Reactions were conducted following the steps of Example 1, using (1,3-trans)-3-azido-N,1-dimethyl-N-methoxycyclobutanecarboxamide [which was prepared from (1,3-trans)-3-azido-1-methylcyclobutanecarboxylic acid and N,O-dimethylhydroxylamine hydrochloride by the hitherto known production method] in place of (1,4-trans)-4-azido-N,1-dimethyl-N-methoxycyclohexanecarboxamide, to provide the title compounds as a pale yellow, oily substance.

1HNMR(400 MHz, CDCl3)δ: 0.80–1.00(3H, m),1.00–1.30(3H, m), 1.40–1.82(3H, m),1.99–2.22(3H, m),2.36–3.00(6H, m), 3.08–3.50(4H, m),3.67(3H, s),3.90–4.08(1H, m),4.78–4.96(1H, m), 7.16–7.92(2H, m)
ESI-MS Found: m/z 448.3[M+H]+

PRODUCTION EXAMPLE 13

Production of (1,3-trans)-3-azido-1-methylcyclobutanecarboxylic acid

1) Methyl (1,3-cis)-3-benzyloxy-1-methylcyclobutanecarboxylate

To a solution of 4.9 ml of 1.5N lithium diisopropylamide-cyclohexane solution, 5 ml of a tetrahydrofuran solution containing 1.08 g of methyl 3-(benzyloxy)cyclobutanecarboxylate (which was prepared by the method as described in *Tetrahedron*, 1965, 21, 2749–2769) in 5 ml of tetrahydrofuran was added at −78° C. in nitrogen atmosphere, followed by 30 minutes' stirring at the same temperature. To the solution further 0.46 ml of iodomethane was added at −78° C., followed by 30 minutes' stirring at room temperature. Saturated aqueous ammonium chloride solution was added to the reaction liquid which was then extracted with ethyl acetate. The ethyl acetate layer was washed with saturated brine, dried on anhydrous magnesium sulfate and the solvent was distilled off. The residue was separated and purified on silica gel column chromatography (ethyl acetate/hexane=1/30) to provide 360 mg of the title compound.

2) Methyl (1,3-cis)-3-hydroxy-1-methylcyclobutanecarboxylate

To a solution of 611 mg of the compound as obtained in 1) above in 8 ml of methanol, 100 mg of 10% palladium-on-carbon catalyst was added and stirred for 14 hours under hydrogen atmosphere (1 atm.). Filtering the catalyst off from the reaction solution, the filtrate was condensed under reduced pressure, to provide 375 mg of the title compound.

3) Methyl (1,3-trans)-3-azido-1-methylcyclobutanecarboxylate

The title compound was obtained through the reactions similar to the steps of Production Example 10, using ethyl (1,3-cis)-3-methanesulfonyloxy-1-methylcyclobutanecarboxylate [which was prepared by the hitherto known method, from the compound as obtained in 2) above and methanesulfonyl chloride] in place of ethyl (1,4-trans)-4-methanesulfonyloxy-1-methylcyclohexanecarboxylate.

4) (1,3-trans)-3-azido-1-methylcyclobutanecarboxylic acid

To a solution of 330 mg of the compound as obtained in 3) above in 3 ml of methanol, 3 ml of 1N potassium hydroxide was added, followed by an hour's heating under reflux. 6N hydrochloric acid was added to the reaction liquid which then was extracted with chloroform. The chloroform layer was dried on anhydrous magnesium sulfate and solvent was distilled off, to provide 302 mg of the title compound.

EXAMPLE 17

Production of 5-chloro-2-(2,2-dimethylbutyryl)-6-[4-ethyl-(2S*)-2-methylpiperazin-1-yl]benzimidazole and 5-chloro-2-(2,2-dimethylbutyryl)-6-[4-ethyl-(2R*)-2-methylpiperazin-1-yl]benzimidazole Reactions were conducted following the steps 1) and 4) of Example 1 using N-methoxy-N,2,2-trimethylbuylamide (which was prepared from 2,2-dimethylbutyric acid and N,O-dimethylhydroxylamine hydrochloride by the hitherto known method) in place of (1,4-trans)-4-azido-N,1-dimethyl-N-methoxycyclohexanecarboxamide, to provide the title compounds as a pale yellow, oily substance.

1HNMR(300 MHz, CDCl3)δ: 0.74–0.90(3H, m), 0.93 (3H, d, J=6.2 Hz),1.14(3H, t, J=7.2 Hz),1.48(6H, s), 2.05–2.22(3H, m),2.34–2.60(3H, m),2.65–3.00(3H, m), 3.10–3.50(2H, m),7.20–8.00(2H, m)

ESI-MS Found: m/z 377.1[M+H]+

EXAMPLE 18

Production of 5-chloro-6-[4-ethyl-(2S*)-2-methylpiperazin-1-yl]-2-pivaloylbenzimidazole and 5-chloro-6-[4-ethyl-(2R*)-2-methylpiperazin-1-yl]-2-pivaloylbenzimidazole Reactions were conducted following the steps 1) and 4) of Example 1 using N-methoxy-N-methylpiavalamide (which was prepared from pivalic acid and N,O-dimethylhydroxylamine hydrochloride by the hitherto known method) in place of (1,4-trans)-4-azido-N,1-dimethyl-N-methoxycyclohexanecarboxamide, to provide the title compounds as a pale yellow, oily substance.

1HNMR(400 MHz, CDCl3)δ: 0.93(3H, d, J=6.4 Hz), 1.10–1.40(3H, m),1.40–1.58(9H, m),1.90–2.65(4H, m), 2.79–3.55(5H, m),7.20–7.98(2H, m)

ESI-MS Found: m/z 363.2[M+H]+

EXAMPLE 19

Production of 5-chloro-2-(3,3-dimethylbutyryl)-6-[4-ethyl-(2S*)-2-methylpiperazin-1-yl]benzimidazole and 5-chloro-2-(3,3-dimethylbutyryl)-6-[4-ethyl-(2R*)-2-methylpiperazin-1-yl]benzimidazole Reactions were conducted following the steps 1) and 4) of Example 1 using N-methoxy-N,3,3-trimethylbutylamide (which was prepared from 3,3-dimethylbutyric acid and N,O-dimethylhydroxylamine hydrochloride by the hitherto known method) in place of (1,4-trans)-4-azido-N,1-dimethyl-N-methoxycyclohexanecarboxamide, to provide the title compounds as a pale yellow, oily substance.

1HNMR(400 MHz, CDCl3)δ: 0.90–1.40(15H, m), 2.05–2.60(4H, m),2.68–3.01(3H, m),3.08–3.60(4H, m), 7.20–8.00(2H, m)

ESI-MS Found: m/z 377.2[M+H]+

EXAMPLE 20

Production of 5-chloro-6-[4-ethyl-(2S*)-2-methylpiperazin-1-yl]-2-(4-methyltetrahydropyranyl-4-carbonyl) benzimidazole-fumaric acid salt and 5-chloro-6-[4-ethyl-(2R*)-2-methylpiperazin-1-yl]-2-(4-methyltetrahydropyranyl-4-carbonyl) benzimidazole-fumaric acid salt Reactions were conducted following the steps 1) and 4) of Example 1 using N,4-dimethyl-N-methoxytetrahydropyrane-4-carboxamide [which was prepared from 4-methyltetrahydropyrane-4-carboxylic acid (prepared by the method described in WO 99/37644) and N,O-dimethylhydroxylamine hydrochloride by the hitherto known production method] in place of (1,4-trans)-4-azido-N,1-dimethyl-N-methoxycyclohexanecarboxamide, to provide 5-chloro-6-(4-ethyl-2-methylpiperazin-1-yl)-2-(4-methyltetrahydropyranyl-4-carbonyl) benzimidazole (2S*-configuration) and (2R*-configuration).

Each of said compounds was converted to fumaric acid salt in the manner similar to the step 2) of Example 3, to provide the title compounds as a pale yellow powder.

1HNMR(300 MHz, CD3OD)δ: 0.98(3H, d, J=5.3 Hz), 1.38(3H, t, J=7.0 Hz),1.59(3H, s),1.73–1.88(2H, m), 2.60–2.66(2H, m),2.82–2.98(1H, m),3.02–3.33(5H, m), 3.49–3.70(5H, m),3.75–3.83(2H, m),6.71(2H, s),7.58(1H, brs), 7.78(1H, brs)

ESI-MS Found: m/z 405.3[M+H]+

EXAMPLE 21

Production of 5-chloro-6-[4-ethyl-(2S*)-2-methylpiperazin-1-yl]-2-[(1,4-trans)-1-methyl-4-(2-methyltetrazol-5-yl)cyclohexylcarbonyl]benzimidazole and 5-chloro-6-[4-ethyl-(2R*)-2-methylpiperazin-1-yl]-2-[(1,4-trans)-1-methyl-4-(2-methyltetrazol-5-yl) cyclohexylcarbonyl]benzimidazole Reactions were conducted following the steps 1) and 4) of Example 1 using ethyl (1,4-trans)-1-methyl-4-(2-methyltetrazol-5-yl)cyclohexanecarbxylate* in place of (1,4-trans)-4-azido-N,1-dimethyl-N-methoxycyclohexanecarboxamide, to provide the title compounds as a pale yellow powder.

1HNMR(300 MHz, CD3OD)δ: 0.90(3H, d, J=6.0 Hz), 1.15(3H, t, J=7.2 Hz),1.58(3H, s),1.95–2.28(9H, m), 2.36–2.58(3H, m),2.72–3.04(3H, m),3.11–3.21(1H, m), 3.32–3.46(1H, m),4.33(3H, s),7.45–7.80(2H, m)

ESI-MS Found: m/z 485.3[M+H]+

PRODUCTION EXAMPLE 14

Production of ethyl (1,4-trans)-1-methyl-4-(2-methyltetrazol-5-yl)-cyclohexanecarboxylate 1) Ethyl (1,4-trans)-4-cyano-1-methylcyclohexanecarboxylate To a solution of 2.56 g of ethyl (1,4-cis)-4-methanesulfonyloxy-1-methylcyclohexanecarboxylate [which was prepared from 1.80 g of ethyl (1,4-cis)-4-hydroxy-1-methylcyclohexanecarboxylate (prepared by the method as described in *Chem. Pharm. Bull.*, 1984, 32, 2267–2278) and methanesulfonyl chloride by the hitherto known method] in 20 ml of DMF, 1.00 g of sodium cyanide was added, followed by 3 hours' stirring at 80° C. and 14 hours' stirring at 100° C. Water was added to the reaction liquid followed by extraction with ethyl acetate. The ethyl acetate layer was washed with saturated brine, dried on anhydrous magnesium sulfate, and the solvent was distilled off. The resulting residue was separated and purified on silica gel column chromatography (ethyl acetate/hexane=1/6) to provide 475 mg of the title compound.

2) Ethyl (1,4-trans)-1-methyl-4-(tetrazol-5-yl)cyclohexanecarboxylate

To a solution of 470 mg of the compound as obtained in 1) above in 5 ml of toluene, 235 mg of sodium azide and 605 mg of triethylamine hydrochloride were added, and stirred for 3 days at 100° C. 5N hydrochloric acid was added to the reaction liquid which then was extracted with chloroform. The chloroform layer was dried on anhydrous magnesium sulfate and the solvent was distilled off. The residue was separated and purified on silica gel column chromatography (chloroform/methanol=20/1) to provide 446 mg of the title compound.

3) Ethyl (1,4-trans)-1-methyl-4-(2-metyltetrazol-5-yl)-cyclohexanecarboxylate

To a solution of 440 mg of the compound as obtained in 2) above in 5 ml of dimethylformamide, 762 mg of cesium carbonate was added, and stirred for 40 minutes at 60° C. To the reaction liquid 0.17 ml of iodomethane was added at room temperature, and stirred for 14 hours at the same temperature. Water was added to the reaction liquid, followed by extraction with diethyl ether. The diethyl ether layer was washed with saturated brine, dried on anhydrous magnesium sulfate and the solvent was distilled off. The residue was separated and purified on silica gel column chromatography (ethyl acetate/hexane=1/6) to provide 258 mg of the title compound.

EXAMPLE 22

Production of 2-(1-acetyl-4-methylpiperidinyl-4-carbonyl)-5-chloro-6-[4-ethyl-(2S*)-2-methylpiperazin-1-yl]benzimidazole and 2-(1-acetyl-4-methylpiperidinyl-4-carbonyl)-5-chloro-6-[4-ethyl-(2R*)-2-methylpiperazin-1-yl]benzimidazole Reactions were conducted following the steps 1) and 4) of Example 1 using ethyl 1-acetyl-4-methylpiperidin-4-carboxylate* in place of (1,4-trans)-4-azido-N,1-dimethyl-N-methoxycyclohexanecarboxamide, to provide 2-(1-acetyl-4-methylpiperidinyl-4-carbonyl)-5-chloro-6-(4-ethyl-2-methylpiperazin-1-yl) benzimidazole (2S*-configuration) and (2R*-configuration) as a yellow, oily substance.

1HNMR(300 MHz, CDCl3)δ: 0.93(3H, d, J=6.0 Hz), 1.16(3H, t, J=7.2 Hz),1.62(3H, s),1.73–1.79(3H, m), 2.11 (3H, s),2.12–2.19(1H, m),2.46–2.96(8H, m),3.15–3.43(4H, m), 3.59–3.70(1H, m),4.02–4.08(1H, m),7.61–7.92(2H, m)

ESI-MS Found: m/z 446.3[M+H]+

PRODUCTION EXAMPLE 15

Preparation of ethyl 1-acetyl-4-methylpiperidine-4-carboxylate

To 543 mg of 1-tert-butoxycarbonyl-4-methylpiperidine-4-carboxylate (prepared by the method taught in WO 97/12876),8 ml of 10% hydrogen chloride in methanol solution was added, stirred for 2 days at room temperature, and the solvent was distilled off under reduced pressure. This compound was dissolved in 8 ml of pyridine, to which further 0.38 ml of acetic anhydride was added, followed by 3 hours' stirring at room temperature. The reaction liquid was condensed under reduced pressure, to which saturated ammonium chloride solution was added, followed by extraction with ethyl acetate. The ethyl acetate layer was washed with saturated brine, dried on anhydrous magnesium sulfate, and the solvent was distilled off. The residue was separated and purified on silica gel column chromatography (ethyl acetate/hexane=3/2) to provide 256 mg of the title compound.

EXAMPLE 23

Production of 5-chloro-6-[4-ethyl-(2S*)-2-methylpiperazin-1-yl]-2-[(1,4-cis)-4-hydroxy-1-methylcyclohexylcarbonyl]benzimidazole and 5-chloro-6-[4-ethyl-(2R*)-2-methylpiperazin-1-yl]-2-[(1,4-cis)-4-hydroxy-1-methylcyclohexylcarbonyl]benzimidazole Reactions were conducted following the steps 1) and 4) of Example 1 using 4-methyl-2-oxabicyclo[2.2.2]octan-3-one (which was prepared by the method as described in Chem. Pharm. Bull., 1984, 32, 2267–2278) in place of (1,4-trans)-4-azido-N,1-dimethyl-N-methoxycyclohexanecarboxamide, to provide the title compounds as a yellow oily substance.

1HNMR(300 MHz, CDCl3)δ: 0.92(3H, d, J=5.9 Hz), 1.10–1.80(4H, m),1.20(3H, t, J=7.0 Hz),1.54(3H, d, J=4.3 Hz), 1.80–2.70(7H, m),2.70–3.10(4H, m),3.10–3.32(1H, m), 3.32–3.60(1H, m),3.60–3.87(1H, m),7.20–8.00(2H, m), 10.60–11.40(1H, br)

ESI-MS Found: m/z 419.3[M+H]+

EXAMPLE 24

Production of 5-chloro-6-[4-ethyl-(2S*)-2-methylpiperazin-yl]-2-[(1,4-trans)-4-hydroxy-1-methylcyclohexylcarbonyl]benzimidazole and 5-chloro-6-[4-ethyl-(2R*)-2-methylpiperazin-1-yl]-2-[(1,4-trans)-4-hydroxy-1-methylcyclohexylcarbonyl] benzimidazole 1) 5-Chloro-6-(4-ethyl-2-methylpiperazin-1-yl)-2-[(1,4-cis)-4-hydroxy-1-methylcyclohexylcarbonyl]-1-[2-(trimethylsilyl)ethoxymethyl]benzimidazole and 6-chloro-5-(4-ethyl-2-methylpiperazin-1-yl)-2-[(1,4-cis)-4-hydroxy-1-methylcyclohexylcarbonyl]-1-[2-(trimethylsilyl)-ethoxymethyl]benzimidazole (1:1 Mixture)

A reaction was conducted following the step 1) of Example 1 using 4-methyl-2-oxabicyclo[2,2,2]octan-3-one in place of (1,4-trans)-4-azido-N,1-dimethyl-N-methoxycyclohexancarboxamide, to provide the title compounds as a position isomeric mixture.

2) 2-[(1,4-Trans)-4-benzoyloxy-1-methylcyclohexylcarbonyl]-5-chloro-6-(4-ethyl-2-methylpiperazin-1-yl)-1-[2-(trimethylsilyl)ethoxymethyl]benzimidazole and 2-[(1,4-trans)-4-benzoyloxy-1-methylcyclohexylcarbonyl]-6-chloro-5-(4-ethyl-2-methylpiperazin-1-yl)-1-[2-(trimethylsilyl)ethoxymethyl]benzimidazole (1:1 Mixture)

To a solution of 120 mg of the compounds as obtained in 1) above in 4 ml of tetrahydrofuran, 115 mg of triphenylphosphine, 88 mg of diisopropyl azodicarboxylate and 53 mg of benzoic acid were added by the order stated, followed by 10 minutes' stirring at 0° C. Saturated aqueous sodium hydrogencarbonate solution was added to the reaction liquid which then was extracted with ethyl acetate. The ethyl acetate layer was dried on anhydrous magnesium sulfate and the solvent was distilled off. The residue was separated and purified on preparative thin-layer chromatography [Kieselgel™ 60F$_{254}$, Art 5744 (Merck); chloroform/methanol=19/1] to provide 75 mg of the title compounds.

3) 5-Chloro-6-(4-ethyl-2-methylpiperazin-1-yl)-2-[(1,4-trans)-4-hydroxy-1-methylcyclohexylcarbonyl]-1-[2-(trimethylsilyl)-ethoxymethyl]benzimidazole and 6-chloro-5-(4-ethyl-2-methylpiperazin-1-yl)-2-[(1,4-trans)-4-hydroxy-1-methylcyclohexylcarbonyl]-1-[2-(trimethylsilyl)ethoxymethyl]benzimidazole (1:1 Mixture)

To a solution of 41 mg of the compounds as obtained in 2) above in 1 ml of methanol, 0.2 ml of 28% sodium methoxide-methanol solution was added, followed by 14 hours' stirring at room temperature. Water was added to the reaction liquid, followed by extraction with chloroform. The chloroform layer was dried on anhydrous magnesium sulfate, and the solvent was distilled off. The residue was separated and purified by preparative thin-layer chromatography [Kieselgel™ 60F$_{254}$, Art 5744(Merck); chloroform/methanol=15/1] to provide 35 mg of the title compounds.

4) 5-Chloro-6-[4-ethyl-(2S*)-2-methylpiperazin-1-yl]-2-[(1,4-trans)-4-hydroxy-1-methylcyclohexylcarbonyl]benzimidazole and 5-chloro-6-[4-ethyl-(2R*)-2-methylpiperazin-1-yl]-2-[(1,4-trans)-4-hydroxy-1-methylcyclohexylcarbonyl]benzimidazole A reaction was conducted following the step 4) of Example 1 using the compounds as obtained in 3) above in place of the compound as obtained in the step 3) of Example 1, to provide the title compounds as a yellow oily substance.

1HNMR(300 MHz, CDCl3)δ: 0.93(3H, d, J=5.9 Hz), 1.17(3H, t, J=6.8 Hz),1.40–2.36(9H, m),1.60(3H, d, J=3.6 Hz), 2.36–2.65(3H, m),2.65–3.05(3H, m),3.05–3.34(1H, m), 3.34–3.60(1H, m),3.60–3.90(1H, m),7.20–8.00(2H, m), 10.00–10.50(1H, br)

ESI-MS Found: m/z 419.3[M+H]+

EXAMPLE 25

Production of 6-[4-ethyl-(2S*)-2-methylpiperazin-1-yl]-5-methyl-2-pivaloylbenzimidazole and 6-[4-ethyl-(2R*)-2-methylpiperazin-1-yl]-5-methyl-2-pivaloylbenzimidazole Using the compounds as obtained in Production Example 3 in place of those obtained in Production Example 2, and using N-methoxy-N-methylpivalamide in place of (1,4-trans)-4-azido-N,1-dimethyl-N-methoxycyclohexanecarboxamide, reactions were conducted following the steps 1) and 4) of Example 1, to provide the title compounds as a pale yellow, oily substance.

1HNMR(400 MHz, CDCl3)δ: 0.84(3H, d, J=6.4 Hz), 1.14(3H, t, J=7.6 Hz),1.40–1.65(9H, m),1.80–2.10(1H, m), 2.20–2.60(6H, m),2.70–3.04(4H, m),3.20–3.35(1H, m), 7.20–7.78(2H, m)10.00–10.22(1H, m)

ESI-MS Found: m/z 343.4[M+H]+

EXAMPLE 26

Production of 6-[4-ethyl-(2S*)-2-methylpiperazin-1-yl]-5-methyl-2-(4-methyltetrahydropyranyl-4-carbonyl) benzimidazole-fumaric acid salt and 6-[4-ethyl-(2R*)-2-methylpiperazin-1-yl]-5-methyl-2-(4-methyltetrahydropyranyl-4-carbonyl) benzimidazole-fumaric acid salt Using the compounds as obtained in Production Example 3 in place of those obtained in Production Example 2, and using N,4-dimethyl-N-methoxytetrahydropyrane-4-carboxamide in place of (1,4-trans)-4-azido-N,1-dimethyl-N-methoxycyclohexanecarboxamide, reactions were conducted following the steps 1) and 4) of Example 1, to provide (2S*-configuration) and (2R*-configuration) of 6-(4-ethyl-2-methylpiperazin-1-yl)-5-methyl-2-(4-methyltetrahydropyranyl-4-carbonyl) benzimidazole.

Converting each of the above compounds to fumaric acid salt similarly to the step 2) of Example 3, the title compounds were obtained as a pale yellow powder.

1HNMR(300 MHz, CD3OD)δ: 0.91(3H, d, J=6.0 Hz), 1.39(3H, t, J=6.9 Hz),1.59(3H, s),1.72–1.88(2H, m), 2.44 (3H, s),2.59–2.70(2H, m),2.81–2.93(1H, m), 3.02–3.31(3H, m),3.28(2H, q, J=6.9 Hz),3.48–3.63(5H, m), 3.73–3.82(2H, m),6.71(2H, s),7.45–7.60(2H, br)

ESI-MS Found: m/z 385.4[M+H]+

EXAMPLE 27

Production of 2-(1-acetyl-4-methylpiperidinyl-4-carbonyl)-6-[4-ethyl-(2S*)-2-methylpiperazin-1-yl]-5-methylbenzimidazole and 2-(1-acetyl-4-methylpiperidinyl-4-carbonyl)-6-[4-ethyl-(2R*)-2-methylpiperazin-1-yl]-5-methylbenzimidazole Using the compounds as obtained in Production Example 3 in place of those obtained in Production Example 2, and ethyl 1-acetyl-4-methylpiperidine-4-carboxylate, in place of (1,4-trans)-4-azido-N,1-dimethyl-N-methoxycyclohexancarboxamide, reactions were conducted following the steps 1) and 4) of Example 1, to provide (2S*-configuration) and (2R*-configuration) of 2-(1-acetyl-4-methylpiperidinyl-4-carbonyl)-6-(4-ethyl-2-methylpiperazin-1-yl)-2-methylbenzimidazole as a yellow oily substance.

0.84(3H, d, J=6.0 Hz),1.15(3H, t, J=7.2 Hz), 1.63(3H, d, J=4.5 Hz),1.70–1.79(2H, m), 1.97–2.06(2H, m)2.11(3H, s),2.24–2.39(1H, m), 2.42(3H, d, J=6.0 Hz),2.46–2.53(2H, m),2.68–2.99(6H, m), 3.11–3.34(3H, m),3.58–3.70(1H, m),4.00–4.08(1H, m), 7.25–7.35(1H, m),7.62–7.69(1H, m)

ESI-MS Found: m/z 426.4[M+H]+

EXAMPLE 28

Production of 5-chloro-2-(3,3-dimethylbutyryl)-6-(4-ethylpiperazin-1-yl)-7-fluorobenzimidazole Reactions were conducted following the steps 1) and 4) of Example 1, except that the compounds as obtained in Production Example 5 were used in place of those as obtained in Production Example 2, N-methoxy-N,3,3-trimethylbutylamide was used in place of (1,4-trans)-4-azido-N, 1-dimethyl-N-methoxycyclohexanecarboxamide and that the optical resolution step was not conducted, to provide the title compound as a pale brown solid.

1HNMR(400 MHz, CDCl3)δ: 1.10(9H, s),1.15(3H, t, J=7.2 Hz), 2.20–3.60(12H, m),7.30–7.82(1H, m)

ESI-MS Found: m/z 381.1[M+H]+

EXAMPLE 29

Production of 5-chloro-2-(2,2-dimethylbutyryl)-6-(4-ethylpiperazin-1-yl)-7-fluorobenzimidazole Reactions were conducted following the steps 1) and 4) of Example 1, except that the compounds as obtained in Production Example 5 were used in place of those as obtained in Production Example 2, N-methoxy-N,2,2-trimethylbutylamide was used in place of (1,4-trans)-4-azido-N, 1-dimethyl-N-methoxycyclohexanecarboxamide and that the optical resolution step was not conducted, to provide the title compound as a pale yellow, oily substance.

1HNMR(400 MHz, CDCl3)δ: 0.80(3H, t, J=7.2 Hz), 1.16(3H, t, J=7.2 Hz),1.47(6H, s),1.90–3.60(12H, m), 7.30–7.80(1lH,m)

ESI-MS Found: m/z 381.1[M+H]+

EXAMPLE 30

Production of 5-chloro-2-(2,2-dimethylbutyryl)-6-[4-(2-hydroxmethyl)-(2S*)-2-methylpiperazin-1-yl]benzimidazole and 5-chloro-2-(2,2-dimethylbutyryl)-6-[4-(2-hydroxethyl)-(2R*)-2-methylpiperazin-1-yl]benzimidazole 1) 5-Chloro-2-(2,2-dimethylbutyryl)-6-(2-methylpiperazin-1-yl) benzimidazole Reactions were conducted following the steps 1) and 4) of Example 1, except that the compounds as obtained in Production Example 7 were used in place of those as obtained in Production Example 2, N-methoxy-N,2,2-trimethylbutylamide was used in place of (1,4-trans)-4-azido-N,1-dimethyl-N-methoxycyclohexanecarboxamide and that the optical resolution step was not conducted, to provide the title compounds.

2) 5-Chloro-2-(2,2-dimethylbutyryl)-6-[4-(2-hydroxyethyl)-(2S*)-2-methylpiperazin-1-yl]benzimidazole and 5-chloro-2-(2,2-dimethylbutyryl)-6-[4-(2-hydroxyethyl)-(2R*)-2-methylpiperazin-1-yl]benzimidazole Using the compound as obtained in 1) above in place of that as obtained in the step 1) of Example 6, reactions were conducted following the steps 2) and 3) of Example 6. The title compounds were obtained as a pale yellow, oily substance, not being converted to their corresponding fumaric acid salts 1HNMR(400 MHz, CDCl3)δ: 0.60–1.02(6H, m),1.48 (6H, s), 2.18(2H, q, J=7.6 Hz),2.22–2.40(1H, m),2.50–3.00 (6H, m), 3.14–3.80(4H, m),7.20–8.00(2H, m)

ESI-MS Found: m/z 393.2[M+H]+

EXAMPLE 31

Production of 2-(2,2-dimethylbutyryl)-6-[4-(2-hydroxyethyl)-(2S*)-2-methylpiperazin-1-yl]-5-methylbenzimidazole and 2-(2,2-dimethylbutyryl)-6-[4-(2-hydroxyethyl)-(2R*)-2-methylpiperazin-1-yl]-5-methylbenzimidazole 1) 2-(2,2-Dimethylbutyryl)-5-methyl-6-(2-methylpiperazin-1-yl) benzimidazole Reactions were conducted following the steps 1) and 4) of Example 1, except that the compounds as obtained in Production Example 9 were used in place of those as obtained in Production Example 2, N-methoxy-N,2,2-trimethylbutylamide was used in place of (1,4-trans)-4-azido-N,1-dimethyl-N-methoxycyclohexanecarboxamide and that the optical resolution step was not conducted, to provide the title compounds.

2) 2-(2,2-Dimethylbutyryl)-6-[4-(2-hydroxyethyl)-(2S*)-2-methylpiperazin-1-yl]-5-methylbenzimidazole and 2-(2,2-dimethylbutyryl)-6-[4-(2-hydroxyethyl)-(2R*)-2-methylpiperazin-1-yl]-5-methylbenzimidazole Using the compound as obtained in 1) above in place of the compound as obtained in the step 1) of Example 6, reactions were conducted following the steps 2) and 3) of Example 6, to provide the title compounds as a pale yellow solid, not being converted to their corresponding fumaric acid salts.

1HNMR(400 MHz, CDCl3)δ: 1.70–1.92(6H, m), 1.35–1.60(6H, m),2.00–2.25(3H, m),2.35–3.02(10H, m), 3.20–3.35(1H, m),3.67(2H, t, J=5.6 Hz),7.16–7.72(2H, m)

ESI-MS Found: m/z 373.3[M+H]+

EXAMPLE 32

Production of 6-[4-(2-hydroxyethyl)-(2S*)-2-methylpiperazin-1-yl]-5-methyl-2-pivaloylbenzimidazole and 6-[4-(2-hydroxyethyl)-(2R*)-2-methylpiperazin-1-yl]-5-methyl-2-pivaloylbenzimidazole 1) 5-Methyl-6-(2-methylpiperazin-1-yl)-2-pivaloylbenzimidazole Reactions were conducted following the steps 1) and 4) of Example 1, except that the compounds as obtained in Production Example 9 were used in place of those as obtained in Production Example 2, N-methoxy-N-methylpiavalamide was used in place of (1,4-trans)-4-azido-N,1-dimethyl-N-methoxycyclohexanecarboxamide and that the optical resolution step was not conducted, to provide the title compounds.

2) 6-[4-(2-Hydroxyethyl)-(2S*)-2-methylpiperazin-1-yl]-5-methyl-2-pivaloylbenzimidazole and 6-[4-(2-hydroxyethyl)-(2R*)-2-methylpiperazin-1-yl]-5-methyl-2-pivaloylbenzimidazole Using the compound as obtained in 1) above in place of that as obtained in the step 1) of Example 6, reactions were conducted following the steps 2) and 3) of Example 6, to provide the title compounds as a white solid, without converting them to their corresponding fumaric acid salts.

1HNMR(400 MHz, CDCl3)δ: 0.85(3H, d, J=5.6 Hz), 1.40–1.70(9H, m),2.00–2.28(1H, m),2.28–3.10(10H, m), 3.15–3.32(1H, m),3.60–3.80(2H, m),7.20–7.80(2H, m)

ESI-MS Found: m/z 359.2[M+H]+

EXAMPLE 33

Production of 5-chloro-6-(4-ethyl-2-methylpiperazin-1-yl)-2-(1-pyrrolidinylcarbonyl) benzimidazole Reactions were conducted following the steps 1) and 4) of Example 1, except that pyrrolidine carbonyl chloride was used in place of (1,4-trans)-4-azido-N,1-dimethyl-N-methoxycyclohexanecarboxamide and that the optical resolution step was not conducted, to provide the title compound as a pale yellow, oily substance.

1HNMR(400 MHz, CDCl3)δ: 0.92(3H, d, J=6.0 Hz), 1.14(3H, t, J=7.2 Hz),1.70–2.30(5H, m),2.30–2.60(3H, m), 2.66–3.50(5H, m),3.81(2H, t, J=7.2 Hz),4.33(2H, t, J=7.2 Hz), 7.00–7.95(2H, m)

ESI-MS Found: m/z 376.1[M+H]+

EXAMPLE 34

Production of 5-chloro-6-(4-ethyl-2-methylpiperazin-1-yl)-2-(1-piperidinylcarbonyl) benzimidazole Reactions were conducted following the steps 1) and 4) of Example 1, except that piperidine carbonyl chloride was used in place of (1,4-trans)-4-azido-N,1-dimethyl-N-methoxycyclohexanecarboxamide and that the optical resolution step was not conducted, to provide the title compound as colorless oily substance.

1HNMR(300 MHz, CDCl3)δ: 0.92(3H, d, J=6.2 Hz), 1.17(3H, t, J=7.0 Hz),1.21–1.90(9H, m),2.40–2.62(2H, m), 2.75–3.02(2H, m),3.12–3.25(1H, m),3.32–3.54(1H, m), 3.73–3.82(2H, m),4.53–4.65(2H, m),7.32–7.90(2H, m)

ESI-MS Found: m/z 390.1[M+H]+

EXAMPLE 35

Production of 5-chloro-2-[(diethylamino)carbonyl]-6-(4-ethyl-2-methylpiperazin-1-yl) benzimidazole Reactions were conducted following the steps 1) and 4) of Example 1, except that [(diethylamino)carbonyl]chloride was used in place of (1,4-trans)-4-azido-N,1-dimethyl-N-methoxycyclohexanecarboxamide and that the optical resolution step was not conducted, to provide the title compound as a pale yellow, oily substance.

1HNMR(400 MHz, CDCl3)δ: 0.92(3H, d, J=6.4 Hz), 1.15(3H, t, J=6.8 Hz),1.20–1.50(6H, m),2.00–2.22(1H, m), 2.35–2.60(3H, m),2.70–3.00(3H, m),3.08–3.50(2H, m), 3.66(2H, q, J=6.8 Hz),4.20–4.50(2H, m),7.20–8.00(2H, m)

ESI-MS Found: m/z 378.2[M+H]+

EXAMPLE 36

Production of 5-chloro-2-[(diisopropylamino)carbonyl]-6-(4-ethyl-2-methylpiperazin-1-yl) benzimidazole Reactions were conducted following the steps 1) and 4) of Example 1, except that [(diisopropylamino)carbonyl]chloride was used in place of (1,4-trans)-4-azido-N,1-dimethyl-N-methoxycyclohexanecarboxamide and that the optical resolution step was not conducted, to provide the title compound as a colorless oily substance.

1HNMR(400 MHz, CDCl3)δ: 0.91(3H, d, J=6.4 Hz), 1.15(3H, t, J=7.2 Hz),1.34(6H, d, J=5.2 Hz), 1.58(6H, d, J=6.0 Hz),2.00–2.30(1H, m),2.37–2.70(3H, m), 2.70–3.08 (3H, m),3.08–3.80(3H, m),6.00–6.25(1H, m), 7.20–8.00(2H, m)

ESI-MS Found: m/z 406.3[M+H]+

EXAMPLE 37

Production of 2-[(tert-butylamino)carbonyl]-5-chloro-6-(4-ethyl-2-methylpiperazin-1-yl) benzimidazole Reactions were conducted following the steps 1) and 4) of Example 1, except that tert-butyl isocyanate was used in place of (1,4-trans)-4-azido-N,1-dimethyl-N-methoxycyclohexanecarboxamide and that the optical resolution step was not conducted, to provide the title compound as a pale yellow, oily substance.

1HNMR(400 MHz, CDCl3)δ: 0.70–1.02(3H, m), 1.15 (3H, t, J=7.2 Hz),1.59(9H, s),2.00–2.22(1H, m), 2.32–2.60 (3H, m),2.65–3.02(3H, m),3.10–3.60(2H, m), 7.20–7.80(2H, m)

ESI-MS Found: m/z 378.1[M+H]+

EXAMPLE 38

Production of 5-chloro-2-[(cyclohexylamino)carbonyl]-6-(4-ethyl-2-methylpiperazin-1-yl) benzimidazole Reactions were conducted following the steps 1) and 4) of Example 1, except that cyclohexyl isocyanate was used in place of (1,4-trans)-4-azido-N,1-dimethyl-N-methoxycyclohexanecarboxamide and that the optical resolution step was not conducted, to provide the title compound as a colorless oily substance.

1HNMR(400 MHz, CDCl3)δ: 0.70–2.30(17H, m), 2.30–2.60(3H, m),2.70–3.00(3H, m),3.06–3.50(2H, m), 3.90–4.08(1H, m),7.20–7.85(2H, m)

ESI-MS Found: m/z 404.2[M+H]+

EXAMPLE 39

Production of 5-chloro-2-[cyclohexyl(methyl)amino]carbonyl]-6-(4-ethyl-2-methylpiperazin-1-yl) benzimidazole Reactions were conducted following the steps 1) and 4) of Example 1, except that [[cyclohexyl(methyl)amino]carbonyl]chloride (which was prepared by the method as described in *Bioorg. Med. Chem. Lett.*, 1998, 8, 1471–1476) was used in place of (1,4-trans)-4-azido-N,1-dimethyl-N-methoxycyclohexanecarboxamide and that the optical resolution step was not conducted, to provide the title compound as a yellow oily substance.

1HNMR(300 MHz, CDCl3)δ: 0.83–0.97(3H, m), 1.09–1.21(3H, m),1.39–1.98(10H, m),2.11–2.23(1H, m), 2.38–2.62(3H, m),2.74–3.00(3H, m),3.09(1.5H, s), 3.13–3.53(2H, m),3.64(1.5H, s),4.55–4.68(0.5H, m), 5.61–5.78(0.5H, m),7.30–7.90(2H, m)

ESI-MS Found: m/z 418.2[M+H]+

PRODUCTION EXAMPLE 16

Production of 5-chloro-6-(4-ethyl-2-methylpiperazin-1-yl)-2-iodo-1-[2-(trimethylsilyl)ethoxymethyl] benzimidazole and 6-chloro-5-(4-ethyl-2-methylpiperazin-1-yl)-2-iodo-1-[2-(trimethylsilyl)ethoxymethyl]benzimidazole (1:1 Mixture)

To a solution of 207 mg of the compounds as obtained in Production Example 2 in 4 ml of tetrahydrofuran, 0.48 ml of 1.5 N n-butyl lithium-hexane solution was added at −78° C., followed by 70 minutes' stirring at the same temperature. To the same solution a solution of 171 mg of N-iodosuccinimide in 4 ml of tetrahydrofuran was added at −78° C., and stirred for 3 hours and 45 minutes at room temperature. 1N aqueous sodium hydroxide solution was added to the reaction liquid which was then extracted with ethyl acetate. The ethyl acetate layer was washed with saturated brine, dried on anhydrous magnesium sulfate, and the solvent was distilled off. The residue was separated and purified on silica gel column chromatography (chloroform/methanol=20/1) to provide 185 mg of the title compounds as a position isomeric mixture.

EXAMPLE 40

Production of 5-chloro-6-(4-ethyl-2-methylpiperazin-1-yl)-2-[[isopropyl(methyl)amino]carbonyl] benzimidazole 1) 5-Chloro-6-(4-ethyl-2-methylpiperazin-1-yl)-2-[[isopropyl(methyl)-amino]carbonyl]-1-[2-(trimethylsilyl)ethoxymethyl]benzimidazole and 6-chloro-5-(4-ethyl-2-methylpiperazin-1-yl)-2-[[isopropyl(methyl)-amino]carbonyl]-1-[2-(trimethylsilyl)ethoxymethyl]benzimidazole (1:1 Mixture)

To a solution of 23 mg of the compounds as obtained in Production Example 16 in 1 ml of dimethylformamide, 1 mg of palladium (II) acetate, 2 mg of triphenylphosphine, 0.013 ml of isopropylmethylamine and 11 mg of sodium hydrogencarbonate were successively added by the order stated, followed by 4 hours and 20 minutes stirring in carbon monoxide atmosphere (1 atm.) at 70° C. 1N aqueous sodium hydroxide solution was added to the reaction liquid which was then extracted with ethyl acetate. The ethyl acetate layer was washed with saturated brine, dried on anhydrous magnesium sulfate and the solvent was distilled off. The residue was separated and purified on preparative thin layer chromatography [Kiselgel™ 60F$_{254}$, Art. 5744(Merck); chloroform/methanol=10/1] to provide 18 mg of the title compounds.

2) 5-Chloro-6-(4-ethyl-2-methylpiperazin-1-yl)-2-[[isopropyl(methyl)-amino]carbonyl]benzimidazole To a solution of 18 mg of the compounds as obtained in 1) above in 1 ml of tetrahydrofuran, 0.5 ml of 1N tetrabutylammonium fluoride-tetrahydrofuran solution was added, followed by 13.5 hours' stirring at 50° C. 1N aqueous sodium hydroxide solution was added to the reaction liquid which then was extracted with ethyl acetate. The ethyl acetate layer was washed with saturated brine, dried on anhydrous magnesium sulfate and the solvent was distilled off. The residue was separated and purified by preparative thin-layer chromatography [Kiselgel™ 60F$_{254}$, Art. 5744 (Merck); chloroform/methanol/aqueous ammonia=200/10/1] to provide 4 mg of the title compound as a colorless amorphous substance.

1HNMR(300 MHz, CDCl3)δ: 0.92(3H, d, J=6.2 Hz), 1.13–1.40(9H, m),1.93–2.67(4H, m),2.78–3.02(3H, m), 3.06(1.5H, s),3.12–3;56(2H, m),3.61(1.5H, m), 4.93–5.10 (0.5H, m),6.14–6.32(0.5H, m),7.30–7.87(2H, m)

ESI-MS Found: m/z 378.2[M+H]+

EXAMPLE 41

Production of 5-chloro-2-[[tert-butyl(methyl)amino]carbonyl]-6-(4-ethyl-2-methylpiperazin-1-yl) benzimidazole Reactions were conducted following the steps of Example 40, except that tert-butylmethylamine was used in place of isopropylmethylamine, to provide the title compound as a pale yellow, oily substance.

1HNMR(200 MHz, CDCl3)δ: 0.80–0.97(3H, m),1.15–1.40(3H, m), 1.55(9H, s),1.71–2.11(2H, m),2.11–2.42(1H, m),2.43–2.71(2H, m), 2.80–3.28(3H, m),3.35–3.70(1H, m),3.60(3H, s),7.30–7.84(2H, m)

ESI-MS Found: m/z 392.2[M+H]+

EXAMPLE 42

Production of 5-chloro-2-[[[2-(dimethylamino)ethyl](methyl)amino]-carbonyl]-6-(4-ethyl-2-methylpiperazin-1-yl) benzimidazole Reactions were conducted following the steps of Example 40, except that N,N,N'-trimethylethylenediamine was used in place of isopropylmethylamine, to provide the title compound as a colorless, oily substance.

1HNMR(200 MHz, CDCl3)δ: 0.92(3H, d, J=6.1 Hz), 1.16(3H, t, J=7.2 Hz),2.00–2.21(2H, m),2.33(6H, s), 2.37–3.03(8H, m),3.20(3H, s),3.31–3.55(1H, m), 3.66–3.85 (1H, m),4.21–4.43(1H, m),7.30–7.78(2H, m)

ESI-MS Found: m/z 407.2[M+H]+

EXAMPLE 43

Production of 5-chloro-6-(4-ethyl-(2S*)-2-methylpiperazin-1-yl)-2-(isobutoxycarbonyl) benzimidazole and 5-chloro-6-(4-ethyl-(2R*)-2-methylpiperazin-1-yl)-2-(isobutoxycarbonyl) benzimidazole To a solution of 152 mg of the compound as obtained in the step 3) of Production Example 2 and 0.045 ml of pyrrolidine in 2 ml of ethanol, 0.041 ml of formaline was added, followed by 4 hours' heating under reflux. Water was added to the reaction liquid which then was extracted with chloroform. The chloroform layer was dried on anhydrous magnesium sulfate and the solvent was distilled off. To a solution of the resultant residue in 2 ml of tetrahydrofuran, 0.55 ml of 1.5N n-butyl lithium-hexane solution was added at −78° C., followed by an hour's stirring at the same temperature. To the same solution 0.107 ml of isobutyl chloroformate was added at −78° C., followed by 30 minutes' stirring at the same temperature. To the reaction liquid 2N hydrochloric acid and saturated aqueous sodium hydrogencarbonate solution were added successively, followed by extraction with ethyl acetate. The ethyl acetate layer was dried on anhydrous magnesium sulfate, and the solvent was distilled off. The residue was separated and purified by preparative thin-layer chromatography [Kiselgel™ 60F$_{254}$, Art. 5744(Merck); chloroform/methanol/aqueous ammonia=100/10/1] to provide a racemic modification of the title compounds.

The racemic modification was optically resolved with an optically active column (Daicel Chemical Ind., Ind., CHIRALPAK AD Column; 0.1% diethylamine, hexane/isopropyl alcohol=9/1). From the earlier fraction 13 mg of 5-chloro-6-(4-ethyl-2-methylpiperazin-1-yl)-2-(isobutoxycarbonyl) benzimidazole (2S*-configuration) was obtained and from the later fraction, 13 mg of (2R*-configuration) of the same compound, both as a colorless oily substance. (Because the two were unidentified, the former is called 2S*-configuration and the other, 2R*-configuration for convenience).

1HNMR(400 MHz, CDCl3)δ: 0.91(3H, d, J=6.0 Hz), 1.01(6H, d, J=6.8 Hz),1.15(3H.t,J=7.2 Hz),2.00–2.22(2H, m), 2.38–2.64(3H, m),2.70–3.50(5H, m),4.23(2H, d, J=7.2 Hz), 7.20–8.10(2H, m)

ESI-MS Found: m/z 379.1[M+H]+

PRODUCTION EXAMPLE 17

Production of 5-chloro-6-(4-ethyl-2-methylpiperazin-1-yl)-7-fluoro-1-[2-(trimethylsilyl)ethoxymethyl]benzimidazole and 6-chloro-5-(4-ethyl-2-methylpiperazin-1-yl)-4-fluoro-1-[2-(trimethylsilyl)-ethoxymethyl]benzimidazole (1:1 Mixture)

Reactions were conducted following the steps of Production Example 2 using 4-chloro-2,3-difluoro-6-nitroaniline in place of the compound as obtained in Production Example 1, to provide the title compounds as a position isomeric mixture.

EXAMPLE 44

Production of 5-chloro-6-[4-ethyl-(2S*)-2-methylpiperazin-1-yl]-7-fluoro-2-[(1,4-trans)-4-methoxycarbonylamino-1-methylcyclohexylcarbonyl]benzimidazole-fumaric acid salt and 5-chloro-6-[4-ethyl-(2R*)-2-methylpiperazin-1-yl]-7-fluoro-2-[(1,4-trans)-4-methoxycarbonylamino-1-methylcyclohexylcarbonyl]benzimidazole-fumaric acid salt Reactions were conducted following the steps of Example 1 using the compounds as obtained in Production Example 17 in place of those obtained in Production Example 2, to provide (2S*-configuration) and (2R*-configuration) of 5-chloro-6-[4-ethyl-2-methylpiperazin-1-yl]-7-fluoro-2-[(1,4-trans)-4-methoxycarbonylamino-1-methylcyclohexylcarbonyl]benzimidazole. Each of said compounds was converted to fumaric acid salt similarly to the step 2) of Example 3, and the title compounds were obtained as a white solid.

1HNMR(300 MHz, CD3OD)δ: 0.95(3H, d, J=6.3 Hz), 1.36(3H, t, J=7.3 Hz),1.44–1.69(5H, m),1.70–1.86(2H, m), 1.90–2.26(4H, m),2.66–2.79(1lH,m),3.00–3.25(4H, m), 3.39–3.59(4H, m),3.62(3H, s),3.71–3.87(1H, m),4.86(2H, s), 6.87–6.99(1H, m),7.50–7.60(1H, brs)

ESI-MS Found: m/z 494.3[M+H]+

PRODUCTION EXAMPLE 18

Production of 6-(4-tert-butoxycarbonyl-2-methylpiperazin-1-yl)-7-fluoro-5-methyl-1-[2-(trimethylsilyl)ethoxymethyl]benzimidazole and 5-(4-tert-butoxycarbonyl-2-methylpiperazin-1-yl)-4-fluoro-6-methyl-1-[2-(trimethylsilyl)ethoxymethyl]benzimidazole (1:1 Mixture)

1) 4-Bromo-2,3-difluoro-6-nitroaniline

To a solution of 3.00 g of 2,3-difluoro-6-nitroaniline in 30 ml of dimethylformamide, 6.14 g of N-bromosuccinimide was added, followed by an hour's stirring at 90° C. Water was added to the reaction liquid which then was extracted with ethyl acetate. The ethyl acetate layer was washed with saturated brine, dried on anhydrous magnesium sulfate and the solvent was distilled off. The residue was separated and purified on silica gel column chromatography (ethyl acetate/hexane=1/6) to provide 3.21 g of the title compound.

2) 4-Bromo-3-(4-tert-butoxycarbonyl-2-methylpiperazin-1-yl)-2-fluoro-6-nitroaniline A reaction was conducted following the step 1) of Production Example 2 using the compound obtained in 1) above in place of the compound as obtained in Example 1, and using 1-tert-butoxycarbonyl-3-methylpiperazine in place of 1-ethyl-3-methylpiperazine, to provide the title compound.

3) 3-(4-Tert-butoxycarbonyl-2-methylpiperazin-1-yl)-2-fluoro-4-methyl-6-nitroaniline A reaction was conducted following the step 2) of Production Example 9 using the compound as obtained in 2) above in place of the compound as obtained in the step 1) of Production Example 9, to provide the title compound.

4) 6-Amino-3-(4-tert-butoxycarbonyl-2-methylpiperazin-1-yl)-2-fluoro-4-methylaniline A reaction was conducted following the step 2) of Production Example 2 using the compound as obtained in 3) above in place of the compound as obtained in the step 1) of Production Example 2, to provide the title compound.

5) 6-(4-Tert-butoxycarbonyl-2-methylpiperazin-1-yl)-7-fluoro-5-methyl-1-[2-(trimethylsilyl)ethoxymethyl]benzimidazole and 5-(4-tert-butoxycarbonyl-2-methylpiperazin-1-yl)-4-fluoro-6-methyl-1-[2-(trimethylsilyl)ethoxymethyl]benzimidazole (1:1 Mixture)

Reactions were conducted following the steps 2) and 3) of Production Example 7 using the compound as obtained in 4) above in place of the compound as obtained in the step 1) of Production Example 7, to provide the title compounds as a position isomeric mixture.

EXAMPLE 45

Production of 6-[4-ethyl-(2S*)-2-methylpiperazin-1-yl]-7-fluoro-2-[(1,4-trans)-4-methoxycarbonylamino-1-methylcyclohexylcarbonyl]-5-methylbenzimidazole and 6-[4-ethyl-(2R*)-2-methylpiperazin-1-yl]-7-fluoro-2-[(1,4-trans)-4-methoxycarbonylamino-1-methylcyclohexylcarbonyl]-5-methylbenzimidazole 1) 7-Fluoro-2-[(1,4-trans)-4-methoxycarbonylamino-1-methylcyclohexylcarbonyl]-5-methyl-6-(2-methylpiperazin-1-yl) benzimidazole Reactions were conducted following the steps of Example 1, except that the compounds as obtained in Production Example 18 were used in place of those as obtained in Production Example 2 and that the optical resolution step was not conducted, to provide the title compound.

2) 6-[4-Ethyl-(2S*)-2-methylpiperazin-1-yl]-7-fluoro-2-[(1,4-trans)-4-methoxycarbonylamino-1-methylcyclohexylcarbonyl]-5-methylbenzimidazole and 6-[4-ethyl-(2R*)-2-methylpiperazin-1-yl]-7-fluoro-2-[(1,4-trans)-4-methoxycarbonylamino-1-methylcyclohexylcarbonyl]-5-methylbenzimidazole To a solution of 144 mg of the compound as obtained in 1) above and 0.022 ml of acetaldehyde in 2 ml of methanol, 1.3 ml of an advancedly prepared 0.3M methanol solution of sodium cyanoborohydride and zinc chloride (1:0.5, molar ratio) was added at 0° C., followed by 15 minutes' stirring at the same temperature. Saturated aqueous sodium hydrogencarbonate solution was added to the reaction liquid which then was extracted with ethyl acetate. The ethyl acetate layer was dried on anhydrous magnesium sulfate and the solvent was distilled off. Separating and purifying the residue on silica gel column chromatography (chloroform/methanol/aqueous ammonia=100/5/0.5) to provide a racemic modification of the title compounds.

This racemic modification was optically resolved with an optically active column (Daicel Co., Ltd., CHIRALPAK AD Column; 0.1% diethylamine, hexane/ethanol=93/7), to obtain from the earlier fraction 21 mg of 6-(4-ethyl-2-methylpiperazin-1-yl)-7-fluoro-2-[(1,4-trans)-4-methoxycarbonylamino-1-methylcyclohexylcarbonyl]-5-methylbenzimidazole (2S*-configuration), and 20 mg of the (2R*-configuration) of the same compound from the later fraction, both as a white solid. (Because the two were unidentified, for convenience the one is labeled as 2S*-configuration and the other, as 2R*-configuration.)

1HNMR(400 MHz, CDCl3)δ:0.80(3H, d, J=6.4 Hz), 1.14 (3H, t, J=7.2 Hz),1.20–1.35(3H, m),1.42–1.64(5H, m), 1.80–2.28(5H, m),2.30–2.52(5H, m),2.68–3.00(3H, m), 3.20–3.80(6H, m),4.60–4.75(1H, m),7.00–7.50(1H, m)
ESI-MS Found: m/z 474.4[M+H]+

EXAMPLE 46

Production of 2-[(1,4-trans)-4-methoxycarbonylamino-1-methylcyclohexylcarbonyl]-6-[4-(2-methoxyethyl)-(2S*)-2methylpiperazin-1-yl]-5-methylbenzimidazole-fumaric acid salt and 2-[(1,4-trans)-4-methoxycarbonylamino-1-methylcyclohexylcarbonyl]-6-[4-(2-methoxyethyl)-(2R*)-2-methylpiperazin-1-yl]-5-methylbenzimidazole-fumaric acid salt Reactions were conducted following the steps 2),3) and 4) of Example 7 using the compounds as obtained in the step 1) of Example 12 in place of those as obtained in the step 1) of Example 7, and using bromoethyl methyl ether in place of 2-fluoroethyl methanesulfonate, to provide the title compounds as a pale brown powder.

1HNMR(300 MHz, CD3OD)δ: 0.91(3H, d, J=6.3 Hz), 1.45–1.90(4H, m),1.56(3H, s),1.90–2.35(4H, m),2.45(3H, s), 2.60–3.67(10H, m),3.43(3H, s),3.63(3H, s),3.67–3.85 (2H, m), 6.70(2H, s),6.85–7.08(1H, brs),7.30–7.80(2H, m)
ESI-MS Found: m/z 486.4[M+H]+

EXAMPLE 47

Production of 2-[(1,4-trans)-1-ethyl-4-(methoxycarbonylamino)-cyclohexylcarbonyl]-6-[4-ethyl-(2S*)-2-methylpiperazin-1-yl]-5-methylbenzimidazole-fumaric acid salt and 2-[(1 4-trans)-1-ethyl-4-(methoxycarbonylamino)-cyclohexylcarbonyl]-6-[4-ethyl-(2R*)-2-methylpiperazin-1-yl]-5-methylbenzimidazole-fumaric acid salt Reactions were conducted following the steps of Example 1 using the compounds as obtained in Production Example 3 in place of those as obtained in Production Example 2, and using ethyl (1,4-trans)-4-azido-1-ethylcyclohexanecarboxylate in place of (1,4-trans)-4-azido-N,1-dimethyl-N-methoxycyclohexanecarboxamide, to provide (2S*-configuration) and (2R*-configuration) of 2-[(1,4-trans)-1-ethyl-4-(methoxycarbonylamino)cyclohexylcarbonyl]-6-(4-ethyl-2-methylpiperazin-1-yl)-5-methylbenzimidazole. Each of said compounds was converted to the corresponding fumaric acid salt similarly to the step 2) of Example 3 and the title compounds were obtained as a white powder.

1HNMR(200 MHz, CD3OD)δ: 0.68(3H, t, J=7.4 Hz), 0.92(3H, d, J=6.0 Hz),1.40(3H, t, J=7.3 Hz),1.47–1.82(4H, m), 1.93–2.38(6H, m),2.43(3H, s),2.81–3.36(7H, m), 3.36–3.70(4H, m),3.62(3H, s),6.72(2H, s),7.52(2H, brs)
ESI-MS Found: m/z 470.2[M+H]+

EXAMPLE 48

Production of 5-chloro-6-[4-ethyl-(2S*)-2-methylpiperazin-1-yl]-2-(4-methoxycarbonylamino-2,2-dimethylbutyryl) benzimidazole and 5-chloro-6-[4-ethyl-(2R*)-2-methylpiperazin-1-yl]-2-(4-methoxycarbonylamino-2,2-dimethylbutyryl) benzimidazole Reactions were conducted following the steps of Example 1 using methyl 4-azido-2,2-dimethylbutyrate* in place of (1,4-trans)-4-azido-N,1-dimethyl-N-methoxycyclohexanecarboxamide, to provide the title compounds as a colorless oily substance.

1HNMR(300 MHz, CDCl3)δ: 0.69–0.96(5H, m), 1.14 (3H, t, J=7.5 Hz),1.18–1.38(5H, m),1.50–2.58(6H, m), 2.70–2.97(3H, m),3.09–4.62(7H, m),7.25–7.96(2H, m), 9.32–9.52(1H, m)
ESI-MS Found: m/z 450.4[M+H]+

PRODUCTION EXAMPLE 19

Production of methyl 4-azido-2,2-dimethylbutyrate

To a solution of 1.3 g of methyl 4-azido-2-methylbutyrate (which was prepared by the method as described in *Tetrahedron*, 1987, 43, 1811–1822) in 13 ml of tetrahydrofuran, 16.7 ml of 1.5N lithium diisopropylamide-cyclohexane solution was added at −78° C. in nitrogen atmosphere, followed by 30 minutes' stirring at the same temperature. To the solution 1.6 ml of iodomethane was added at −78° C., followed by 30 minutes' stirring at the same temperature. Water was added to the reaction liquid, followed by extraction with diethyl ether. The diethyl ether layer was washed with saturated brine, dried on anhydrous magnesium sulfate and the solvent was distilled off. The residue was separated and purified on silica gel column chromatography (ethyl acetate/hexane=1/30) to provide 406 mg of the title compound.

EXAMPLE 49

Production of 2-[2,2-bis(methoxymethyl)propionyl]-6-[4-ethyl-(2S*)-2-methylpiperazin-1-yl]-5-methylbenzimidazole and 2-[2,2-bis(methoxymethyl)propionyl]-6-[4-ethyl-(2R*)-2-methylpiperazin-1-yl]-5-methylbenzimidazole Reactions were conducted following the steps 1) and 4) of Example 1 using the compounds as obtained in Production Example 3 in place of those as obtained in Production Example 2 and using 2,2-bis(methoxymethyl)-N-methoxy-N-methyl-propionamide (which was prepared from 2,2-bis(methoxymethyl)propionic acid and N,O-dimethylhydroxylamine hydrochloride by the hitherto known method) in place of (1,4-trans)-4-azido-N,1-dimethyl-N-methoxycyclohexanecarboxamide, to provide the title compounds as a pale yellow, amorphous substance.

1HNMR(300 MHz, CDCl3)δ: 0.85(3H, d, J=6.0 Hz), 1.09–1.20(3H, m),1.50–1.69(7H, m),1.90–2.53(5H, m), 2.70–3.00(3H, m),3.20–3.34(6H, m),3.92–4.03(4H, m), 7.21–7.33(1H, m),7.60–7.71(1H, m),9.85–9.98(1H, m)
ESI-MS Found: m/z 403.2[M+H]+

EXAMPLE 50

Production of 5-chloro-6-[4-ethyl-(2S*)-2-methylpiperazin-1-yl]-2-[2-(p-tolyl)isobutyryl]benzimidazole and 5-chloro-6-[4-ethyl-(2R*)-2-methylpiperazin-1-yl]-2-[2-(p-tolyl)isobutyryl]benzimidazole Reactions were conducted following the steps 1) and 4) of Example 1 using N-methoxy-N-methyl-2-(p-tolyl)isobutylamide [which was prepared from 2-(p-tolyl)isobutyric acid (prepared by the method as described in *J. Am. Chem. Soc.*, 1968, 90, 2092–2096) and N,O-dimethylhydroxylamine hydrochloride by the hitherto known method] in place of (1,4-trans)-4-azido-N,1-dimethyl-N-methoxycyclohexanecarboxamide, to provide the title compounds as a white solid.

1HNMR(400 MHz, CDCl3)δ: 0.86(3H, d, J=7.2 Hz), 1.14(3H, t, J=7.2,14.4 Hz),1.84(6H, s),2.00–2.20(1H, m), 2.27(3H, s),2.60–3.50(8H.m),7.05–7.80(6H, m),9.94(1H, brs)

ESI-MS Found: m/z 439.4[M+H]+

PRODUCTION EXAMPLE 20

Production of 5-chloro-6-(4-ethylpiperazin-1-yl)-1-[2-(trimethylsilyl)-ethoxymethyl]benzimidazole and 6-chloro-5-(4-ethylpiperazin-1-yl)-1-[2-(trimethylsilyl)-ethoxymethyl]benzimidazole (1:1 Mixture)

1) 4-Chloro-5-(4-ethylpiperazin-1-yl)-2-nitroaniline

To a solution of 20.0 g of 4,5-dichloro-2-nitroaniline and 16.0 g of 1-ethylpiperazine in 50 ml of dimethylsulfoxide, 20.0 g of potassium carbonate was added, followed by 2 hours' stirring at 120° C. Water was added to the reaction liquid, followed by extraction with diethyl ether. The diethyl ether layer was successively washed with water and saturated brine, dried on anhydrous magnesium sulfate, and the solvent was distilled off. The residue was recrystallized from chloroform-diethyl ether, to provide 20.3 g of the title compound.

2) 5-Chloro-6-(4-ethylpiperazin-1-yl)-1-[2-(trimethylsilyl)-ethoxymethyl]benzimidazole and 6-chloro-5-(4-ethylpiperazin-1-yl)-1-[2-(trimethylsilyl)-ethoxymethyl]benzimidazole (1:1 Mixture)

Reactions were conducted following the steps 2),3) and 4) of Production Example 2 using the compound as obtained in 1) above in place of that obtained in the step 1) of Production Example 2, to obtain the title compounds as a position isomeric mixture.

PRODUCTION EXAMPLE 21

Production of ethyl (1,4-trans)-1,4-dimethyl-4-hydroxycyclohexanecarboxylate

To a solution of 4.50 g of ethyl 1-methyl-4-oxocyclohexanecarboxylate (which was prepared by the method described in WO 92/18463) in 100 ml of tetrahydrofuran, 80 ml of 0.93M methyl magnesium bromide-tetrahydrofuran solution was added at −78° C., followed by 25 minutes' stirring at the same temperature. Water was added to the reaction liquid which then was extracted with ethyl acetate. The ethyl acetate layer was washed with saturated brine, dried on anhydrous magnesium sulfate and the solvent was distilled off. Separating and purifying the residue on silica gel column chromatography (ethyl acetate/hexane=1/2) to provide 1.74 g of the title compound.

EXAMPLE 51

Production of 5-chloro-2-[(1,4-trans)-1,4-dimethyl-4-hydroxycyclohexylcarbonyl]-6-(4-ethylpiperazin-1-yl) benzimidazole 1) 5-Chloro-2-[(1,4-trans)-1,4-dimethyl-4-hydroxycyclohexylcarbonyl]-6-(4-ethylpiperazin-1-yl)-1-[2-(trimethylsilyl)ethoxymethyl]benzimidazole and 6-chloro-2-[(1,4-trans)-1,4-dimethyl-4-hydroxycyclohexylcarbonyl]-5-(4-ethylpiperazin-1-yl)-1-[2-(trimethylsilyl)ethoxymethyl] benzimidazole (1:1 Mixture)

To a solution of 4.80 g of 2,2,6,6-tetramethylpiperidine in 140 ml of tetrahydrofuran, 17.4 ml of 1.57N n-butyl lithium-hexane solution was added at −78° C. in nitrogen atmosphere, followed by 15 minutes' stirring at 0C. To the solution, a solution of 2.70 g of the compound as obtained in Production Example 20 in 7 ml of tetrahydrofuran and a solution of 1.64 g of ethyl (1,4-trans)-1,4-dimethyl-4-hydroxycyclohexanecarboxylate (Production Example 21) in 7 ml of tetrahydrofuran were successively added at −78° C., followed by an hour's stirring at temperatures ranging −78° C.−−60° C. Saturated aqueous sodium hydrogencarbonate solution was added to the reaction liquid which then was extracted with ethyl acetate. The ethyl acetate layer was washed with saturated brine, dried on anhydrous magnesium sulfate and the solvent was distilled off. Separating and purifying the residue on silica gel column chromatography (chloroform/methanol=50/1),1.86 g of the title compounds was obtained as a position isomeric mixture.

2) 5-Chloro-2-[(1,4-trans)-1,4-dimethyl-4-hydroxycyclohexylcarbonyl]-6-(4-ethylpiperazin-1-yl) benzimidazole To 2.30 g of the compounds as obtained in 1) above, 42 ml of 1N tetrabutylammonium fluoride-tetrahydrofuran solution was added, and heated for 4 hours under reflux. Saturated aqueous sodium hydrogencarbonate solution was added to the reaction liquid which then was extracted with ethyl acetate. The ethyl acetate layer was washed with saturated brine, dried on anhydrous magnesium sulfate and the solvent was distilled off. Separating and purifying the residue on silica gel column chromatography (chloroform/methanol/aqueous ammonia=300/10/1),1.67 g of the title compound was obtained as a yellow solid.

1HNMR(300 MHz, CDCl3)δ: 1.00–1.30(2H, m), 1.16 (3H, t, J=7.3 Hz),1.19(3H, s),1.30–1.92(7H, m), 2.45–2.85 (6H, m),2.54(2H, d, J=7.3 Hz),2.98–3.26(4H, m), 7.10–7.95 (2H, m),10.02–10.27(1H, br)

ESI-MS Found: m/z 419.3[M+H]+

PRODUCTION EXAMPLE 22

Production of 6-(4-ethylpiperazin-1-yl)-5-methyl-1-[2-(trimethylsilyl)-ethoxymethyl]benzimidazole and 5-(4-ethylpiperazin-1-yl)-6-methyl-1-[2-(trimethylsilyl) ethoxymethyl]benzimidazole (1:1 Mixture)

Reactions were conducted following the steps of Production Example 3 using 1-ethylpiperazine in place of 1-ethyl-3-methylpiperazine, to provide the title compounds as a position isomeric mixture.

PRODUCTION EXAMPLE 23

Production of 6-[(S)-1,4-diazabicyclo[4.3.0]nonan-4-yl]-5-methyl-1-[2-(trimethylsilyl)ethoxymethyl] benzimidazole and 5-[(S)-1,4-diazabicyclo[4.3.0] nonan-4-yl]-6-methyl-1-[2-(trimethylsilyl)-ethoxymethyl]benzimidazole (1:1 Mixture)

Reactions were conducted following the steps of Production Example 3 using (S)-1,4-diazabicyclo[4.3.0]nonane (which was prepared by the method described in *J. Med. Chem.* 1993, 36, 2311–2320) in place of 1-ethyl-3-methylpiperazine, to provide the title compounds as a position isomeric mixture.

PRODUCTION EXAMPLE 24

Production of ethyl (1,4-trans)-4-methyl-1-methoxymethyl-4-trimethylsilyloxycyclohexanecarboxylate 1) Ethyl 4-hydroxy-4-methylcyclohexanecarboxylate To a solution of 25.0 g of ethyl 4-oxocyclohexanecarboxylate in 500 ml of diethyl ether, 150 ml of 1.6N methyl lithium-ether solution was added at −60° C. in nitrogen atmosphere, followed by 30 minutes' stirring at −60° C. Water was added to the reaction liquid which then was extracted with ethyl acetate. The ethyl acetate layer was washed with saturated brine, dried on anhydrous magnesium sulfate and the solvent was distilled off. The residue was separated and purified on silica gel column chromatography (ethyl acetate/hexane=1/4) to provide 22.7 g of the title compound.

2) Ethyl 4-methyl-4-trimethylsilyloxycyclohexanecarboxylate

To a solution of 22.7 g of the compound as obtained in 1) above in 150 ml of methylene chloride, 50 ml of triethylamine and 44 ml of trimethylsilyl-trifluoromethane sulfonate were added at 0° C. in nitrogen atmosphere, followed by 2 hours' stirring at room temperature. Water was added to the reaction liquid which then was extracted with ether. The ether layer was washed with saturated brine, dried on anhydrous magnesium sulfate and the solvent was distilled off. The residue was separated and purified on silica gel column chromatography (ethyl acetate/hexane=1/50) to provide 30.1 g of the title compound.

3) Ethyl (1,4-trans)-4-methyl-1-methoxymethyl-4-trimethylsilyloxycyclohexanecarboxylate To a solution of 19.6 ml of diisopropylamine in 500 ml of tetrahydrofuran, 52.4 ml of 1.6N butyl lithium-hexane solution was added at −78° C. in nitrogen atmosphere, followed by 15 minutes' stirring at the same temperature. To the solution, a solution of 30.1 g of the compound as obtained in 2) above in 50 ml of tetrahydrofuran was added at −78° C., followed by 30 minutes' stirring at the same temperature. To the solution 10.6 ml of chloromethyl methyl ether was added and the temperature was raised to 0° C. Water was added to the reaction solution which then was extracted with ethyl acetate. The ethyl acetate layer was successively washed with water and saturated brine, dried on anhydrous magnesium sulfate and the solvent was distilled off. The residue was separated and purified on silica gel chromatography (ethyl acetate/hexane=1/50) to provide 14.2 g of the title compound.

EXAMPLE 52

Production of 6-(4-ethylpiperazin-1-yl)-2-[(1,4-trans)-4-hydroxy-1-methoxymethyl-4-methylcyclohexylcarbonyl]-5-methylbenzimidazole Reactions were conducted following the steps of Example 51 using the compound as obtained in Production Example 22 in place of those as obtained in Production Example 20 and using the compound as obtained in Production Example 24 in place of that as obtained in Production Example 21, to provide the title compound as a yellow amorphous substance.

1HNMR(300 MHz, CDCl3)δ: 1.10–1.22(6H, m),1.39–1.67(4H, m), 1.67–1.92(4H, m),2.43(1.5H, s),2.45 (1.5H, s),2.53(2H, q, J=7.3 Hz), 2.58–2.79(4H, m),2.96–3.05(4H, m),3.17(1.5H, s),3.18(1.5H, s), 4.07(2H, s),7.12(0.5H, s),7.31(0.5H, s),7.52(0.5H, s),7.66(0.5H, s), 10.08(0.5H,bs),10. 16(0.5H,bs)

ESI-MS Found: m/z 429.3[M+H]+

EXAMPLE 53

Production of 6-[(S)-1,4- ziazabicyclo[4.3.0]nonan-4-yl]-2-[(1,4-trans)-4-hydroxy-1-methoxymethyl-4-methylcyclohexylcarbonyl]-5-methylbenzimidazole Reactions were conducted following the steps of Example 51 using the compounds as obtained in Production Example 23 in place of those as obtained in Production Example 22, to provide the title compound as a colorless amorphous substance.

1HNMR(300 MHz, CDCl3)δ: 1.18(3H, s),1.38–1.90(9H, m), 2.17–2.34(2H, m),2.43(3/2H, s),2.45(3/2H, s),2.45–2.52 (1H, m), 2.55–2.68(1H, m),2.70–2.80(2H, m),2.83–3.00 (1H, m), 3.06–3.29(5H, m),3.49(3H, s),4.07(2H, s),7.13(1/ 2H, s), 7.31(1/2H, s),7.57(1/2H, s),7.68(1/2H, s),10.07(1/ 2H, brs), 11.03(1/2H, brs)

ESI-MS Found: m/z 441.3[M+H]+

INDUSTRIAL APPLICABILITY

The compounds of the present invention possess an antagonism to binding of nociceptin to nociceptin receptor ORL1, and are useful as an analgesic against diseases accompanied with pain such as cancerous pain, postoperative pain, migraine, gout, chronic rheumatism, chronic pain and neuralgia; a reliever against tolerance to narcotic analgesic represented by morphine; a reliever against dependence on narcotic analgesic represented by morphine or against addiction; an analgesic enhancer; an antiobestic or appetite suppressor; a treating or preventive agent for cognitive impairment and dementia/amnesia in aging, cerebrovascular diseases and Alzheimer's disease; an agent for treating developmental cognitive abnormality in attention deficit, hyperactivity disorder and learning disability; a remedy for schizophrenia; an agent for treating neurodegenerative diseases represented by Parkinsonism and chorea; an anti-depressant or treating agent for affective disorder; a treating or prophylactic agent for diabetes insipidus; a treating or prophylactic agent for polyuria; a remedy for hypotension, and the like.

What is claimed is:

1. Benzimidazole derivatives which are represented by a general formula [I-1]

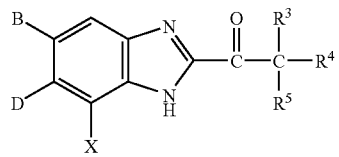

in which

X stands for a hydrogen or halogen,

B stands for a halogen, cyano or optionally fluorine-substituted lower alkyl,

D stands for a group selected from a group consisting of the following formulae [D-1],

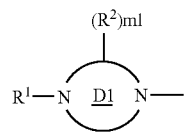

[D-1]

wherein m1 is 0 or an integer of 1 or 2

R¹ stands for hydrogen or a lower alkyl which may optionally be substituted with at least one substituent selected from a group consisting of halogen, hydroxyl, lower alkyloxy and lower cycloalkyl;

R² may be same or different where m1 is 2, and stand for lower alkyl which may optionally be substituted with a substituent selected from a group consisting of halogen, hydroxyl, optionally fluorine-substituted lower alkyloxy, lower alkylcarbonyl, carboxyl, lower alkyloxycarbonyl, carbamoyl, mono-lower alkylcarbamoyl and di-lower alkylcarbamoyl,

stands for a piperazine ring;

R³ stands for hydrogen, a substituent selected from a group consisting of the list α as defined below, or a lower alkyl which may optionally be substituted with a substituent selected from the group consisting of the list α as defined below, R⁴ and R⁵ may be same or different and each stands for hydrogen, a substituent selected from the group consisting of the list α as defined below, or a lower alkyl or lower cycloalkyl which may optionally be substituted with a substituent selected from the group consisting of the list α as defined below, or R⁴ and R⁵ together form, in combination with the carbon atom to which they bind, a 3–10 membered alicyclic group optionally having a hetero atom selected from a group consisting of nitrogen and oxygen, of the following formula [A]

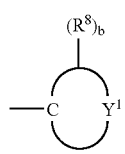

[A]

in which b is 0 or an integer of 1–4,

R⁸ may be same or different where b is 2–4, and bind to optional atom(s) on the aliphatic ring, each standing for a substituent selected from the group consisting of the list α or a lower alkyl which may optionally be substituted with a substituent selected from the group consisting of the list α as defined below, or two R⁸'s together form —NH—C(O)—O—CH₂— or an oxo group, Y¹ stands for —CH₂—, —NR⁹— or —O—, where R⁹ stands for a substituent selected from a group consisting of hydrogen, optionally fluorine-substituted lower alkyl, lower alkylcarbonyl, lower alkyloxycarbonyl, lower alkylsulfonyl, carbamoyl, mono-lower alkylcarbamoyl and di-lower alkylcarbamoyl;

[list α] wherein list α is halogen, hydroxyl, amino, mono-lower alkylamino, di-lower alkylamino, optionally fluorine-substituted lower alkyloxy, lower alkyloxycarbonyl, (lower alkyloxycarbonyl)amino, (lower alkyloxycarbonyl)lower alkylamino, carboxyl, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl)lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl) amino, (di-lower alkylsulfamoyl)amino, (mono-lower alkylsulfamoyl)lower alkylamino, (di-lower alkylsulfamoyl) lower alkylamino, phenyl tetrazolyl or oxadiazolyl which may optionally be substituted with lower alkyl, or their pharmaceutically acceptable salts.

2. Benzimidazole derivatives as defined in claim 1, which are represented by a general formula [I-4]

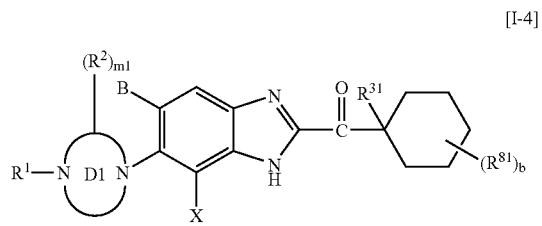

[I-4]

in which R³¹ stands for a lower alkyl optionally substituted with substituent(s) selected from list α given in claim 1, R⁸¹ stands for a substituent selected from said list α, or a lower alkyl which is optionally substituted with a substituent selected from the same list α, and B, X, R¹, R², b, m1 and

—N D1 N— have the same significations as defined in claim 1 and their pharmaceutically acceptable salts.

3. Compounds as defined in any one of claims 1 and 2, in which X is hydrogen or fluorine atom.

4. Compounds as defined in any one of claims 1 and 2, in which B is chlorine atom, cyano or methyl group.

5. Compounds as defined in any one of claims 1 and 2, in which D is a radical selected from the group consisting of 4-methylpiperazin-1-yl, 4-ethylpiperazin-1-yl, 4-isopropylpiperazin-1-yl, 4-(2-fluoroethyl)piperazin-1-yl, 4-(2-methoxyethyl)piperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl, 2,4-dimethylpiperazin-1-yl, 4-(1-hydroxycyclopropyl) methylpiperazin-1-yl, 4-(1-hydroxycyclopropyl)methyl-2-methylpiperazin-1-yl, and 2,2-dimethyl-4-ethylpiperazin-1-yl.

6. Compounds as defined in any one of claims 1 and 2, in which D is a radical selected from the group consisting of 4-methylpiperazin-1-yl, 4-ethylpiperazin-1-yl, 4-(2-fluoroethyl)piperazin-1-yl, 4-(2-methoxyethyl)piperazin-1-yl, 4-ethyl-2-methylpiperazin-1-yl, 4-(2-fluoroethyl-2)-methylpiperazin-1-yl, 4-(2-methoxyethyl)-2-methylpiperazin-1-yl, 4-(2-hydroxyethyl)-2-methylpiperazin-1-yl and 4-(2-hydroxyethyl)piperazin-1-yl.

7. Compounds selected from the group consisting of
5-chloro-6-[4-ethyl-2-methylpiperazin-1-yl]-2-[(1,4-trans)-4-methoxycarbonylamino-1-methylcyclohexylcarbonyl]benzimidazole,
6-[4-ethyl-2-methylpiperazin-1-yl]-2-[(1,4-trans)-4-methoxycarbonylamino-1-methylcyclohexylcarbonyl]-5-methylbenzimidazole,
5-chloro-6-[4-(2-hydroxyethyl)-2-methylpiperazin-1-yl]-2-[(1,4-trans)-4-methoxycarbonylamino-1-methylcyclohexylcarbonyl]benzimidazole,
6-[4-(2-hydroxyethyl)-2-methylpiperazin-1-yl]-2-[(1,4-trans)-4-methoxycarbonylamino-1-methylcyclohexylcarbonyl]-5-methylbenzimi dazole,
5-chloro-2-[(1,4-trans)-1-ethyl-4-(methoxycarbonylamino)-cyclohexylcarbonyl]-6-[4-ethyl-2-methylpiperazin-1-yl]benzimidazole,
2-[(1,4-trans)-1-ethyl-4-(methoxycarbonylamino)cyclohexylcarbonyl]-6-[4-ethyl-2-methylpiperazin-1-yl]-5-methylbenzimidazole,
5-chloro-6-[4-ethyl-2-methylpiperazin-1-yl]-2-[(1,4-trans)-4-hydroxy-1-methylcyclohexylcarbonyl]benzimidazole,
2-(1-acetyl-4-methylpiperidinyl-4-carbonyl)-6-[4-ethyl-2-methylpiperazin-1-yl]-5-methylbenzimidazole,
6-[4-ethyl-2-methylpiperazin-1-yl]-5-methyl-2-(4-methyltetrahydropyranyl-4-carbonyl)benzimidazole,
6-(4-ethyl-2-methylpiperazin-1-yl)-7-fluoro-2-[(1,4-trans)-4-methoxycarbonylamino-1-methylcyclohexylcarbonyl]-5-methylbenzimidazole,
5-chloro-2-[(1,4-trans)-1,4-dimethyl-4-hydroxycyclohexylcarbonyl]-6-(4-ethylpiperazin-1-yl)benzimidazole,
5-chloro-6-(4-ethylpiperazin-1-yl)-2-[(1,4-trans)-4-methoxycarbonylamino-1-methoxycyclohexylcarbonyl]benzimidazole, and
6-(4-ethylpiperazin-1-yl)-2-[(1,4-trans)-4-hydroxy-1-methoxymethyl-4-methylcyclohexylcarbonyl]-5-methylbenzimidazole.

8. Pharmaceutical compositions which comprise the compound(s) as described in claim 1 and pharmaceutically acceptable adjuvants.

9. A method for the treatment of a subject requiring anagesia, which comprises administering an effective amount of the required compound according to claim 1 to the subject.

* * * * *